(12) United States Patent
Claremon et al.

(10) Patent No.: US 8,927,539 B2
(45) Date of Patent: Jan. 6, 2015

(54) CYCLIC INHIBITORS OF 11β-HYDROXYSTEROID DEHYDROGENASE 1 BASED ON THE 1,3-OXAZINAN-2-ONE STRUCTURE

(75) Inventors: David A. Claremon, Maple Glen, PA (US); Katerina Leftheris, Skillman, NJ (US); Linghang Zhuang, Chalfont, PA (US); Colin M. Tice, Ambler, PA (US); Suresh B. Singh, Kendall Park, NJ (US); Yuanjie Ye, Ambler, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 354 days.

(21) Appl. No.: 13/377,374

(22) PCT Filed: Jun. 10, 2010

(86) PCT No.: PCT/US2010/038191
§ 371 (c)(1),
(2), (4) Date: May 7, 2012

(87) PCT Pub. No.: WO2011/011123
PCT Pub. Date: Jan. 27, 2011

(65) Prior Publication Data
US 2012/0208804 A1 Aug. 16, 2012

Related U.S. Application Data

(60) Provisional application No. 61/186,159, filed on Jun. 11, 2009.

(51) Int. Cl.
C07D 413/10 (2006.01)
C07D 413/06 (2006.01)
A61K 31/535 (2006.01)
A61K 31/5355 (2006.01)

(52) U.S. Cl.
USPC ............................. 514/228.8; 544/96; 544/97

(58) Field of Classification Search
USPC ................................... 514/228.8; 544/96, 97
See application file for complete search history.

(56) References Cited

U.S. PATENT DOCUMENTS

| | | |
|---|---|---|
| 3,341,538 A | 9/1967 | Block et al. |
| 3,378,587 A | 4/1968 | Reinhardt |
| 3,681,349 A | 8/1972 | Schwan et al. |
| 3,703,529 A | 11/1972 | Frederick et al. |
| 3,919,047 A | 11/1975 | Vidic et al. |
| 4,009,171 A | 2/1977 | Albertson |
| 4,043,927 A | 8/1977 | Duling et al. |
| 4,108,857 A | 8/1978 | Albertson |
| 4,136,145 A | 1/1979 | Fuchs et al. |
| 4,136,162 A | 1/1979 | Fuchs et al. |
| 4,268,673 A | 5/1981 | Akkerman et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |

(Continued)

FOREIGN PATENT DOCUMENTS

| | | |
|---|---|---|
| DE | 1801556 A1 | 5/1970 |
| DE | 2105743 A1 | 8/1972 |

(Continued)

OTHER PUBLICATIONS

Bosch et al.: Heterocycles 1980, 14, p. 1983-1988.
Ma et al.: Tetrahedron 2007, 63, p. 7523-7531.
Ma et al.: Synthesis 2007, p. 161-163.
Yokoyama et al.: J. Med. Chem. 1979, 22, p. 537-553.
Harno et.al. Trends in Endocrinology and Metabolism, Elsevier Science Publishing, New York 2010, vol. 21, No. 10, pp. 619-627.
Taddayon et.al. Expert opinion on Investigational Drugs, Ashley Publication Ltd. 2003, vol. 12, No. 3, pp. 307-324.

(Continued)

*Primary Examiner* — Kahsay Habte
(74) *Attorney, Agent, or Firm* — McCarter & English LLP; Steven G. Davis; Michael J. DeGrazia

(57) ABSTRACT

Disclosed are compounds represented by Formula (I):

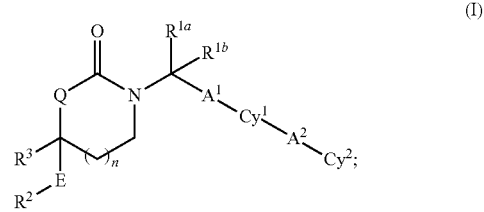

or pharmaceutically acceptable salts, enantiomers or diastereomers thereof. Also disclosed are pharmaceutical compositions comprising the compounds of Formula (I) or pharmaceutically acceptable salts, enantiomers or diastereomers thereof for the therapeutic treatment of diseases associated with the modulation or inhibition of 11β-HSD1 in mammals. Values for the variables of Formula (I) are defined herein.

15 Claims, No Drawings

(56) References Cited

U.S. PATENT DOCUMENTS

| | | |
|---|---|---|
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 8,569,292 B2 | 10/2013 | Claremon et al. |
| 8,575,156 B2 * | 11/2013 | Claremon et al. ......... 514/228.8 |
| 8,592,410 B2 | 11/2013 | Claremon et al. |
| 8,598,160 B2 | 12/2013 | Claremon et al. |
| 8,598,163 B2 | 12/2013 | Claremon et al. |
| 8,673,899 B2 | 3/2014 | Claremon et al. |
| 8,680,281 B2 | 3/2014 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0184549 A1 | 7/2012 | Himmelsbach |
| 2012/0190675 A1 | 7/2012 | Himmelsbach |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | |
|---|---|---|
| DE | 2108954 A1 | 9/1972 |
| DE | 2229695 A1 | 1/1974 |
| DE | 2338369 A1 | 2/1975 |
| DE | 2354002 A1 | 5/1975 |
| DE | 2411382 A1 | 9/1975 |
| DE | 2437610 A1 | 2/1976 |
| DE | 2828039 A1 | 1/1980 |
| DE | 19918725 A1 | 10/2000 |
| DE | 19929348 A1 | 12/2000 |
| DE | 10034623 A1 | 1/2002 |
| EP | 0415642 A1 | 3/1991 |
| EP | 0454444 A1 | 10/1991 |
| EP | 0471591 A2 | 2/1992 |
| EP | 0640594 A1 | 3/1995 |
| EP | 0645387 A1 | 3/1995 |
| EP | 0847275 A1 | 6/1998 |
| EP | 0928789 A1 | 7/1999 |
| EP | 1156049 A1 | 11/2001 |
| EP | 1270724 A2 | 1/2003 |
| EP | 1801098 A1 | 6/2007 |
| EP | 1852425 A1 | 11/2007 |
| EP | 1864971 A1 | 12/2007 |
| EP | 1935420 A1 | 6/2008 |
| FR | 2796940 A1 | 2/2001 |
| GB | 1077711 A | 8/1967 |
| JP | 6092945 A | 4/1994 |
| JP | 7157681 A | 6/1995 |
| JP | 09151179 A | 6/1997 |
| JP | 2002179572 A | 6/2002 |
| JP | 2003096058 A | 4/2003 |
| JP | 2003300884 A | 10/2003 |
| JP | 2005-206503 A | 8/2005 |
| JP | 2005239670 A | 9/2005 |
| JP | 2005272321 A | 10/2005 |
| JP | 2007140188 A | 6/2007 |
| JP | 2007254409 A | 10/2007 |
| JP | 2009110842 A | 5/2009 |

(56) References Cited

FOREIGN PATENT DOCUMENTS

| | | |
|---|---|---|
| JP | 2011519374 A | 7/2011 |
| WO | 92/07838 A1 | 5/1992 |
| WO | 93/07128 A1 | 4/1993 |
| WO | 93/13103 A1 | 7/1993 |
| WO | 95/31440 A1 | 11/1995 |
| WO | 96/14297 A1 | 5/1996 |
| WO | 96/23787 A1 | 8/1996 |
| WO | 96/37494 A1 | 11/1996 |
| WO | 97/07789 A1 | 3/1997 |
| WO | 97/36605 A1 | 10/1997 |
| WO | 98/22462 A1 | 5/1998 |
| WO | 98/52940 A1 | 11/1998 |
| WO | 98/57940 A1 | 12/1998 |
| WO | 99/05125 A1 | 2/1999 |
| WO | 99/06395 A1 | 2/1999 |
| WO | 00/09107 A2 | 2/2000 |
| WO | 01/00595 A1 | 1/2001 |
| WO | 01/13917 A1 | 3/2001 |
| WO | 01/44200 A2 | 6/2001 |
| WO | 01/55063 A1 | 8/2001 |
| WO | 02/06244 A1 | 1/2002 |
| WO | 02/06277 A1 | 1/2002 |
| WO | 02/22572 A2 | 3/2002 |
| WO | 03/043988 A1 | 5/2003 |
| WO | 03/057673 A1 | 7/2003 |
| WO | 03/093261 A1 | 11/2003 |
| WO | 03/097608 A2 | 11/2003 |
| WO | 2004/004722 A1 | 1/2004 |
| WO | 2004/009559 A2 | 1/2004 |
| WO | 2004/014859 A2 | 2/2004 |
| WO | 2004/046137 A1 | 6/2004 |
| WO | 2004/056745 A2 | 7/2004 |
| WO | 2004/089896 A1 | 10/2004 |
| WO | 2004/094375 A2 | 11/2004 |
| WO | 2005/000845 A2 | 1/2005 |
| WO | 2005/086700 A2 | 9/2005 |
| WO | 2005/108360 A1 | 11/2005 |
| WO | 2005/108361 A1 | 11/2005 |
| WO | 2005/113525 A1 | 12/2005 |
| WO | 2005/116002 A2 | 12/2005 |
| WO | 2006/002349 A1 | 1/2006 |
| WO | 2006/003494 A2 | 1/2006 |
| WO | 2006/014357 A1 | 2/2006 |
| WO | 2006/017443 | 2/2006 |
| WO | 2006/024627 A2 | 3/2006 |
| WO | 2006/024628 A1 | 3/2006 |
| WO | 2006/031715 A2 | 3/2006 |
| WO | 2006/040329 A1 | 4/2006 |
| WO | 2006/044174 A2 | 4/2006 |
| WO | 2006/049952 A1 | 5/2006 |
| WO | 2006/066924 A2 | 6/2006 |
| WO | 2006/066948 A1 | 6/2006 |
| WO | 2006/090792 A1 | 8/2006 |
| WO | 2006/104280 A1 | 10/2006 |
| WO | 2006/109056 A1 | 10/2006 |
| WO | 2007/008529 A2 | 1/2007 |
| WO | 2007/022371 A2 | 2/2007 |
| WO | 2007/048595 A1 | 5/2007 |
| WO | 2007/051810 A2 | 5/2007 |
| WO | 2007/061661 A2 | 5/2007 |
| WO | 2007/068330 A1 | 6/2007 |
| WO | 2007/076055 A2 | 7/2007 |
| WO | 2007/079186 A2 | 7/2007 |
| WO | 2007/081569 A2 | 7/2007 |
| WO | 2007/081570 A2 | 7/2007 |
| WO | 2007/081571 A2 | 7/2007 |
| WO | 2007/084314 A2 | 7/2007 |
| WO | 2007/101270 A1 | 9/2007 |
| WO | 2007/103719 A2 | 9/2007 |
| WO | 2007/109456 A2 | 9/2007 |
| WO | 2007/118185 A2 | 10/2007 |
| WO | 2007/123853 A2 | 11/2007 |
| WO | 2007/124254 A2 | 11/2007 |
| WO | 2007/124329 A1 | 11/2007 |
| WO | 2007/124337 A1 | 11/2007 |
| WO | 2007/127693 A1 | 11/2007 |
| WO | 2007/127763 A2 | 11/2007 |
| WO | 2008/000951 A2 | 1/2008 |
| WO | 2008/024497 A2 | 2/2008 |
| WO | 2008/031227 A1 | 3/2008 |
| WO | 2008/036715 A1 | 3/2008 |
| WO | 2008/046578 A2 | 4/2008 |
| WO | 2008/046758 A2 | 4/2008 |
| WO | 2008/059948 A1 | 5/2008 |
| WO | 2008/106128 A2 | 9/2008 |
| WO | 2008/118332 A2 | 10/2008 |
| WO | 2009/017664 A1 | 2/2009 |
| WO | 2009/017671 A1 | 2/2009 |
| WO | 2009/020140 A1 | 2/2009 |
| WO | WO 2009/017664 A1 | 2/2009 |
| WO | WO 2009017664 A1 * | 2/2009 |
| WO | 2009/061498 A1 | 5/2009 |
| WO | 2009/063061 A2 | 5/2009 |
| WO | 2009/075835 A1 | 6/2009 |
| WO | 2009/088997 A1 | 7/2009 |
| WO | 2009/094169 A1 | 7/2009 |
| WO | 2009/100872 A1 | 8/2009 |
| WO | 2009/102428 A2 | 8/2009 |
| WO | 2009/102460 A2 | 8/2009 |
| WO | 2009/108332 A1 | 9/2009 |
| WO | 2009/117109 A1 | 9/2009 |
| WO | 2009/131669 A2 | 10/2009 |
| WO | 2009/134384 A1 | 11/2009 |
| WO | 2009/134387 A1 | 11/2009 |
| WO | 2009/134392 A1 | 11/2009 |
| WO | 2009/134400 A1 | 11/2009 |
| WO | 2009/138386 A2 | 11/2009 |
| WO | 2010/010149 A1 | 1/2010 |
| WO | 2010/010157 A2 | 1/2010 |
| WO | 2010/010174 A1 | 1/2010 |
| WO | 2010/011314 A1 | 1/2010 |
| WO | WO 2010/010150 A1 | 1/2010 |
| WO | 2010/023161 A1 | 3/2010 |
| WO | 2010/046445 A2 | 4/2010 |
| WO | 2010/089303 A1 | 8/2010 |
| WO | 2010/091067 A2 | 8/2010 |
| WO | 2010/104830 A1 | 9/2010 |
| WO | 2010/127237 A2 | 11/2010 |
| WO | 2010/139673 A1 | 12/2010 |
| WO | 2010/141424 A1 | 12/2010 |
| WO | 2011/002910 A1 | 1/2011 |
| WO | 2011/011123 A1 | 1/2011 |
| WO | 2011/031979 A1 | 3/2011 |
| WO | 2011/056737 A1 | 5/2011 |
| WO | 2011/057054 A1 | 5/2011 |
| WO | 2011/159760 A1 | 12/2011 |
| WO | 2011/161128 A1 | 12/2011 |
| WO | 2012/059416 A1 | 5/2012 |
| WO | 2012/061708 A1 | 5/2012 |

OTHER PUBLICATIONS

Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.

Gutkowska et al.: Acta Poloniae Pharmaceutica, 1982, vol. 39, p. 61-64.

Olesen et al.: Current Opin Drug Dis Dev, 2001, vol. 4, No. 4, p. 471-478.

Thornber et al.: Chem Soc Rev, 1979, vol. 8, p. 563-580.

Caplus-133:4656—Anantanarayan, A. el. al., "Preparation of heteroarylpyrazoles as P38 kinase inhibitors". 2000.

Caplus-147:134403, Hembrough, TA, et al., Composition and methods comprising proteinase activated receptor 2 antagonists for treatment of angiogenesis and inflammatory disorders and cancer. 2007.

Caplus-77:5360, Helsley, G. C. "Antispasmodic 8-carbamoyl-3-phenylnortropanes". 1972.

International Search Report and Written Opinion for PCT/US2012/050679 mailed Oct. 31, 2012.

International Search Report and Written Opinion for PCT/EP2009/059509, mailed Feb. 9, 2009.

Claremon et al. CAS: 150:214405, 2009.

(56) References Cited

OTHER PUBLICATIONS

Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.

Evans, B.E. et al., "Orally active, nonpeptide osytocin antagonists". Journal of Medicinal Chemistry, American Chem. Soc., Vo. 35, No. 21, Oct. 15, 1992, p. 3919-3927.

Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.

Aluri. B.R. et al., "Bulky n-Substituted 1,3-Benzazaphospholes: Access via Pd-Catalyzed C-N and C-P Cross Coupling, Lithiation, and Conversion to Novel P=C PtBu2 Hybrid Ligands". Inorganic Chemistry, 2008, 47, p. 6900-6912.

Aluri, B.R. et al., "Sterically and Polarity-Controlled Reactions of tBuLi with P=CH-NR Heterocycles: Novel Heterocyclic P-and P,O-Ligands and Preliminary Tests in Transition-Metal Catalysis", Chem. Eur. Journal, vol. 14, 2008, p. 4328-4335.

Fandrick, DR. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.

International Search Report and Written Opinion for PCT/EP/2009/059496 mailed Nov. 17, 2009.

International Search Report and Written Opinion for PCT/EP2010/051262 mailed Aug. 7, 2011.

International Search Report and Written Opinion for PCT/EP2011/060386 mailed Sep. 16, 2011.

International Search Report and Written Opinion for PCT/US2010/054912 mailed Mar. 16, 2011.

International Search Report for PCT/EP2011/068938 mailed Mar. 27, 2012.

Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.

Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.

Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.

Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.

Worthy, AD. et al., "Regioselective Hydroformylation of Sulfonamides using a Scaffolding Ligand". Organic Letters, 2009, vol. 11, No. 13—p. 2764-2767.

Kametani et al. Chem Pharma Bull, 1965 vol. 13, No. 3, p. 295-299.

Patani et al. Chem Rev, 1996 p. 3147-3176.

Stewart et al. Vitam Horm. 1999;57:249-324.

US 8,575,157, 11/2013, Renz et al. (withdrawn)

MS Bitar, "Glucocorticoid Dynamics and Impaired Wound Healing in Diabetes Mellitus", Am J Pathol., 1998, vol. 152, pp. 547-554.

MS Bitar, et al., "Heat-Shock Protein 72/73 and Impaired Wound Healing in Diabetic and Hypercortisolemic States", Sugery, 1999, vol. 125, pp. 594-601.

MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.

MS Bitar, "Insulin and Glucocorticoid-Dependent Suppression of the IGF-I System in Diabetic Wounds", Sugery, 2000, vol. 127, pp. 687-695.

Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CASRN: 20057-45-8 abstract, (1969).

Chimica Therapeutica, 1968, vol. 3(5), pp. 321-324, 1968.

Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract,(1978).

Zhurnal Organicheskoi Khimii, 1978, vol. 14(5), pp. 1092-1094.

"Khimiia Elementoorganicheskikh Soedineni", 1982, vol. 1982 pp. 22-26.

"Zhurnal Organicheskoi Khimii", 1982, vol. 18, PT 11, p. 2468.

Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.

Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.

Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.

Ho-Jane Shue et al., "Cyclic Urea Derivatives as Potent NK1 Selective Antagonists", Bioorganic & Medicinal Chemistry Letters, 2005, vol. 15, pp. 3896-3899.

Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.

Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.

Lohray et al., "Enantiospecific Synthesis of 6-Substituted N-Aryl-1,3-Oxazin-2-Ones", Tetrahedron Letters, 1998, vol. 39, pp. 6555-6556.

Malgorzata Wamil and Jonathan R. Seckl, "Inhibition of 11.beta.-hydroxysteroid Dehydrogenase Type 1 as a Promising Therapeutic Target", Drug Discovery Today, 2007, vol. 12, pp. 504-520.

Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.

Schoellkopf, et al., "Umsetzungen Alphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.

Suga, Seiji et al., ""N-Acyliminium Ion Pool" as a Heterodiene in [4+2] Cycloaddition Reaction", Organic Letters, 2003, vol. 5, pp. 945-947.

Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.

Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.

Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.

International Search Report & Written Opinion—(PCT/US2008/009017) Date of Mailing Apr. 12, 2008.

International Search Report & Written Opinion—(PCT/US2008/002517) Date of Mailing Dec. 29, 2008.

International Search Report—(PCT/US2009/002653) Date of Mailing Jul. 3, 2009.

International Search Report—(PCT/US2009/002641) Date of Mailing Jul. 3, 2009.

International Search Report—(PCT/US2009/002629) Date of Mailing Jul. 3, 2009.

International Search Report—(PCT/US2009/002633) Date of Mailing Jul. 3, 2009.

(56) References Cited

OTHER PUBLICATIONS

International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
International Search Report and Written Opinion, International Application No. PCT/US2011/040443, International Filing Date: Jun. 15, 2011, mailed Nov. 11, 2011, 15 pages.
De Luis, et al., "Control of Metabolic Syndrome with Metformin in Obese Type 2 Diabetes Mellitus Patients, Diabetes Research and Clinical Practice," 2000, vol. 50, Suppl. 1, pp. S51-S52.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.
International Search Report—(PCT/US2010/023021) Date of Mailing Aug. 5, 2010.
International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
Gavezzotti, "Are Crystal Structures Predictable?", Accounts of Chemical Research, 1994, vol. 27, pp. 309-314.
Vippagunta, et al., "Crystalline Solids", Advanced Drug Deliver Reviews, 2001, vol. 48, pp. 3-26.
CA 1267843-31-1, (Aug. 10, 2009).
Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1968).
Tamaru et al., "Urea as the Most Reactive and Versatile Nitrogen Nucleophile for the Palladium(2+)-Catalized Cyclization of Unsaturated Amines", Journal of the American Chemical Society, 1988, vol. 110, pp. 3994-4002.
Office Action for U.S. Appl. No. 12/741,522 (U.S. Patent No. 8,138,178), date of mailing Dec. 15, 2010.
CA 154:284276, (Mar. 17, 2011).
Office Action dated Apr. 3, 2012 for corresponding U.S. Appl. No. 13/318,271.
Office Action for U.S. Appl. No. 12/741,532 (US Patent No. 8,114,868), date of mailing Dec. 15, 2010.
Office Action for U.S. Appl. No. 12/771,499, date of mailing Dec. 21, 2010.
Wolfling, Janos et al., "Neighboring Group Participation Part 15. Stereoselective Synthesis of Some Steroidal Tetrahydrooxaziin-2-ones, as Novel Presumed Inhibitors of Human 5?-Reductase," Steroids, 69: 451-460 (2004).
Office Action dated May 3, 2012 for corresponding U.S. Appl. No. 13/347,799.
Office Action dated Jun. 14, 2012 for corresponding U.S. Appl. No. 13/347,784.
Chemical Abstracts, Registry No. 351443-37-3 (Available on Aug. 15, 2001.).
Souillac et al., Characterization of Delivery Systems, Differential Scanning Calorimetry, pp. 217-218 (in Encyclopedia of Controlled Drug Delivery, 1999, John Wiley & Sons, pp. 212-227).
Morissette et al. Advanced Drug Deliery Reviews 2004, 56, 275-300.
Database CA [Online], Chemical Abstracts Service, Fukushima et al., "Preparation of Imidazolidinone Derivatives as 11.beta.-HSD1 Inhibitors", 2007, XP 002531878.
Examiner Interview Summary dated May 2, 2011, in U.S. Appl. No. 12/741,522 (U.S. Patent No. 8,138,178).
Chalmers (TIPS vol. 17, pp. 166-172 Apr. 1996).
Anderson, (Chem and Biol 10:787-797, 2003).
Thiel (Nature Biotechnol 2:513-519, 2004).
International Search Report for PCT/EP2009/063913 mailed May 6, 2010.
Gutkowska et al.: Acta Poloniae Pharmaceutica 1986, 43, p. 403-405.
Gutkowska et al.: Acta Polonaie Pharmaceutica 1987, 39, p. 411-414.
DeMarinis R.M. et.al. Journal of Medicinal Chemistry 1981, vol. 24, No. 12, pp. 1432-1437.
Rosenstock et.al. Diabetes Care Jul. 2010, LNKDPUBMED: 20413513, vol. 33, No. 7, pp. 1516-1522.
Vidic et al.: Chem. Ber. 1976, 109, p. 2657-2669.

* cited by examiner

CYCLIC INHIBITORS OF 11β-HYDROXYSTEROID DEHYDROGENASE 1 BASED ON THE 1,3-OXAZINAN-2-ONE STRUCTURE

RELATED APPLICATIONS

This application is a 35 U.S.C. §371 national stage filing of International Application No. PCT/US2010/038191, filed Jun. 10, 2010, which claims priority from U.S. Provisional Application No. 61/186,159, filed Jun. 11, 2009. The entire teachings of each of the aforementioned applications are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9).

Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, N.Y.), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043,951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula (I) or pharmaceutically acceptable salts thereof, are effective inhibitors of 11β-HSD1.

The present invention is directed to compounds represented by the Structural Formula (I):

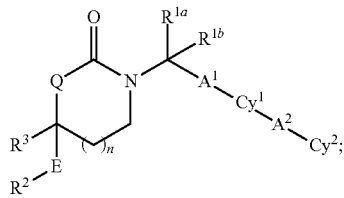

(I)

or a pharmaceutically acceptable salt, enantiomer or diastereomer thereof.

$R^{1a}$ and $R^{1b}$ are independently hydrogen, $(C_1-C_6)$alkyl, $(C_2-C_6)$alkenyl, $(C_2-C_6)$alkynyl or $(C_1-C_3)$alkoxy$(C_1-C_3)$ alkyl, or $R^{1a}$ and $R^{1b}$ taken together with the carbon to which they are attached form a $(C_3-C_6)$cycloalkyl ring; provided that both $R^{1a}$ and $R^{1b}$ are not hydrogen and if $R^{1a}$ or $R^{1b}$ is hydrogen then $A^1$ is ethynyl; wherein the $(C_1-C_6)$alkyl, $(C_2-C_6)$alkenyl, $(C_2-C_6)$alkynyl, $(C_1-C_3)$alkoxy$(C_1-C_3)$alkyl, or the cycloalkyl ring formed from $R^{1a}$ and $R^{1b}$ and the carbon to which $R^{1a}$ and $R^{1b}$ are attached are, independently, optionally substituted with up to four groups independently selected from fluorine, cyano, oxo, H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclyl, heteroaryl, aryl-amino and heteroarylamino.

$A^1$ is (a) a bond, (b) $(C_1-C_2)$alkylene, $CH_2O$ with the oxygen being attached to $Cy^1$ or $C(=O)$, or (c) ethynyl.

$Cy^1$ is aryl, heteroaryl, monocyclic cycloalkyl or monocyclic heterocyclyl and is optionally substituted with 1 to 4 groups independently selected from halogen, $-CN$, $-NO_2$, $-NH_2$, $-OH$, $-COOH$, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $-R^9$, $(C_1-C_6)$alkylthio, $(C_3-C_6)$cycloalkythio, $-SR^9$, $-S(=O)R^6$, $-S(=O)R^7$, $-S(=O)R^9$, $-S(=O)_2R^6$, $-S(=O)_2R^7$, $-S(=O)_2R^9$, $-NHR^6$, $-N(R^6)$, $-C(=O)R^6$, $-C(=O)NH_2$, $-S(=O)_2NH_2$, $-C(=O)NHR^6$, $-C(=O)NR^6R^6$, $-C(=O)R^8$, $-S(=O)_2NHR^6$, $-S(=O)_2N(R^6)_2$, $-S(=O)_2R^8$, $-NHC(=O)R^6$, $-V^1-NHC(=O)R^6$, $-NHS(=O)_2R^6$, $-V^1-NHS(=O)_2R^6$, $-V^1-C(=O)R^6$, heteroaryl, aryl, heterocyclyl, oxo, $-V^1-NH2$, $-V^1-NHR^6$, $-V^1-N(R^6)_2$, $-C(=O)R^7$, $-C(=O)NHR^7$, $-C(=O)NR^6R^7$, $-C(=O)N(R^7)_2$, $-S(=O)_2NHR^7$, $-S(=O)_2NR^6R^7$, $-S(=O)_2N(R^7)_2$, cyano$(C_1-C_6)$alkyl, $-V^1-C(=O)NH_2$, $-V^1-C(=O)NHR^6$, $-V^1-C(=O)N(R^6)_2$, $-V^1-C(=O)NHR^7$, $-V^1-C(=O)NR^6R^7$ and $-V^1-C(=O)N(R)_2$;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo.

$Cy^2$ is hydrogen, aryl, heteroaryl, cycloalkyl or heterocyclyl and is optionally substituted with 1 to 4 groups independently selected from halogen, $-CN$, $-NO_2$, $-NH_2$, $-OH$, $-COOH$, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $-R^9$, $(C_1-C_6)$alkylthio, $(C_3-C_6)$cycloalkythio, $-SR^9$, $-S(=O)R^6$, $-S(=O)R^7$, $-S(=O)R^9$, $-S(=O)_2R^6$, $-S(=O)_2R^7$, $-S(=O)_2R^9$, $-NHR^6$, $-N(R^6)$, $-C(=O)R^6$, $-C(=O)NH_2$, $-S(=O)_2NH_2$, $-C(=O)NHR^6$, $-C(=O)NR^6R^6$, $-C(=O)R^8$, $-S(=O)_2NHR^6$, $-S(=O)_2N(R^6)_2$, $-S(=O)_2R^8$, $-NHC(=O)R^6$, $-V^1-NHC(=O)R^6$, $-NHS(=O)_2R^6$, $-V^1-NHS(=O)_2R^6$, $-V^1-C(=O)R^6$, heteroaryl, aryl, heterocyclyl, oxo, $-V^1-NH2$, $-V^1-NHR^6$, $-V^1-N(R^6)_2$, $-C(=O)R^7$, $-C(=O)NHR^7$, $-C(=O)NR^6R^7$, $-C(=O)N(R^7)_2$, $-S(=O)_2NHR^7$, $-S(=O)_2NR^6R^7$, $-S(=O)_2N(R^7)_2$, cyano$(C_1-C_6)$alkyl, $-V^1-C(=O)NH_2$, $-V^1-C(=O)NHR^6$, $-V^1-C(=O)N(R^6)_2$, $-V^1-C(=O)NHR^7$, $-V^1-C(=O)NR^6R^7$ and $-V^1-C(=O)N(R^7)_2$.

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected halogen, $-CN$, $-NO_2$, $-NH_2$, $-OH$, $-COOH$, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $-R^9$, $(C_1-C_6)$alkylthio, $(C_3-C_6)$cycloalkythio, $-SR^9$, $-S(=O)R^6$, $-S(=O)R^7$, $-S(=O)R^9$, $-S(=O)_2R^6$, $-S(=O)_2R^7$, $-S(=O)_2R^9$, $-NHR^6$, $-N(R^6)$, $-C(=O)R^6$, $-C(=O)NH_2$, $-S(=O)_2NH_2$, $-C(=O)NHR^6$, $-C(=O)NR^6R^6$, $-C(=O)R^8$, $-S(=O)_2NHR^6$, $-S(=O)_2N(R^6)_2$, $-S(=O)_2R^8$, $-NHC(=O)R^6$, $-V^1-NHC(=O)R^6$, $-NHS(=O)_2R^6$, $-V^1-NHS(=O)_2R^6$, $-V^1-C(=O)R^6$, heteroaryl, aryl, heterocyclyl, oxo, $-V^1-NH2$, $-V^1-NHR^6$, $-V^1-N(R^6)_2$, $-C(=O)R^7$, $-C(=O)NHR^7$, $-C(=O)NR^6R^7$, $-C(=O)N(R^7)_2$, $-S(=O)_2NHR^7$, $-S(=O)_2NR^6R^7$, $-S(=O)_2N(R^7)_2$, cyano$(C_1-C_6)$alkyl, $-V^1-C(=O)NH_2$, $-V^1-C(=O)NHR^6$, $-V^1-C(=O)N(R^6)_2$, $-V^1-C(=O)NHR^7$, $-V^1-C(=O)NR^6R^7$ and $-V^1-C(=O)N(R^7)_2$.

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from $-F$, $-CN$, oxo, $-R^4$, $R^4O-$, $(R^4)_2N-$, $R^4O_2C-$, $R^4C(=O)O-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)$ NHS(=O)₂O—, R⁴OC(=O)NHS(=O)₂NR⁴—, (R⁴)2NC(=O)NHS(=O)₂—, (R⁴)₂NC(=O)NHS(=O)₂O—, (R⁴)₂NC(=O)NHS(=O)₂NR⁴—, spirocycloalkyl; heterocyclyl (which in turn is optionally substituted with alkyl, haloalkyl, halogen or oxo), heteroaryl (which in turn is optionally substituted with alkyl, haloalkyl, alkoxy, alkylthio, alkylsulfonyl, halogen, trifluoromethyl, dialkylamino, nitro, cyano, CO₂H, CONH₂, N-monoalkyl-substituted amido, N,N-dialkyl-substituted amido, or oxo), aryl-amino (which in turn is optionally substituted with alkyl, alkoxy, alkylthio, alkylsulfonyl, halogen, trifluoromethyl, dialkylamino, nitro, cyano, CO₂H, CONH₂, N-monoalkyl-substituted amido and N,N-dialkyl-substituted amido) and heteroarylamino (which in turn is optionally substituted with alkyl, haloalkyl, alkoxy, alkylthio, alkylsulfonyl, halogen, trifluoromethyl, dialkylamino, nitro, cyano, CO₂H, CONH₂, N-monoalkyl-substituted amido, N,N-dialkyl-substituted amido, or oxo).

n is 0, 1 or 2.

Q is O, CH₂ or NR⁵.

Each R⁴ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl.

Each R⁵ is independently H, $(C_1-C_6)$alkyl, halo$(C_1-C_6)$alkyl or hydroxy$(C_1-C_6)$alkyl.

Each R⁶ is independently $(C_1-C_6)$alkyl, $(C_2-C_6)$alkenyl, $(C_2-C_6)$alkynyl or $(C_1-C_6)$alkoxy.

V¹ is $(C_1-C_6)$alkylene, $(C_1-C_6)$alkenylene, $(C_1-C_6)$alkynylene or $(C_1-C_6)$alkyleneoxy.

Each R⁷ is independently $(C_3-C_6)$cycloalkyl or $(C_3-C_6)$cycloalkoxy;

R⁸ is heterocyclyl.

R⁹ is $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl or halo$(C_1-C_6)$alkoxy$(C_1-C_6)$alkyl.

Another embodiment of the invention is a pharmaceutical composition comprising i) a pharmaceutically acceptable carrier or diluent, and ii) a compound of Formulas (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of an 11β-HSD1 inhibitor disclosed herein.

Another embodiment of the invention is the use of a compound of an 11β-HSD1 inhibitor disclosed herein for the manufacture of a medicament for inhibiting 11β-HSD1 activity in a mammal in need of such treatment.

Another embodiment of the invention is the use of an 11β-HSD1 inhibitor disclosed herein for the manufacture of a medicament for treating a subject with a disease associated with the activity or expression of 11β-HSD1.

Another embodiment of the invention is an 11β-HSD1 disclosed herein for use in inhibiting 11β-HSD1 activity in a mammal in need of such treatment.

Another embodiment of the invention is an 11β-HSD1 inhibitor disclosed herein for use in for treating a subject with a disease associated with the activity or expression of 11β-HSD1.

DETAILED DESCRIPTION OF THE INVENTION

The present invention is directed to compounds represented by the Structural Formula (I) or a pharmaceutically acceptable salt, enantiomer or diastereomer thereof. Values and particular values for the variables in Structural Formula I or an enantiomer, a diastereomer, or a pharmaceutically acceptable salt thereof are provided in the following paragraphs. It is understood that the invention encompasses all combinations of the substituent variables (i.e., Cy¹, R2, R3, etc.) defined herein. For Structural Formula (I):

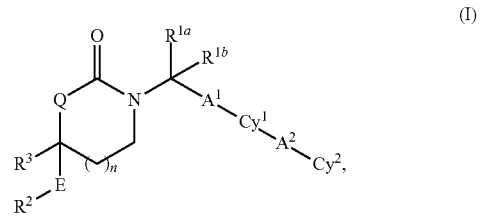

or a pharmaceutically acceptable salt, enantiomer or diastereomer thereof:

R$^{1a}$ and R$^{1b}$ are independently hydrogen, $(C_1-C_6)$alkyl, $(C_2-C_6)$alkenyl, $(C_2-C_6)$alkynyl or $(C_1-C_3)$alkoxy$(C_1-C_3)$alkyl, or R$^{1a}$ and R$^{1b}$ taken together with the carbon to which they are attached form a $(C_3-C_6)$cycloalkyl ring; provided that both R$^{1a}$ and R$^{1b}$ are not hydrogen and if R$^{1a}$ or R$^{1b}$ is hydrogen then A¹ is ethynyl; wherein the $(C_1-C_6)$alkyl, $(C_2-C_6)$alkenyl, $(C_2-C_6)$alkynyl, $(C_1-C_3)$alkoxy$(C_1-C_3)$alkyl, or the cycloalkyl ring formed from R$^{1a}$ and R$^{1b}$ and the carbon to which R$^{1a}$ and R$^{1b}$ are attached are, independently, optionally substituted with up to four groups independently selected from fluorine, cyano, oxo, H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, R⁴O—, (R⁴)₂N—, R⁴O₂C—, R⁴S, R⁴S(=O)—, R⁴S(=O)₂—, R⁴C(=O)NR⁴—, (R⁴)₂NC(=O)—, (R⁴)₂NC(=O)O—, (R⁴)₂NC(=O)NR⁴—, R⁴OC(=O)NR⁴—, (R⁴)₂NC(=NCN)NR⁴—, (R⁴O)₂P(=O)O—, (R⁴O)₂P(=O)NR⁴—, R⁴OS(=O)₂NR⁴—, (R⁴)₂NS(=O)₂O—, (R⁴)₂NS(=O)₂NR⁴—, R⁴S(=O)₂NR⁴—, R⁴S(=O)₂NHC(=O)—, R⁴S(=O)₂NHC(=O)O—, R⁴S(=O)₂NHC(=O)NR⁴—, R⁴OS(=O)₂NHC(=O)—, R⁴OS(=O)₂NHC(=O)O—, R⁴OS(=O)₂NHC(=O)NR⁴—, (R⁴)₂NS(=O)₂NHC(=O)—, (R⁴)₂NS(=O)₂NHC(=O)O—, (R⁴)₂NS(=O)₂NHC(=O)NR⁴—, R⁴C(=O)NHS(=O)₂—, R⁴C(=O)NHS(=O)₂O—, R⁴C(=O)NHS(=O)₂NR⁴, R⁴OC(=O)NHS(=O)₂—, R⁴OC(=O)NHS(=O)₂O—, R⁴OC(=O)NHS(=O)₂NR⁴—, (R⁴)₂NC(=O)NHS(=O)₂—, (R⁴)₂NC(=O)NHS(=O)₂O—, (R⁴)₂NC(=O)NHS(=O)₂NR⁴—, heterocyclyl, heteroaryl, aryl-amino and heteroarylamino.

In one particular embodiment, R$^{1a}$ and R$^{1b}$ are, independently, optionally substituted $(C_1-C_6)$alkyl.

In a more particular embodiment, R$^{1a}$ and R$^{1b}$ are, independently, optionally substituted methyl or ethyl.

In an even more particular embodiment, $R^{1a}$ and $R^{1b}$ are, independently, optionally substituted methyl.

In another particular embodiment, $R^{1a}$ and $R^{1b}$ are ($C_1$-$C_6$) alkyl, the groups represented by $R^{1a}$ and $R^{1b}$, independently, optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In a more particular embodiment, $R^{1a}$ and $R^{1b}$ are methyl or ethyl, the groups represented by $R^{1a}$ and $R^{1b}$, independently, optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In an even more particular embodiment, $R^{1a}$ and $R^{1b}$ are methyl, independently, optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In another particular embodiment, $R^{1a}$ and $R^{1b}$ are unsubstituted methyl.

In another particular embodiment, $R^{1a}$ and $R^{1b}$ taken together with the carbon to which they are attached form an optionally substituted ($C_3$-$C_6$)cycloalkyl ring.

In another particular embodiment, $R^{1a}$ and $R^{1b}$ taken together with the carbon to which they are attached form an ($C_3$-$C_6$)cycloalkyl ring optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In a more particular embodiment, $R^{1a}$ and $R^{1b}$ taken together with the carbon to which they are attached form an unsubstituted ($C_3$-$C_6$)cycloalkyl ring.

In another particular embodiment, $R^{1a}$ and $R^{1b}$ taken together with the carbon to which they are attached form a cyclopropyl ring optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In a more particular embodiment, $R^{1a}$ and $R^{1b}$ taken together with the carbon to which they are attached form an unsubstituted cyclopropyl ring.

In another particular embodiment, $R^{1a}$ and $R^{1b}$ are, independently, hydrogen, optionally substituted methyl or optionally substituted ethyl, or $R^{1a}$ and $R^{1b}$ taken together with the carbon to which they are attached form an optionally substituted cyclopropyl group; provided that both $R^{1a}$ and $R^{1b}$ are not hydrogen and if $R^{1a}$ or $R^{1b}$ is hydrogen then $A^1$ is ethynyl.

In a more particular embodiment, $R^{1a}$ and $R^{1b}$ are, independently, hydrogen or methyl, or $R^{1a}$ and $R^{1b}$ taken together with the carbon to which they are attached form cyclopropyl.

In another more particular embodiment, $R^{1a}$ and $R^{1b}$ are, independently, hydrogen, optionally substituted methyl or optionally substituted ethyl, or $R^{1a}$ and $R^{1b}$ taken together with the carbon to which they are attached form an optionally substituted cyclopropyl group; and the groups represented by $R^{1a}$ and $R^{1b}$ are, independently, optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—; provided that both $R^{1a}$ and $R^{1b}$ are not hydrogen and if $R^{1a}$ or $R^{1b}$ is hydrogen then $A^1$ is ethynyl.

$A^1$ is (a) a bond, (b) ($C_1$-$C_2$)alkylene, $CH_2O$ with the oxygen being attached to $Cy^1$ or $C(=O)$, or (c) ethynyl;

In one particular embodiment, $A^1$ is a bond.

In another particular embodiment, $A^1$ is a ($C_1$-$C_2$)alkylene.

In another particular embodiment, $A^1$ is a ethynyl.

$Cy^1$ is aryl, heteroaryl, monocyclic cycloalkyl or monocyclic heterocyclyl and is optionally substituted with 1 to 4 groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, —$R^9$, ($C_1$-$C_6$)alkylthio, ($C_3$-$C_6$)cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano($C_1$-$C_6$)alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$.

In one particular embodiment, $Cy^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxohexahydro-1,2-thiazinyl, cyclohexyl or cyclopropyl group In a more particular embodiment, $Cy^1$ is an optionally substituted cyclohexyl, phenyl, pyridyl, pyrimidinyl, thiazolyl, triazolyl, benzothiazolyl or oxodihydropyridyl group.

In an even more particular embodiment, $Cy^1$ is optionally substituted phenyl or triazolyl group.

In another more particular embodiment, $Cy^1$ is an optionally substituted phenyl or oxodihydroquinolinyl group.

In an even more particular embodiment, $Cy^1$ is optionally substituted phenyl. In another particular embodiment, the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, 2-hydroxyethyl, 2-hydroxy-2-propyl, methoxymethyl, methylsulfonyl, methylsulfonylamino, benzyloxycarbonyl, ethyl, propyl, cyclopropyl, halo, hydroxymethyl, methoxycarbonyl, amino, aminomethyl, carbamoyl, methylcarbamoyl, dimethylcarbamoyl, (2-methoxyethyl)

aminocarbonyl, acetylaminomethyl, methylaminosulfonyl, isopropylaminosulfonyl, dimethylaminosulfonyl, pyrrolidine-1-sulfonyl, methylsulfonylaminomethyl, tetrazolyl, acetyl, 1-aminoethyl, deuteromethyl, t-butyl, difluoromethyl, 2-fluoroethyl, 2,2,2-trifluoroethyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In a more particular embodiment, the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, the group represented by $Cy^1$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another particular embodiment, $Cy^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, 2-hydroxyethyl, 2-hydroxy-2-propyl, methoxymethyl, methylsulfonyl, methylsulfonylamino, benzyloxycarbonyl, ethyl, propyl, cyclopropyl, halo, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylaminosulfonyl, isopropylaminosulfonyl, dimethylaminosulfonyl, pyrrolidine-1-sulfonyl, methylsulfonyl-aminomethyl, tetrazolyl, acetyl, 1-aminoethyl, deuteromethyl, t-butyl, difluoromethyl, 2-fluoroethyl, 2,2,2-trifluoroethyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In a more particular embodiment, $Cy^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, $Cy^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and the group represented by $Cy^1$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another particular embodiment, $Cy^1$ is an optionally substituted cyclohexyl, phenyl, pyridyl, pyrimidinyl, thiazolyl, triazolyl or benzothiazolyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, 2-hydroxyethyl, 2-hydroxy-2-propyl, methoxymethyl, methylsulfonyl, methylsulfonylamino, benzyloxycarbonyl, ethyl, propyl, cyclopropyl, halo, hydroxymethyl, methoxycarbonyl, amino, aminomethyl, carbamoyl, methyl-carbamoyl, dimethylcarbamoyl, (2-methoxyethyl)aminocarbonyl, acetylaminomethyl, methylaminosulfonyl, isopropylaminosulfonyl, dimethylamino-sulfonyl, pyrrolidine-1-sulfonyl, methylsulfonylaminomethyl, tetrazolyl, acetyl, 1-aminoethyl, deuteromethyl, t-butyl, difluoromethyl, 2-fluoroethyl, 2,2,2-trifluoroethyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In a more particular embodiment, $Cy^1$ is an optionally substituted cyclohexyl, phenyl, pyridyl, pyrimidinyl, thiazolyl, triazolyl or benzothiazolyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, $Cy^1$ is an optionally substituted cyclohexyl, phenyl, pyridyl, pyrimidinyl, thiazolyl, triazolyl or benzothiazolyl group, and the group represented by $Cy^1$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another particular embodiment, $Cy^1$ is optionally substituted phenyl or triazolyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, 2-hydroxyethyl, 2-hydroxy-2-propyl, methoxymethyl, methylsulfonyl, methylsulfonylamino, benzyloxycarbonyl, ethyl, propyl, cyclopropyl, halo, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylaminosulfonyl, isopropylaminosulfonyl, dimethylamino-sulfonyl, pyrrolidine-1-sulfonyl, methylsulfonyl-aminomethyl, tetrazolyl, acetyl, 1-aminoethyl, deuteromethyl, t-butyl, difluoromethyl, 2-fluoroethyl, 2,2,2-trifluoroethyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In a more particular embodiment, $Cy^1$ is optionally substituted phenyl or triazolyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, $Cy^1$ is optionally substituted phenyl or triazolyl group, and the group represented by $Cy^1$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another particular embodiment, $Cy^1$ is an optionally substituted phenyl or oxodihydroquinolinyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, 2-hydroxyethyl, 2-hydroxy-2-propyl, methoxymethyl, methylsulfonyl, methylsulfonylamino, benzyloxycarbonyl, ethyl, propyl, cyclopropyl, halo, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylaminosulfonyl, isopropylaminosulfonyl, dimethylaminosulfonyl, pyrrolidine-1-sulfonyl, methylsulfonylaminomethyl, tetrazolyl, acetyl, 1-aminoethyl, deuteromethyl, t-butyl, difluoromethyl, 2-fluoroethyl, 2,2,2-trifluoroethyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In a more particular embodiment, $Cy^1$ is an optionally substituted phenyl or oxodihydroquinolinyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, $Cy^1$ is an optionally substituted phenyl or oxodihydroquinolinyl group, and the group represented by $Cy^1$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another particular embodiment, $Cy^1$ is an optionally substituted phenyl, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, 2-hydroxyethyl, 2-hydroxy-2-propyl, methoxymethyl, methylsulfonyl, methylsulfonylamino, benzyloxycarbonyl, ethyl, propyl, cyclopropyl, halo, hydroxymethyl, methoxycarbonyl, amino, aminomethyl, carbamoyl, methyl-carbamoyl, dimethylcarbamoyl, (2-methoxyethyl)aminocarbonyl, acetylaminomethyl, methylaminosulfonyl, isopropylaminosulfonyl, dimethylamino-sulfonyl, pyrrolidine-1-sulfonyl, methylsulfonylaminomethyl, tetrazolyl, acetyl, 1-aminoethyl, deuteromethyl, t-butyl, difluoromethyl, 2-fluoroethyl, 2,2,2-trifluoroethyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In a more particular embodiment, $Cy^1$ is an optionally substituted phenyl, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, $Cy^1$ is an optionally substituted phenyl, and the group represented by $Cy^1$ is optionally substituted with fluoro, chloro, cyano, $CONH_2$, CONHMe, CONMe$_2$, CONHc-Pr, methyl, ethyl, cyclopropyl, difluoromethyl, CF$_3$ or oxo.

In another particular embodiment, Cy$^1$ is phenyl optionally substituted with fluoro, chloro, or methyl.

In an even more particular embodiment, Cy$^1$ is phenyl.

A$^2$ is (a) a bond, O, S or NR$^4$; or (b) (C$_1$-C$_3$)alkylene or (C$_1$-C$_2$)alkyleneoxy, each of which is optionally substituted with 1 to 4 groups independently selected from methyl, ethyl, trifluoromethyl or oxo.

In one particular embodiment, A$^2$ is a bond.

In another particular embodiment, A$^2$ is (C$_1$-C$_3$)alkylene or (C$_1$-C$_2$)alkyleneoxy, each of which is optionally substituted with 1 to 4 groups independently selected from methyl, ethyl, trifluoromethyl or oxo.

In a more particular embodiment, A$^2$ is (C$_1$-C$_3$)alkylene optionally substituted with 1 to 4 groups independently selected from methyl, ethyl, trifluoromethyl or oxo.

In an even more particular embodiment, A$^2$ is unsubstituted (C$_1$-C$_3$)alkylene.

Cy$^2$ is hydrogen, aryl, heteroaryl, cycloalkyl or heterocyclyl and is optionally substituted with 1 to 4 groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy (C$_2$-C$_6$)alkenyl, hydroxy(C$_1$-C$_6$)alkoxy, —R$^9$, (C$_1$-C$_6$)alkylthio, (C$_3$-C$_6$)cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$)$_2$, —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O) R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O) N(R$^6$)$_2$, —V$^1$—C(=O)NHR$^7$, —V$^1$—C(=O)NR$^6$R$^7$ and —V$^1$—C(=O)N(R)$_2$.

In one particular embodiment, Cy$^2$ is hydrogen, aryl, heteroaryl, cycloalkyl or heterocyclyl and is optionally substituted with 1 to 4 groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl, hydroxy(C$_1$-C$_6$)alkoxy, —R$^9$, (C$_1$-C$_6$)alkylthio, (C$_3$-C$_6$)cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$)$_2$, —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$; provided that Cy$^2$ is an optionally substituted aryl, heteroaryl, cycloalkyl or heterocyclyl group if R$^{1a}$ and R$^{1b}$ taken together with the carbon to which they are attached form an optionally substituted (C$_3$-C$_6$)cycloalkyl ring.

In a further particular embodiment, Cy$^2$ is an optionally substituted aryl, heteroaryl, cycloalkyl or heterocyclyl group.

In a more particular embodiment, Cy$^2$ is an optionally substituted aryl, heteroaryl, cycloalkyl or heterocyclyl group, and the group represented by Cy$^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, carbamoyl, methylcarbamoyl, dimethylcarbamoyl, (2-methoxyethyl) aminocarbonyl, acetylaminomethyl, methylsulfonyl, methylsulfonylamino, methylaminosulfonyl, isopropylaminosulfonyl, dimethyl-amino-sulfonyl, pyrrolidine-1-sulfonyl, methylsulfonylaminomethyl, tetrazolyl, trifluoromethyl, acetyl, 2-hydroxyethyl, 1-aminoethyl, deuteromethyl, t-butyl, difluoromethyl, 2-fluoroethyl, 2,2,2-trifluoroethyl, 2-hydroxy-2-propyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In another particular embodiment, Cy$^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group.

In a more particular embodiment, Cy$^2$ is an optionally substituted phenyl or oxodihydropyridyl group.

In an even more particular embodiment, Cy$^2$ is an optionally substituted phenyl.

In yet an even more particular embodiment, Cy$^2$ is phenyl.

In another more particular embodiment, Cy$^2$ is optionally substituted oxodihydropyridyl.

In another more particular embodiment, Cy$^2$ is oxodihydropyridyl.

In another particular embodiment, Cy$^2$ is hydrogen.

In another particular embodiment, Cy$^2$ is optionally substituted with one to four groups independently selected from (C$_1$-C$_6$)alkyl and (C$_3$-C$_6$)cycloalkyl.

In another particular embodiment, Cy$^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethyl-amino-sulfonyl, pyrrolidine-1-sulfonyl, methylsulfonylaminomethyl, tetrazolyl, trifluoromethyl, acetyl, 2-hydroxyethyl, 1-aminoethyl, deuteromethyl, t-butyl, difluoromethyl, 2-fluoroethyl, 2,2,2-trifluoroethyl, 2-hydroxy-2-propyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In another particular embodiment, the group represented by $Cy^2$ is optionally substituted with one to four groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl and hydroxy(C$_1$-C$_6$)alkoxy;

In yet another particular embodiment, the group represented by $Cy^2$ is optionally substituted with fluoro, chloro, cyano, CONH$_2$, CONHMe, CONMe$_2$, CONHc-Pr, methyl, ethyl, cyclopropyl, difluoromethyl, CF$_3$ or oxo.

In another particular embodiment, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethyl-amino-sulfonyl, pyrrolidine-1-sulfonyl, methylsulfonylaminomethyl, tetrazolyl, trifluoromethyl, acetyl, 2-hydroxyethyl, 1-aminoethyl, deuteromethyl, t-butyl, difluoromethyl, 2-fluoroethyl, 2,2,2-trifluoroethyl, 2-hydroxy-2-propyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

In a more particular embodiment, $Cy^2$ is an optionally substituted phenyl or oxodihydropyridyl group, and the group represented by $Cy^2$ is optionally substituted with one to four groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl and hydroxy(C$_1$-C$_6$)alkoxy.

In a more particular embodiment, $Cy^2$ is an optionally substituted phenyl or oxodihydropyridyl group, and the group represented by $Cy^2$ is optionally substituted with fluoro, chloro, cyano, CONH$_2$, CONHMe, CONMe$_2$, CONHc-Pr, methyl, ethyl, cyclopropyl, difluoromethyl, CF$_3$ or oxo.

In another particular embodiment, $Cy^2$ is an optionally substituted phenyl, and the group represented by $Cy^2$ is optionally substituted with one to four groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl and hydroxy(C$_1$-C$_6$)alkoxy.

In a more particular embodiment, $Cy^2$ is an optionally substituted phenyl, and the group represented by $Cy^2$ is optionally substituted with fluoro, chloro, cyano, CONH$_2$, CONHMe, CONMe$_2$, CONHc-Pr, methyl, ethyl, cyclopropyl, difluoromethyl, OF$_3$ or oxo.

In another particular embodiment, $Cy^2$ is an optionally substituted oxodihydropyridyl group, and the group represented by $Cy^2$ is optionally substituted with one to four groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl and hydroxy(C$_1$-C$_6$)alkoxy.

In a more particular embodiment, $Cy^2$ is an optionally substituted oxodihydropyridyl group, and the group represented by $Cy^2$ is optionally substituted with fluoro, chloro, cyano, CONH$_2$, CONHMe, CONMe$_2$, CONHc-Pr, methyl, ethyl, cyclopropyl, difluoromethyl, CF$_3$ or oxo.

In another more particular embodiment, $Cy^2$ is an optionally substituted oxodihydropyridyl group, and the group represented by $Cy^2$ is optionally substituted with (C$_1$-C$_6$)alkyl, halo(C$_1$-C$_6$)alkyl or (C$_3$-C$_6$)cycloalkyl.

In another particular embodiment, $Cy^2$ is oxodihydropyridyl optionally substituted with fluoro, chloro, bromo, cyano, CONH$_2$, CONHMe, CONMe$_2$, methyl, ethyl, cyclopropyl, CHF$_2$, CHF$_2$CH$_2$ or OF$_3$.

In another particular embodiment, $Cy^2$ is oxodihydropyridyl optionally substituted at the ring nitrogen with methyl, ethyl, propyl, cyclopropyl, difluoromethyl, 2-fluoroethyl or 2,2,2-trifluoroethyl.

In another particular embodiment, $Cy^2$ is oxodihydropyridyl optionally substituted at the ring nitrogen with methyl, ethyl, propyl or cyclopropyl.

E is (a) a bond or (b) (C$_1$-C$_3$)alkylene or (C$_1$-C$_2$)alkylenyloxy, wherein the O is attached to R$^2$, each of which is optionally substituted with 1 to 4 groups independently selected from methyl, ethyl, trifluoromethyl or oxo.

In one particular embodiment, E is a bond or unsubstituted (C$_1$-C$_3$)alkylene.

In a more particular embodiment, E is a bond or CH$_2$.

In an even more particular embodiment, E is a bond.

R$^2$ is (C$_1$-C$_6$)alkyl, aryl, heteroaryl, cycloalkyl or heterocyclyl and is optionally substituted with up to 4 groups independently selected halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl, hydroxy(C$_1$-C$_6$)alkoxy, —R$^9$, (C$_1$-C$_6$)alkylthio, (C$_3$-C$_6$)cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$.

In one particular embodiment, $R^2$ is an optionally substituted ($C_1$-$C_6$)alkyl, aryl, heteroaryl or cycloalkyl group.

In a more particular embodiment, $R^2$ is an optionally substituted phenyl, fluorophenyl, isopropyl, cyclopropyl, t-butyl or trifluoroethyl group, or E-$R^2$ is optionally substituted cyclopropylmethyl.

In another particular embodiment, $R^2$ is an optionally substituted phenyl or fluorophenyl group.

In another particular embodiment, $R^2$ is an optionally substituted ($C_1$-$C_6$)alkyl, aryl, heteroaryl or cycloalkyl group; each optionally substituted with up to four groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, and ($C_3$-$C_6$)cycloalkylthio.

In a more particular embodiment, $R^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($0_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, and ($C_3$-$C_6$)cycloalkythio.

In a more particular embodiment, $R^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen, cyano and nitro.

In another particular embodiment, $R^2$ is phenyl optionally substituted with one to three groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, and ($C_3$-$C_6$)cycloalkythio.

In yet a more particular embodiment, $R^2$ is phenyl optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen, cyano and nitro.

In yet another more particular embodiment, $R^2$ is phenyl or fluorophenyl.

$R^3$ is is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, or ($C_1$-$C_3$)alkoxy($C_1$-$C_3$)alkyl and is optionally substituted with up to four groups independently selected from H, —F, —CN, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl, $R^4O$—, $(R^4)_2N$—, $R^4O_2O$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), aryl-amino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo).

In one particular embodiment, $R^3$ is ($C_3$-$C_6$)alkenyl, hydroxy($C_2$-$C_5$)alkyl, cyano($C_2$-$C_5$)alkyl, dihydroxy($C_3$-$C_5$)alkyl, ω-$H_2NCO$($C_1$-$C_5$)alkyl, ($C_1$-$C_2$)alkoxy($C_1$-$C_4$)alkyl, $H_2NSO_2O$($C_2$-$C_5$)alkyl, $H_2NSO_2NH$($C_2$-$C_5$)alkyl, oxo($C_2$-$C_5$)alkyl, MeC(=O)NH($C_2$-$C_5$)alkyl, $MeSO_2NH$($C_2$-$C_5$)alkyl, or $MeSO_2NH$($C_2$-$C_5$)alkyl.

In another particular embodiment, $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2NC(=O)$—, MeNHC(=O)—, $HO_2C$—, $(HO)_2P(=O)O$—, $H_2NS(=O)_2O$—, $H_2NS(=O)_2NH$—, MeNHC(=O)NH—, MeNHC(=O)O—, oxo, cyano, $HO_2C$—, $HOCH_2CH_2NH$—, 4-morpholino, $HOCH_2C(=O)NH$—, $H_2NCH_2C(=O)NH$—, EtNHC(=O)NH, MeOC(=O)NH—, MeNHC(=NC≡N)NH—, MeS—, $MeSO_2$—MeSO$_2$N(Me)-, MeS(=O)$_2$NHC(=O)—, imidazolylamino-, imidazolyl, tetrazolyl, spirocyclopropyl, $FCH_2CH_2NH$, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2NCONH$—, $H_2NCO_2$—, $HOCH_2CH_2O$—, MeNH—, $Me_2N$— and MeCONMe.

In a more particular embodiment, $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2NC(=O)$—, MeNHC(=O)—, $HO_2C$—, MeNHC(=O)NH—, oxo, cyano, $HOCH_2C(=O)NH$—, EtNHC(=O)NH, MeS—, $MeSO_2$-MeSO$_2$N(Me)-, 2-oxo-1- pyrrolidinyl, H₂NCONH—, H₂NCO₂—, HOCH₂CH₂O—, MeNH—, Me₂N— and MeCONMe.

In yet a more particular embodiment, $R^3$ is 2-methylallyl, MeSO₂NHCH₂CH₂CH₂, H₂NC(=O)CH₂CH₂, H₂NC(=O)CMe₂CH₂, 3-hydroxypropyl, 3-hydroxy-3-methylbutyl, 2-hydroxyethyl, 2-hydroxy-2-methylpropyl or 2-cyano-2-methylpropyl.

In an even more particular embodiment, $R^3$ is 2-methylallyl, 2-hydroxy-2-methylpropyl or 2-cyano-2-methylpropyl.

n is 0, 1 or 2.

In a particular embodiment, n is 1.

Q is O, CH₂ or $NR^5$.

In a particular embodiment, Q is O.

Each $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl.

Each $R^5$ is independently H, $(C_1-C_6)$alkyl, halo$(C_1-C_6)$alkyl or hydroxy$(C_1-C_6)$alkyl.

Each $R^6$ is independently $(C_1-C_6)$alkyl, $(C_2-C_6)$alkenyl, $(C_2-C_6)$alkynyl or $(C_1-C_6)$alkoxy.

$V^1$ is $(C_1-C_6)$alkylene, $(C_1-C_6)$alkenylene, $(C_1-C_6)$alkynylene or $(C_1-C_6)$alkyleneoxy.

Each $R^7$ is independently $(C_3-C_6)$cycloalkyl or $(C_3-C_6)$cycloalkoxy;

$R^8$ is heterocyclyl.

$R^9$ is $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(a_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl or halo$(C_1-C_6)$alkoxy$(C_1-C_6)$alkyl.

In a 1ˢᵗ specific embodiment, the compound of the present invention is represented by Structural Formula (II):

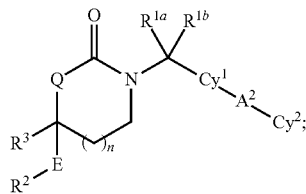

(II)

or a pharmaceutically acceptable salt, enantiomer or diastereomer thereof.

$R^{1a}$ and $R^{1b}$ are, independently, optionally substituted $(C_1-C_6)$alkyl, and values and particular values for the remainder of the variables in Structural Formula (II) are as described above for Structural Formula (I).

In a more specific embodiment for compounds of Structural Formula (II), $Cy^1$ is an optionally substituted cyclohexyl, phenyl, pyridyl, pyrimidinyl, thiazolyl, triazolyl or benzothiazolyl group, and values and particular values for the remainder of the variables in Structural Formula (II) are as described above for Structural Formula (I).

In an even more specific embodiment for compounds of Structural Formula (II), $R^{1a}$ and $R^{1b}$ are, independently, optionally substituted $(C_1-C_6)$alkyl, $Cy^1$ is an optionally substituted cyclohexyl, phenyl, pyridyl, pyrimidinyl, thiazolyl, triazolyl or benzothiazolyl group, and values and particular values for the remainder of the variables in Structural Formula (II) are as described above for Structural Formula (I).

In a 2ⁿᵈ specific embodiment, the compound of the present invention is represented by Structural Formula (II-A):

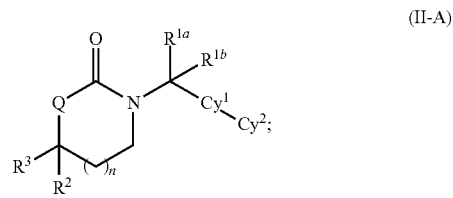

(II-A)

or a pharmaceutically acceptable salt, enantiomer or diastereomer thereof.

The values and specific values for the variables in Structural Formula (II-A) are as described above for Structural Formula (I).

In a more specific embodiment for compounds of Structural Formula (II-A), $R^{1a}$ and $R^{1b}$ are, independently, an optionally substituted methyl or ethyl group, $Cy^1$ is an optionally substituted cyclohexyl, phenyl, pyridyl, pyrimidinyl, thiazolyl, triazolyl or benzothiazolyl group, and values and specific values for the remainder of the variables in Structural Formula (II-A) are as described above for Structural Formula (I). In another more specific embodiment for compounds of Structural Formula (II-A), $R^{1a}$ and $R^{1b}$ are, independently, an optionally substituted methyl or ethyl group, $Cy^1$ is an optionally substituted cyclohexyl, phenyl, pyridyl, pyrimidinyl, thiazolyl, triazolyl or benzothiazolyl group, Q is O, CH₂ or NH, and values and specific values for the remainder of the variables in Structural Formula (II-A) are as described above for Structural Formula (I).

In a 3ʳᵈ specific embodiment, the compound of the present invention is represented by Structural Formula (II-B):

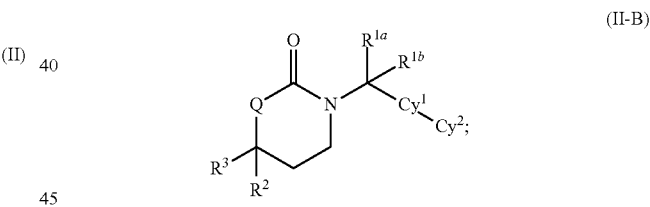

(II-B)

or a pharmaceutically acceptable salt, enantiomer or diastereomer thereof.

The values and specific values for the variables in Structural Formula (II-B) are as described above for Structural Formula (II-A).

In a more specific embodiment for compounds of Structural Formula (II-B), $R^{1a}$ and $R^{1b}$ are, independently, an optionally substituted methyl or ethyl group, $Cy^1$ is an optionally substituted cyclohexyl, phenyl, pyridyl, pyrimidinyl, thiazolyl, triazolyl or benzothiazolyl group, Q is O, CH₂ or NH, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group, and values and specific values for the remainder of the variables in Structural Formula (II-B) are as described above for Structural Formula (I).

In another more specific embodiment for compounds of Structural Formula (II-B), $R^{1a}$ and $R^{1b}$ are, independently, optionally substituted methyl, $Cy^1$ is an optionally substituted cyclohexyl, phenyl, pyridyl, pyrimidinyl, thiazolyl, triazolyl or benzothiazolyl group, Q is O, $CH_2$ or NH, and values and specific values for the remainder of the variables in Structural Formula (II-B) are as described above for Structural Formula (I).

In a more specific embodiment for compounds of Structural Formula (II-B), $Cy^1$ is an optionally substituted cyclohexyl, phenyl, pyridyl, pyrimidinyl, thiazolyl, triazolyl or benzothiazolyl group, Q is O, $CH_2$ or NH, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group, $R^{1a}$ and $R^{1b}$ are, independently, optionally substituted methyl, and values and specific values for the remainder of the variables in Structural Formula (II-B) are as described above for Structural Formula (I).

In a 4specific embodiment, the compound of the present invention is represented by Structural Formula (II-C):

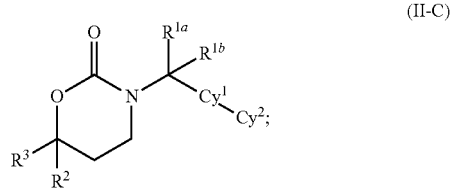

(II-C)

or a pharmaceutically acceptable salt, enantiomer or diastereomer thereof.

The values and specific values for the variables in Structural Formula (II-C) are as described above for Structural Formula (II-B).

In a more specific embodiment for compounds of Structural Formula (II-C), $Cy^1$ is an optionally substituted phenyl or triazolyl group, and values and specific values for the remainder of the variables in Structural Formula (II-C) are as described above for Structural Formula (II-B).

In another more specific embodiment for compounds of Structural Formula (II-C), $Cy^2$ is an optionally substituted phenyl or oxodihydropyridyl group, and values and specific values for the remainder of the variables in Structural Formula (II-C) are as described above for Structural Formula (II-B).

In another more specific embodiment for compounds of Structural Formula (II-C), the group represented by $Cy^2$ is optionally substituted with one to four groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl and hydroxy($C_1$-$C_6$)alkoxy, and values and specific values for the remainder of the variables in Structural Formula (II-C) are as described above for Structural Formula (II-B).

In another more specific embodiment for compounds of Structural Formula (II-C), $R^{1a}$ and $R^{1b}$ are, independently, optionally substituted methyl, $Cy^1$ is an optionally substituted phenyl or triazolyl group, the group represented by $Cy^2$ is optionally substituted with one to four groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl and hydroxy($C_1$-$C_6$)alkoxy, and values and specific values for the remainder of the variables in Structural Formula (II-C) are as described above for Structural Formula (I).

In another more specific embodiment for compounds of Structural Formula (II-C), $R^{1a}$ and $R^{1b}$ are, independently, optionally substituted methyl, $Cy^2$ is an optionally substituted phenyl or oxodihydropyridyl group, the group represented by $Cy^2$ is optionally substituted with one to four groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl and hydroxy($C_1$-$C_6$)alkoxy, and values and specific values for the remainder of the variables in Structural Formula (II-C) are as described above for Structural Formula (I).

In another more specific embodiment for compounds of Structural Formula (II-C), $R^{1a}$ and $R^{1b}$ are, independently, optionally substituted methyl, $Cy^1$ is an optionally substituted phenyl or triazolyl group, $Cy^2$ is an optionally substituted phenyl or oxodihydropyridyl group, the group represented by $Cy^2$ is optionally substituted with one to four groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl $^{and}$ hydroxy($C_1$-$C_6$)alkoxy, and values and specific values for the remainder of the variables in Structural Formula (II-C) are as described above for Structural Formula (I) (II-B).

In a 5$^{th}$ specific embodiment, the compound of the present invention is represented by Structural Formula (II-D):

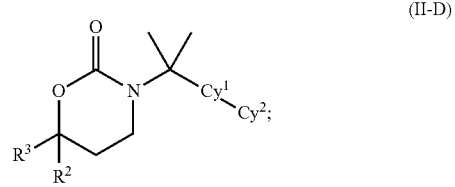

(II-D)

or a pharmaceutically acceptable salt, enantiomer or diastereomer thereof.

The values and specific values for the variables in Structural Formula (II-D) are as described above for Structural Formula (II-C).

In a more specific embodiment for compounds of Structural Formula (II-D), $Cy^1$ is an optionally substituted phenyl or triazolyl group, $Cy^2$ is an optionally substituted phenyl or oxodihydropyridyl group, $Cy^2$ is optionally substituted with one to four groups independently selected from $(C_1-C_6)$alkyl and $(C_3-C_6)$cycloalkyl, and values and specific values for the remainder of the variables in Structural Formula (II-D) are as described above for Structural Formula (I).

In a 6$^{th}$ specific embodiment, the compound of the present invention is represented by Structural Formula (II-E):

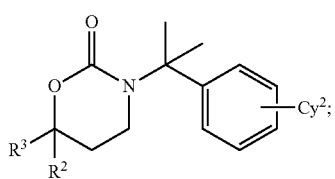

(II-E)

or a pharmaceutically acceptable salt, enantiomer or diastereomer thereof.

The values and specific values for the variables in Structural Formula (II-E) are as described above for Structural Formula (II-D).

In a more specific embodiment for compounds of Structural Formula (II-E), $Cy^2$ is an optionally substituted phenyl or oxodihydropyridyl group, $Cy^2$ is optionally substituted with one to four groups independently selected from $(C_1-C_6)$alkyl and $(C_3-C_6)$cycloalkyl, and values and specific values for the remainder of the variables in Structural Formula (II-E) are as described above for Structural Formula (I).

In a 7$^{th}$ specific embodiment, the compound of the present invention is represented by Structural Formula (III):

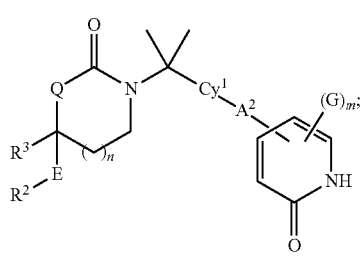

(III)

or a pharmaceutically acceptable salt, enantiomer or diastereomer thereof.

The oxodihydropyridyl ring in formula (III) is independently and optionally substituted on the substitutable ring carbons and/or the ring nitrogen, m is 0, 1, 2, 3 or 4, each G independently is halogen, —CN, —NO$_2$, —NH$_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, —R$^9$, $(C_1-C_6)$alkylthio, $(C_3-C_6)$cycloalkythio, —SR$^9$, —S(=O)R$^6$, —S(=O) R$^7$, —S(=O)R$^9$, —S(=O)$_2$R$^6$, —S(=O)$_2$R$^7$, —S(=O)$_2$ R$^9$, —NHR$^6$, —N(R$^6$), —C(O)R$^6$, —C(=O)NH$_2$, —S(=O)$_2$ NH$_2$, —C(=O)NHR$^6$, —C(=O)NR$^6$R$^6$, —C(=O)R$^9$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O) R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R)$_2$, cyano$(C_1-C_6)$alkyl, —V$^1$—C(=O)NH$_2$, —V$^1$—C(=O)NHR$^6$, —V$^1$—C(=O) N(R$^6$)$_2$, —V$^1$—C(=O)NHR$^7$, —V$^1$—C(=O)NR$^6$R$^7$ or —V$^1$—C(=O)N(R$^7$)$_2$, and values and particular values for the remainder of the variables in Structural Formula (III) are as described above for Structural Formula (I).

In a more specific embodiment for compounds of Structural Formula (III), $Cy^1$ is an optionally substituted cyclohexyl, phenyl, pyridyl, pyrimidinyl, thiazolyl, triazolyl or benzothiazolyl group, and values and specific values for the remainder of the variables in Structural Formula (III) are as described above for Structural Formula (I).

In an 8$^{th}$ specific embodiment, the compound of the present invention is represented by Structural Formula (III-A):

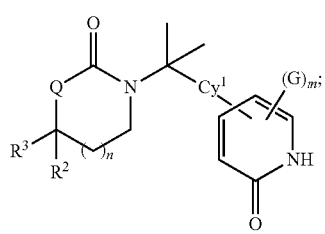

(III-A)

or a pharmaceutically acceptable salt, enantiomer or diastereomer thereof.

Values and particular values for the variables in Structural Formula (III-A) are as described above for Structural Formula (III).

In a more specific embodiment for compounds of Structural Formula (III-A), Q is O, CH$_2$ or NH, the oxodihydropyridyl ring in formula (III-A) is independently and optionally substituted on the substitutable ring carbons and/or the ring nitrogen, m is 0, 1, 2, 3 or 4, each G independently is halogen, —CN, —NO$_2$, —NH$_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, —R$^9$, $(C_1-C_6)$alkylthio, $(C_3-C_6)$cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R)$_2$, cyano$(C_1-C_6)$alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ or —V$^1$—C(=O)N(R$^7$)$_2$, and values and specific values for the remainder of the variables in Structural Formula (III-A) are as described above for Structural Formula (I).

In a more specific embodiment for compounds of Structural Formula (III-A), $Cy^1$ is an optionally substituted cyclohexyl, phenyl, pyridyl, pyrimidinyl, thiazolyl, triazolyl or benzothiazolyl group, Q is O, CH$_2$ or NH, the oxodihydropyridyl ring in formula (III-A) is independently and optionally substituted on the substitutable ring carbons and/or the ring nitrogen, m is 0, 1, 2, 3 or 4, each G independently is halogen, —CN, —NO$_2$, —NH$_2$, —OH, —COOH, $(C_1-C_6)$alkyl, $(C_2-$ $C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, —$R^9$, ($C_1$-$C_6$)alkylthio, ($C_3$-$C_6$)cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —NHC(=O)$R^6$, —$V^1$—NHC(=O)$R^6$, —NHS(=O)$_2R^6$, —$V^1$—NHS(=O)$_2R^6$, —$V^1$—C(=O)$R^6$, heteroaryl, aryl, heterocyclyl, oxo, —$V^1$—NH2, —$V^1$—NHR$^6$, —$V^1$—N(R$^6$)$_2$, —C(=O)R$^7$, —C(=O)NHR$^7$, —C(=O)NR$^6$R$^7$, —C(=O)N(R)$_2$, —S(=O)$_2$NHR$^7$, —S(=O)$_2$NR$^6$R$^7$, —S(=O)$_2$N(R$^7$)$_2$, cyano($C_1$-$C_6$)alkyl, —$V^1$—C(=O)NH$_2$, —$V^1$—C(=O)NHR$^6$, —$V^1$—C(=O)N(R$^6$)$_2$, —$V^1$—C(=O)NHR$^7$, —$V^1$—C(=O)NR$^6$R$^7$ or —$V^1$—C(=O)N(R$^7$)$_2$, and values and specific values for the remainder of the variables in Structural Formula (III-A) are as described above for Structural Formula (I).

In a 9$^{th}$ specific embodiment, the compound of the present invention is represented by Structural Formula (III-B):

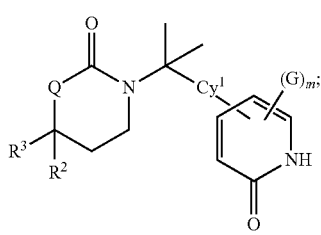

(III-B)

or a pharmaceutically acceptable salt, enantiomer or diastereomer thereof.

Values and particular values for the variables in Structural Formula (III-B) are as described above for Structural Formula (III-A).

In a more specific embodiment for compounds of Structural Formula (III-B), Q is O, CH$_2$ or NH, the oxodihydropyridyl ring in formula (III) is independently and optionally substituted on the substitutable ring carbons and/or the ring nitrogen, m is 0, 1, 2, 3 or 4, each G independently is halogen, —CN, —NO$_2$, —NH$_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, —$R^9$, ($C_1$-$C_6$)alkylthio, ($C_3$-$C_6$)cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —NHC(=O)$R^6$, —$V^1$—NHC(=O)$R^6$, —NHS(=O)$_2R^6$, —$V^1$—NHS(=O)$_2R^6$, —$V^1$—C(=O)$R^6$, heteroaryl, aryl, heterocyclyl, oxo, —$V^1$—NH2, —$V^1$—NHR$^6$, —$V^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R)$_2$, cyano($C_1$-$C_6$)alkyl, —$V^1$—C(=O)NH$_2$, —$V^1$—C(=O)NHR$^6$, —$V^1$—C(=O)N(R$^6$)$_2$, —$V^1$—C(=O)NHR$^7$, —$V^1$—C(=O)NR$^6$R$^7$ or —$V^1$—C(=O)N(R$^7$)$_2$, Cy$^1$ is an optionally substituted phenyl or triazolyl group, and values and specific values for the remainder of the variables in Structural Formula (III-B) are as described above for Structural Formula (I).

In a 10$^{th}$ specific embodiment, the compound of the present invention is represented by Structural Formula (IV):

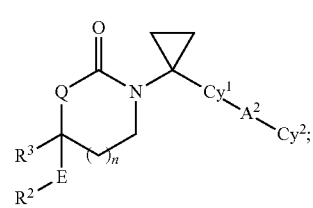

(IV)

or a pharmaceutically acceptable salt, enantiomer or diastereomer thereof.

Values and particular values for the variables in Structural Formula (IV) are as described above for Structural Formula (I).

In a more specific embodiment for compounds of Structural Formula (IV), Cy$^1$ is an optionally substituted cyclohexyl, phenyl, pyridyl, pyrimidinyl, thiazolyl, triazolyl or benzothiazolyl group, and values and particular values for the remainder of the variables in Structural Formula (IV) are as described above for Structural Formula (I).

In an 11$^{th}$ specific embodiment, the compound of the present invention is represented by Structural Formula (IV-A):

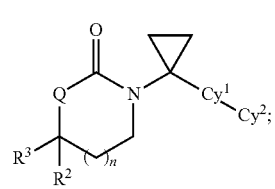

(IV-A)

or a pharmaceutically acceptable salt, enantiomer or diastereomer thereof.

The values and specific values for the variables in Structural Formula (IV-A) are as described above for Structural Formula (IV).

In a more specific embodiment for compounds of Structural Formula (IV-A), Cy$^1$ is an optionally substituted cyclohexyl, phenyl, pyridyl, pyrimidinyl, thiazolyl, triazolyl or benzothiazolyl group, Q is O, CH$_2$ or NH, and values and specific values for the remainder of the variables in Structural Formula (IV-A) are as described above for Structural Formula (I).

In a 12$^{th}$ specific embodiment, the compound of the present invention is represented by Structural Formula (IV-B):

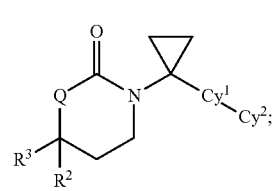

(IV-B)

or a pharmaceutically acceptable salt, enantiomer or diastereomer thereof.

The values and specific values for the variables in Structural Formula (IV-B) are as described above for Structural Formula (IV-A).

In a more specific embodiment for compounds of Structural Formula (IV-B), $Cy^1$ is an optionally substituted cyclohexyl, phenyl, pyridyl, pyrimidinyl, thiazolyl, triazolyl or benzothiazolyl group, Q is O, $CH_2$ or NH, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group, and values and specific values for the remainder of the variables in Structural Formula (IV-B) are as described above for Structural Formula (I).

In a 13$^{th}$ specific embodiment, the compound of the present invention is represented by Structural Formula (IV-C):

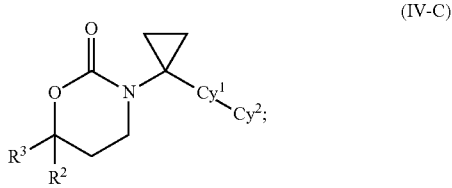

(IV-C)

or a pharmaceutically acceptable salt, enantiomer or diastereomer thereof.

The values and specific values for the variables in Structural Formula (IV-C) are as described above for Structural Formula (IV-B).

In a more specific embodiment for compounds of Structural Formula (IV-C), $Cy^1$ is an optionally substituted phenyl or triazolyl group, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group, and values and specific values for the remainder of the variables in Structural Formula (IV-C) are as described above for Structural Formula (I).

In another more specific embodiment for compounds of Structural Formula (IV-C), $Cy^1$ is an optionally substituted phenyl or triazolyl group, $Cy^2$ is an optionally substituted phenyl or oxodihydropyridyl group, and values and specific values for the remainder of the variables in Structural Formula (IV-C) are as described above for Structural Formula (I).

In another more specific embodiment for compounds of Structural Formula (IV-C), $Cy^1$ is an optionally substituted cyclohexyl, phenyl, pyridyl, pyrimidinyl, thiazolyl, triazolyl or benzothiazolyl group, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group, the group represented by $Cy^2$ is optionally substituted with one to four groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl and hydroxy$(C_1-C_6)$alkoxy, and values and specific values for the remainder of the variables in Structural Formula (IV-C) are as described above for Structural Formula (I).

In another more specific embodiment for compounds of Structural Formula (IV-C), $Cy^1$ is an optionally substituted phenyl or triazolyl group, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxohexahydro-1,2-thiazinyl, or cyclopropyl group, the group represented by $Cy^2$ is optionally substituted with one to four groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl and hydroxy$(C_1-C_6)$alkoxy, and values and specific values for the remainder of the variables in Structural Formula (IV-C) are as described above for Structural Formula (I).

In another more specific embodiment for compounds of Structural Formula (IV-C), $Cy^1$ is an optionally substituted cyclohexyl, phenyl, pyridyl, pyrimidinyl, thiazolyl, triazolyl or benzothiazolyl group, $Cy^2$ is an optionally substituted phenyl or oxodihydropyridyl group, the group represented by $Cy^2$ is optionally substituted with one to four groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl $^{and}$ hydroxy$(C_1-C_6)$alkoxy, and values and specific values for the remainder of the variables in Structural Formula (IV-C) are as described above for Structural Formula (I).

In another more specific embodiment for compounds of Structural Formula (IV-C), $Cy^1$ is an optionally substituted phenyl or triazolyl group, $Cy^2$ is an optionally substituted phenyl or oxodihydropyridyl group, the group represented by Cy² is optionally substituted with one to four groups independently selected from halogen, —CN, —NO₂, —NH₂, —OH, —COOH, (C₁-C₆)alkyl, (C₂-C₆)alkenyl, (C₂-C₆)alkynyl, (C₁-C₆)alkoxy, (C₃-C₆)cycloalkyl, (C₃-C₆)cycloalkoxy, hydroxy(C₁-C₆)alkyl, hydroxy(C₃-C₆)cycloalkyl, hydroxy (C₂-C₆)alkenyl and hydroxy(C₁-C₆)alkoxy, and values and specific values for the remainder of the variables in Structural Formula (IV-C) are as described above for Structural Formula (I).

In a 14ᵗʰ specific embodiment, the compound of the present invention is represented by Structural Formula (IV-D):

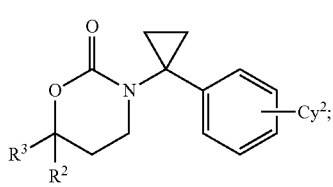

(IV-D)

or a pharmaceutically acceptable salt, enantiomer or diastereomer thereof.

The values and specific values for the variables in Structural Formula (IV-D) are as described above for Structural Formula (IV-C).

In a more specific embodiment for compounds of Structural Formula (IV-D), Cy² is an optionally substituted phenyl or oxodihydropyridyl group, Cy² is optionally substituted with one to four groups independently selected from (C₁-C₆) alkyl and (C₃-C₆)cycloalkyl, and values and specific values for the remainder of the variables in Structural Formula (IV-D) are as described above for Structural Formula (I).

In a 15ᵗʰ specific embodiment, the compound of the present invention is represented by Structural Formula (V):

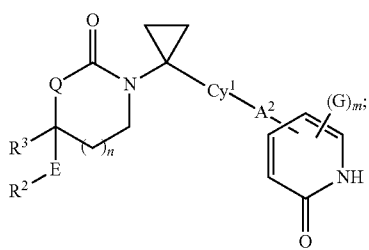

(V)

or a pharmaceutically acceptable salt, enantiomer or diastereomer thereof.

The oxodihydropyridyl ring in formula (V) is independently and optionally substituted on the substitutable ring carbons and/or the ring nitrogen, m is 0, 1, 2, 3 or 4, each G independently is halogen, —CN, —NO₂, —NH₂, —OH, —COOH, (C₁-C₆)alkyl, (C₂-C₆)alkenyl, (C₂-C₆)alkynyl, (C₁-C₆)alkoxy, (C₃-C₆)cycloalkyl, (C₃-C₆)cycloalkoxy, hydroxy(C₁-C₆)alkyl, hydroxy(C₃-C₆)cycloalkyl, hydroxy (C₂-C₆)alkenyl, hydroxy(C₁-C₆)alkoxy, —R⁹, (C₁-C₆)alkylthio, (C₃-C₆)cycloalkythio, —SR⁹, —S(=O)R⁶, —S(=O)R⁷, —S(=O)R⁹, —S(=O)₂R⁶, —S(=O)₂R⁷, —S(=O)₂R⁹, —NHR⁶, —N(R⁶), —C(=O)R⁶, —C(=O)NH₂, —S(=O)₂NH₂, —C(=O)NHR⁶, —C(=O)NR⁶R⁶, —C(=O)R⁷, —S(=O)₂NHR⁶, —S(=O)₂N(R⁶)₂, —S(=O)₂R⁸, —NHC(=O)R⁶, —V¹—NHC(=O)R⁶, —NHS(=O)₂R⁶, —V¹—NHS(=O)₂R⁶, —V¹—C(=O) R⁶, heteroaryl, aryl, heterocyclyl, oxo, —V¹—NH2, —V¹—NHR⁶, —V¹—N(R⁶)₂, —C(=O)R⁷, —C(=O)NHR⁷, —C(=O)NR⁶R⁷, —C(=O)N(R⁷)₂, —S(=O)₂NHR⁷, —S(=O)₂NR⁶R⁷, —S(=O)₂N(R⁷)₂, cyano(C₁-C₆)alkyl, —V¹—C(=O)NH₂, —V¹—C(=O)NHR⁶, —V¹—C(=O) N(R⁶)₂, —V¹—C(=O)NHR⁷, —V¹—C(=O)NR⁶R⁷ or —V¹—C(=O)N(R⁷)₂, and values and particular values for the remainder of the variables in Structural Formula (V) are as described above for Structural Formula (I).

In a more specific embodiment for compounds of Structural Formula (V), Cy¹ is an optionally substituted cyclohexyl, phenyl, pyridyl, pyrimidinyl, thiazolyl, triazolyl or benzothiazolyl group, and values and specific values for the remainder of the variables in Structural Formula (V) are as described above for Structural Formula (I).

In an 16ᵗʰ specific embodiment, the compound of the present invention is represented by Structural Formula (V-A):

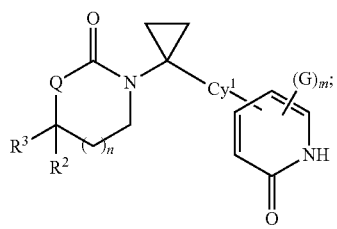

(V-A)

or a pharmaceutically acceptable salt, enantiomer or diastereomer thereof.

Values and particular values for the variables in Structural Formula (V-A) are as described above for Structural Formula (V).

In a more specific embodiment for compounds of Structural Formula (V-A), Q is O, CH₂ or NH, the oxodihydropyridyl ring in formula (V) is independently and optionally substituted on the substitutable ring carbons and/or the ring nitrogen, m is 0, 1, 2, 3 or 4, each G independently is halogen, —CN, —NO₂, —NH₂, —OH, —COOH, (C₁-C₆)alkyl, (C₂-C₆)alkenyl, (C₂-C₆)alkynyl, (C₁-C₆)alkoxy, (C₃-C₆)cycloalkyl, (C₃-C₆)cycloalkoxy, hydroxy(C₁-C₆)alkyl, hydroxy(C₃-C₆)cycloalkyl, hydroxy(C₂-C₆)alkenyl, hydroxy(C₁-C₆)alkoxy, —R⁹, (C₁-C₆)alkylthio, (C₃-C₆)cycloalkythio, —SR⁹, —S(=O)R⁶, —S(=O)R⁷, —S(=O)R⁹, —S(=O)₂R⁶, —S(=O)₂R⁷, —S(=O)₂R⁹, —NHR⁶, —N(R⁶), —C(=O)R⁶, —C(=O)NH₂, —S(=O)₂NH₂, —C(=O)NHR⁶, —C(=O)NR⁶R⁶, —C(=O)R⁸, —S(=O)₂ NHR⁶, —S(=O)₂N(R⁶)₂, —S(=O)₂R⁸, —NHC(=O)R⁶, —V¹—NHC(=O)R⁶, —NHS(=O)₂R⁶, —V¹—NHS(=O)₂R⁶, —V¹—C(=O)R⁶, heteroaryl, aryl, heterocyclyl, oxo, —V¹—NH2, —V¹—NHR⁶, —V¹—N(R⁶)₂, —C(=O)R⁷, —C(=O)NHR⁷, —C(=O)NR⁶R⁷, —C(=O) N(R⁷)₂, —S(=O)₂NHR⁷, —S(=O)₂NR⁶R⁷, —S(=O)₂N (R)₂, cyano(C₁-C₆)alkyl, —V¹—C(=O)NH₂, —V¹—C (=O)NHR⁶, —V¹—C(=O)N(R⁶)₂, —V¹—C(=O)NHR⁷, —V¹—C(=O)NR⁶R⁷ or —V¹—C(=O)N(R⁷)₂, and values and specific values for the remainder of the variables in Structural Formula (V-A) are as described above for Structural Formula (I).

In a more specific embodiment for compounds of Structural Formula (V-A), Cy¹ is an optionally substituted cyclohexyl, phenyl, pyridyl, pyrimidinyl, thiazolyl, triazolyl or benzothiazolyl group, Q is O, CH₂ or NH, the oxodihydropyridyl ring in formula (V-A) is independently and optionally substituted on the substitutable ring carbons and/or the ring nitrogen, m is 0, 1, 2, 3 or 4, each G independently is halogen, —CN, —NO₂, —NH₂, —OH, —COOH, (C₁-C₆)alkyl, (C₂-C₆)alkenyl, (C₂-C₆)alkynyl, (C₁-C₆)alkoxy, (C₃-C₆)cycloalkyl, (C₃-C₆)cycloalkoxy, hydroxy(C₁-C₆)alkyl, hydroxy(C₃-C₆)cycloalkyl, hydroxy(C₂-C₆)alkenyl, hydroxy(C₁-C₆)alkoxy, —R⁹, (C₁-C₆)alkylthio, (C₃-C₆)cycloalkythio, —SR⁹, —S(=O)R⁶, —S(=O)R⁷, —S(=O)R⁹, —S(=O)₂R⁶, —S(=O)₂R⁷, —S(=O)₂R⁹, —NHR⁶, —N(R⁶), —C(=O)R⁶, —C(=O)NH₂, —S(=O)₂NH₂, —C(=O)NHR⁶, —C(=O)NR⁶R⁶, —C(=O)R⁸, —S(=O)₂NHR⁶, —S(=O)₂N(R⁶)₂, —S(=O)₂R⁸, —NHC(=O)R⁶, —V¹—NHC(=O)R⁶, —NHS(=O)₂R⁶, —V¹—NHS(=O)₂R⁶, —V¹—C(=O)R⁶, heteroaryl, aryl, heterocyclyl, oxo, —V¹—NH2, —V¹—NHR⁶, —V¹—N(R⁶)₂, —C(=O)R⁷, —C(=O)NHR⁷, —C(=O)NR⁶R⁷, —C(=O)N(R)₂, —S(=O)₂NHR⁷, —S(=O)₂NR⁶R⁷, —S(=O)₂N(R⁷)₂, cyano(C₁-C₆)alkyl, —V¹—C(=O)NH₂, —V¹—C(=O)NHR⁶, —V¹—C(=O)N(R⁶)₂, —V¹—C(=O)NHR⁷, —V¹—C(=O)NR⁶R⁷ or —V¹—C(=O)N(R⁷)₂, and values and specific values for the remainder of the variables in Structural Formula (V-A) are as described above for Structural Formula (I).

In a 17$^{th}$ specific embodiment, the compound of the present invention is represented by Structural Formula (V-B):

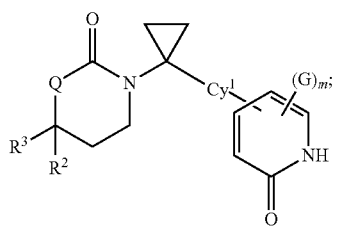

(V-B)

or a pharmaceutically acceptable salt, enantiomer or diastereomer thereof.

Values and particular values for the variables in Structural Formula (V-B) are as described above for Structural Formula (V-A).

In a more specific embodiment for compounds of Structural Formula (V-B), Q is O, CH₂ or NH, the oxodihydropyridyl ring in formula (V-B) is independently and optionally substituted on the substitutable ring carbons and/or the ring nitrogen, m is 0, 1, 2, 3 or 4, each G independently is halogen, —CN, —NO₂, —NH₂, —OH, —COOH, (C₁-C₆)alkyl, (C₂-C₆)alkenyl, (C₂-C₆)alkynyl, (C₁-C₆)alkoxy, (C₃-C₆)cycloalkyl, (C₃-C₆)cycloalkoxy, hydroxy(C₁-C₆)alkyl, hydroxy(C₃-C₆)cycloalkyl, hydroxy(C₂-C₆)alkenyl, hydroxy(C₁-C₆)alkoxy, —R⁹, (C₁-C₆)alkylthio, (C₃-C₆)cycloalkythio, —SR⁹, —S(=O)R⁶, —S(=O)R⁷, —S(=O)R⁹, —S(=O)₂R⁶, —S(=O)₂R⁷, —S(=O)₂R⁹, —NHR⁶, —N(R⁶), —C(=O)R⁶, —C(=O)NH₂, —S(=O)₂NH₂, —C(=O)NHR⁶, —C(=O)NR⁶R⁶, —C(=O)R⁸, —S(=O)₂NHR⁶, —S(=O)₂N(R⁶)₂, —S(=O)₂R⁸, —NHC(=O)R⁶, —V¹—NHC(=O)R⁶, —NHS(=O)₂R⁶, —V¹—NHS(=O)₂R⁶, —V¹—C(=O)R⁶, heteroaryl, aryl, heterocyclyl, oxo, —V¹—NH2, —V¹—NHR⁶, —V¹—N(R⁶)₂, —C(=O)R⁷, —C(=O)NHR⁷, —C(=O)NR⁶R⁷, —C(=O)N(R⁷)₂, —S(=O)₂NHR⁷, —S(=O)₂NR⁶R⁷, —S(=O)₂N(R)₂, cyano(C₁-C₆)alkyl, —V¹—C(=O)NH₂, —V¹—C(=O)NHR⁶, —V¹—C(=O)N(R⁶)₂, —V¹—C(=O)NHR⁷, —V¹—C(=O)NR⁶R⁷ or —V¹—C(=O)N(R⁷)₂, Cy¹ is an optionally substituted phenyl or triazolyl group, and values and specific values for the remainder of the variables in Structural Formula (V-B) are as described above for Structural Formula (V-A).

In an 18$^{th}$ specific embodiment, the compound of the present invention is represented by Structural Formula (VI):

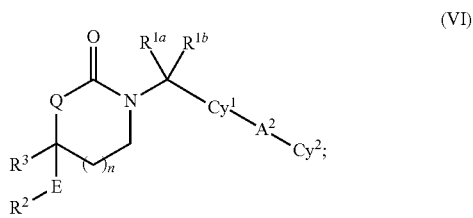

(VI)

or a pharmaceutically acceptable salt, enantiomer or diastereomer thereof.

Values and particular values for the variables in Structural Formula (VI) are as described above for Structural Formula (I).

In a more specific embodiment for compounds of Structural Formula (VI), Cy¹ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and values and particular values for the remainder of the variables in Structural Formula (VI) are as described above for Structural Formula (I).

In another more specific embodiment for compounds of Structural Formula (VI), R$^{1a}$ and R$^{1b}$ are, independently, hydrogen, optionally substituted methyl or optionally substituted ethyl, or R$^{1a}$ and R$^{1b}$ taken together with the carbon to which they are attached form an optionally substituted cyclopropyl group, and values and particular values for the remainder of the variables in Structural Formula (VI) are as described above for Structural Formula (I).

In an even more specific embodiment for compounds of Structural Formula (VI), R$^{1a}$ and R$^{1b}$ are, independently, hydrogen, optionally substituted methyl or optionally substituted ethyl, or R$^{1a}$ and R$^{1b}$ taken together with the carbon to which they are attached form an optionally substituted cyclopropyl group, Cy¹ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and values and particular values for the remainder of the variables in Structural Formula (VI) are as described above for Structural Formula (I), and values and particular values for the remainder of the variables in Structural Formula (VI) are as described above for Structural Formula (I).

In another more specific embodiment for compounds of Structural Formula (VI), Q is O, CH$_2$ or NH, and values and particular values for the remainder of the variables in Structural Formula (VI) are as described above for Structural Formula (I).

In another more specific embodiment for compounds of Structural Formula (VI), Q is O, CH$_2$ or NH, Cy$^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and values and particular values for the remainder of the variables in Structural Formula (VI) are as described above for Structural Formula (I).

In another more specific embodiment for compounds of Structural Formula (VI), Q is O, CH$_2$ or NH, R$^{1a}$ and R$^{1b}$ are, independently, hydrogen, optionally substituted methyl or optionally substituted ethyl, or R$^{1a}$ and R$^{1b}$ taken together with the carbon to which they are attached form an optionally substituted cyclopropyl group, and values and particular values for the remainder of the variables in Structural Formula (VI) are as described above for Structural Formula (I).

In an even more specific embodiment for compounds of Structural Formula (VI), Q is O, CH$_2$ or NH, R$^{1a}$ and R$^{1b}$ are, independently, hydrogen, optionally substituted methyl or optionally substituted ethyl, or R$^{1a}$ and R$^{1b}$ taken together with the carbon to which they are attached form an optionally substituted cyclopropyl group, Cy$^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and values and particular values for the remainder of the variables in Structural Formula (VI) are as described above for Structural Formula (I).

In a 19$^{th}$ specific embodiment, the compound of the present invention is represented by Structural Formula (IV-A):

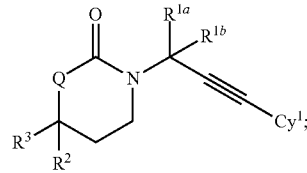

(VI-A)

or a pharmaceutically acceptable salt, enantiomer or diastereomer thereof.

The values and specific values for the variables in Structural Formula (VI-A) are as described above for Structural Formula (VI).

In a more specific embodiment for compounds of Structural Formula (VI-A),

R$^{1a}$ and R$^{1b}$ are, independently, hydrogen or methyl, or R$^{1a}$ and R$^{1b}$ taken together with the carbon to which they are attached form cyclopropyl, Cy$^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and values and specific values for the remainder of the variables in Structural Formula (VI-A) are as described above for Structural Formula (I).

In a 20$^{th}$ specific embodiment, the compound of the present invention is represented by Structural Formula (VI-B):

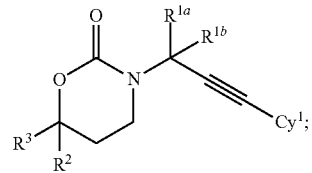

(VI-B)

or a pharmaceutically acceptable salt, enantiomer or diastereomer thereof.

The values and specific values for the variables in Structural Formula (VI-B) are as described above for Structural Formula (VI-A).

In a more specific embodiment for compounds of Structural Formula (VI-B), R$^{1a}$ and R$^{1b}$ are, independently, hydrogen or methyl, or R$^{1a}$ and R$^{1b}$ taken together with the carbon to which they are attached form cyclopropyl, Cy$^1$ is an optionally substituted phenyl or oxodihydroquinolinyl group, and values and specific values for the remainder of the variables in Structural Formula (VI-B) are as described above for Structural Formula (I).

In a 20$^{th}$ specific embodiment, the compound of the present invention is represented by Structural Formula (VII):

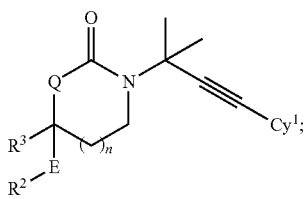

(VII)

or a pharmaceutically acceptable salt, enantiomer or diastereomer thereof.

The values and specific values for the variables in Structural Formula (VII) are as described above for Structural Formula (VI).

In a more specific embodiment for compounds of Structural Formula (VII), $Cy^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and values and specific values for the remainder of the variables in Structural Formula (VII) are as described above for Structural Formula (I).

In another more specific embodiment for compounds of Structural Formula (VII), Q is O, $CH_2$ or NH, and values and specific values for the remainder of the variables in Structural Formula (VII) are as described above for Structural Formula (I).

In a 21$^{st}$ specific embodiment, the compound of the present invention is represented by Structural Formula (VII-A):

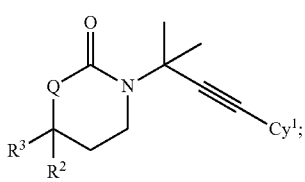

(VII-A)

or a pharmaceutically acceptable salt, enantiomer or diastereomer thereof.

The values and specific values for the variables in Structural Formula (VII-A) are as described above for Structural Formula (VII).

In a more specific embodiment for compounds of Structural Formula (VII-A), Q is O, $CH_2$ or NH, $Cy^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyrimidinyl, oxodihydropyrazinyl, oxodihydropyridazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and values and specific values for the remainder of the variables in Structural Formula (VII-A) are as described above for Structural Formula (I).

In a 22$^{nd}$ specific embodiment, the compound of the present invention is represented by Structural Formula (VII-B):

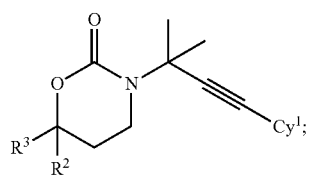

(VII-B)

or a pharmaceutically acceptable salt, enantiomer or diastereomer thereof.

The values and specific values for the variables in Structural Formula (VII-B) are as described above for Structural Formula (VII-A).

In a more specific embodiment for compounds of Structural Formula (VII-B), $Cy^1$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group, and values and specific values for the remainder of the variables in Structural Formula (VII-B) are as described above for Structural Formula (I).

In another embodiment of the present invention, for a compound of Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B) (and the more specific embodiment thereunder), or a pharmaceutically acceptable salt, enantiomer or diastereomer thereof, $R^3$ is $(C_3-C_6)$alkenyl, hydroxy$(C_2-C_5)$alkyl, cyano$(C_2-C_5)$alkyl, dihydroxy$(C_3-C_5)$alkyl, $\omega$-$H_2NCO(C_1-C_5)$alkyl, $(C_1-C_2)$alkoxy$(C_1-C_4)$alkyl, $H_2NSO_2O(C_2-C_5)$alkyl, $H_2NSO_2NH(C_2-C_5)$alkyl, oxo$(C_2-C_5)$alkyl, MeC(=O)NH$(C_2-C_5)$alkyl, MeSO$_2$NH$(C_2-C_5)$alkyl, or MeSO$_2$NH$(C_2-C_5)$alkyl, and values and particular or specific values for the remainder of the variables in Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively, are as described above for Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively.

In another embodiment of the present invention, for a compound of Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), (and the more specific embodiments thereunder), or a pharmaceutically acceptable salt, enantiomer or diastereomer thereof, $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, $HO_2C$—, $(HO)_2P(=O)O$—, $H_2NS(=O)_2O$—, $H_2NS(=O)_2NH$—, MeNHC(=O)NH—, MeNHC(=O)O—, oxo, cyano, $HO_2C$—, $HOCH_2CH_2NH$—, 4-morpholino, $HOCH_2C(=O)NH$—, $H_2NCH_2C(=O)NH$—, EtNHC(=O)NH, MeOC(=O)NH—, MeNHC(=NC≡N)NH—, MeS—, $MeSO_2$—, $MeSO_2N(Me)$-, $MeS(=O)_2NHC(=O)$—, imidazolylamino-, imidazolyl, tetrazolyl, spirocyclopropyl, $FCH_2CH_2NH$, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2NCONH$—, $H_2NCO_2$—, $HOCH_2CH_2O$—, MeNH—, $Me_2N$— and MeCONMe, and values and particular or specific values for the remainder of the variables in Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively, are as described above for Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively.

In another embodiment of the present invention, for a compound of Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B) (and the more specific embodiments thereunder), or a pharmaceutically acceptable salt, enantiomer or diastereomer thereof, $R^2$ is an optionally substituted $(C_1-C_6)$alkyl, aryl, heteroaryl or cycloalkyl group; each optionally substituted with up to four groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkythio; E is a bond or $CH_2$; $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, $HO_2C$—, MeNHC(=O)NH—, oxo, cyano, $HOCH_2C(=O)NH$—, EtNHC(=O)NH, MeS—, $MeSO_2$— $MeSO_2N(Me)$-, 2-oxo-1-pyrrolidinyl, $H_2NCONH$—, $H_2NCO_2$—, $HOCH_2CH_2O$—, MeNH—, $Me_2N$— and MeCONMe, and values and particular or specific values for the remainder of the variables in Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively, are as described above for Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively.

In another embodiment of the present invention, for a compound of Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B) (and the more specific embodiments thereunder), or a pharmaceutically acceptable salt, enantiomer or diastereomer thereof, $R^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen, cyano and nitro; $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, HO$_2$C—, MeNHC(=O)NH—, oxo, cyano, HOCH$_2$C(=O)NH—, EtNHC(=O)NH, MeS—, MeSO$_2$—MeSO$_2$N(Me)-, 2-oxo-1-pyrrolidinyl, H$_2$NCONH—, H$_2$NCO$_2$—, HOCH$_2$CH$_2$O—, MeNH—, Me$_2$N— and MeCONMe; the group represented by Cy$^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl; and the group represented by Cy$^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, carbamoyl, methyl-carbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylamino-sulfonyl, pyrrolidine-1-sulfonyl, methylsulfonyl-aminomethyl, tetrazolyl, trifluoromethyl, acetyl, 2-hydroxyethyl, 1-aminoethyl, deuteromethyl, t-butyl, difluoromethyl, 2-fluoroethyl, 2,2,2-trifluoroethyl, 2-hydroxy-2-propyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, methylthio, and values and particular or specific values for the remainder of the variables in Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively, are as described above for Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively.

In another embodiment of the present invention, for a compound of Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B) (and the more specific embodiments thereunder), or a pharmaceutically acceptable salt, enantiomer or diastereomer thereof, R$^2$ is phenyl optionally substituted with one to three groups independently selected from (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; R$^3$ is 2-methylallyl, MeSO$_2$NHCH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl; the group represented by Cy$^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl; and the group represented by Cy$^2$ is optionally substituted 1 to 4 groups independently selected from methyl, ethyl, propyl, cyclopropyl, halo, hydroxy, methoxy, hydroxymethyl, methoxycarbonyl, amino, aminomethyl, carbamoyl, methyl-carbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylamino-sulfonyl, pyrrolidine-1-sulfonyl, methylsulfonyl-aminomethyl, tetrazolyl, trifluoromethyl, acetyl, 2-hydroxyethyl and 1-aminoethyl, deuteromethyl, t-butyl, difluoromethyl, 2-fluoroethyl, 2,2,2-trifluoroethyl, 2-hydroxy-2-propyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, methylthio, and values and particular or specific values for the remainder of the variables in Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively, are as described above for Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively.

In another embodiment of the present invention, for a compound of Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B) (and the more specific embodiments thereunder), or a pharmaceutically acceptable salt, enantiomer or diastereomer thereof, R$^2$ is phenyl or fluorophenyl; R$^3$ is 2-methylallyl, 2-hydroxy-2-methylpropyl or 2-cyano-2-methylpropyl; and the groups represented by Cy$^1$ and Cy$^2$ (i.e., the oxodihydropyridyl group for Structural Formulas (III), (III-A), (III-B), (V), (V-A) and (V-B)), if present, are each, independently, optionally substituted with fluoro, chloro, cyano, CONH$_2$, CONHMe, CONMe$_2$, CONHc-Pr, methyl, ethyl, cyclopropyl, difluoromethyl, CF$_3$ or oxo, and values and particular or specific values for the remainder of the variables in Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively, are as described above for Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively.

In another embodiment of the present invention, for a compound of Structural Formula (III), (III-A), (III-B), (V), (V-A) or (V-B) (and the more specific embodiments thereunder), or a pharmaceutically acceptable salt, enantiomer or diastereomer thereof, R$^2$ is phenyl or fluorophenyl; R$^3$ is 2-methylallyl, 2-hydroxy-2-methylpropyl or 2-cyano-2-methylpropyl; and the group represented by Cy$^1$ is optionally substituted with fluoro, chloro, cyano, CONH$_2$, CONHMe, CONMe$_2$, CONHc-Pr, methyl, ethyl, cyclopropyl, difluoromethane, CF$_3$ or oxo; m is 0, 1 or 2; G is (C$_1$-C$_6$)alkyl, halo(C$_1$-C$_6$)alkyl or (C$_3$-C$_6$)cycloalkyl; and values and particular or specific values for the remainder of the variables in Structural Formula (III), (III-A), (III-B), (V), (V-A) or (V-B), respectively, are as described above for Structural Formula (III), (III-A), (III-B), (V), (V-A) or (V-B), respectively.

In another embodiment of the present invention, for a compound of Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B) (and the more specific embodiments thereunder), or a pharmaceutically acceptable salt, enantiomer or diastereomer thereof, R$^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen, cyano and nitro; $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, $HO_2$C—, MeNHC(=O)NH—, oxo, cyano, $HOCH_2$C(=O)NH—, EtNHC(=O)NH, MeS—, $MeSO_2$—$MeSO_2$N(Me)-, 2-oxo-1-pyrrolidinyl, $H_2$NCONH—, $H_2$NCO$_2$—, $HOCH_2CH_2$O—, MeNH—, $Me_2$N— and MeCONMe; the group represented by the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, 2-hydroxyethyl, 2-hydroxy-2-propyl, methoxymethyl, methylsulfonyl, methylsulfonylamino, benzyloxycarbonyl, ethyl, propyl, cyclopropyl, halo, hydroxymethyl, methoxycarbonyl, amino, aminomethyl, carbamoyl, methyl-carbamoyl, dimethylcarbamoyl, (2-methoxyethyl)aminocarbonyl, acetylaminomethyl, methylaminosulfonyl, isopropylaminosulfonyl, dimethylaminosulfonyl, pyrrolidine-1-sulfonyl, methylsulfonyl-aminomethyl, tetrazolyl, acetyl, 1-aminoethyl, deuteromethyl, t-butyl, difluoromethyl, 2-fluoroethyl, 2,2,2-trifluoroethyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, methylthio, and values and particular or specific values for the remainder of the variables in Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively, are as described above for Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively.

In another embodiment of the present invention, for a compound of Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B) (and the more specific embodiments thereunder), or a pharmaceutically acceptable salt, enantiomer or diastereomer thereof, $R^2$ is phenyl optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen, cyano and nitro; $R^3$ is 2-methylallyl, $MeSO_2NHCH_2CH_2CH_2$, $H_2$NC(=O)$CH_2CH_2$, $H_2$NC(=O)$CMe_2CH_2$, 3-hydroxypropyl, 3-hydroxy-3-methylbutyl, 2-hydroxyethyl, 2-hydroxy-2-methylpropyl or 2-cyano-2-methylpropyl; the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, 2-hydroxyethyl, 2-hydroxy-2-propyl, methoxymethyl, methylsulfonyl, methylsulfonylamino, benzyloxycarbonyl, ethyl, propyl, cyclopropyl, halo, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylaminosulfonyl, isopropylaminosulfonyl, dimethylaminosulfonyl, pyrrolidine-1-sulfonyl, methylsulfonylaminomethyl, tetrazolyl, acetyl, 1-aminoethyl, deuteromethyl, t-butyl, difluoromethyl, 2-fluoroethyl, 2,2,2-trifluoroethyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, methylthio, and values and particular or specific values for the remainder of the variables in Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively, are as described above for Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B), respectively.

Preferred values for the variables in the above-described Structural Formula (I), (II), (II-A), (II-B), (II-C), (II-D), (II-E), (III), (III-A), (III-B), (IV), (IV-A), (IV-B), (IV-C), (IV-D), (V), (V-A), (V-B), (VI), (VI-A), (VI-B), (VII), (VII-A) or (VII-B) are provided below:

Q is O or $CH_2$ and n is 1. Alternatively, Q is O or $NR^5$ and n is 1. Alternatively, Q is O or NH and n is 1. Alternatively, Q is O and n is 1. Alternatively, Q is O or $CH_2$, E is a bond and n is 1. Alternatively, Q is O or $NR^5$, E is a bond and n is 1. Alternatively, Q is O or NH, E is a bond and n is 1. Alternatively, Q is O, E is a bond and n is 1. Alternatively, E is a bond and n is 1. Alternatively, Q is O or $NR^5$ and E is a bond. Alternatively, Q is O or NH and E is a bond. Alternatively, Q is O and E is a bond. Alternatively, Q is O or $CH_2$, n is 1 and $A^1$ is a bond. Alternatively, Q is O or $NR^5$, n is 1 and $A^1$ is a bond. Alternatively, Q is O or NH, n is 1 and $A^1$ is a bond. Alternatively, Q is O, n is 1 and $A^1$ is a bond. Alternatively, Q is O or $CH_2$, E is a bond, n is 1 and $A^1$ is a bond. Alternatively, Q is O or $NR^5$, E is a bond, n is 1 and $A^1$ is a bond. Alternatively, Q is O or NH, E is a bond, n is 1 and $A^1$ is a bond. Alternatively, Q is O, E is a bond, n is 1 and $A^1$ is a bond. Alternatively, E is a bond, n is 1 and $A^1$ is a bond. Alternatively, Q is O or $NR^5$, E is a bond and $A^1$ is a bond. Alternatively, Q is O or NH, E is a bond and $A^1$ is a bond. Alternatively, Q is O, E is a bond and $A^1$ is a bond. Alternatively, Q is O or $CH_2$, n is 1 and $A^2$ is a bond. Alternatively, Q is O or $NR^5$, n is 1 and $A^2$ is a bond. Alternatively, Q is O or NH, n is 1 and $A^2$ is a bond. Alternatively, Q is O, n is 1 and $A^2$ is a bond. Alternatively, Q is O or $CH_2$, E is a bond, n is 1 and $A^2$ is a bond. Alternatively, Q is O or $NR^5$, E is a bond, n is 1 and $A^2$ is a bond. Alternatively, Q is O or NH, E is a bond, n is 1 and $A^2$ is a bond. Alternatively, Q is O, E is a bond, n is 1 and $A^2$ is a bond. Alternatively, E is a bond, n is 1 and $A^2$ is a bond. Alternatively, Q is O or $NR^5$, E is a bond and $A^2$ is a bond. Alternatively, Q is O or NH, E is a bond and $A^2$ is a bond. Alternatively, Q is O, E is a bond and $A^2$ is a bond. Alternatively, Q is O or $CH_2$, n is 1, $A^1$ is a bond and $A^2$ is a bond. Alternatively, Q is O or $NR^5$, n is 1, $A^1$ is a bond and $A^2$ is a bond. Alternatively, Q is O or NH, n is 1, $A^1$ is a bond and $A^2$ is a bond. Alternatively, Q is O, n is 1, $A^1$ is a bond and $A^2$ is a bond. Alternatively, Q is O or $CH_2$, E is a bond, n is 1, $A^1$ is a bond and $A^2$ is a bond. Alternatively, Q is O or $NR^5$, E is a bond, n is 1, $A^1$ is a bond and $A^2$ is a bond. Alternatively, Q is O or NH, E is a bond, n is 1, $A^1$ is a bond and $A^2$ is a bond.

Alternatively, Q is O, E is a bond, n is 1, $A^1$ is a bond and $A^2$ is a bond. Alternatively, E is a bond, n is 1, $A^1$ is a bond and $A^2$ is a bond. Alternatively, Q is O or $NR^5$, E is a bond, $A^1$ is a bond and $A^2$ is a bond. Alternatively, Q is O or NH, E is a bond, $A^1$ is a bond and $A^2$ is a bond. Alternatively, Q is O, E is a bond, $A^1$ is a bond and $A^2$ is a bond. Alternatively, Q is O, $A^1$ is a bond and $A^2$ is a bond.

$R^{1a}$ and $R^{1b}$ are, independently, optionally substituted ($C_1$-$C_6$)alkyl. Alternatively, $R^{1a}$ and $R^{1b}$ are, independently, an optionally substituted methyl or ethyl group. Alternatively, $R^{1a}$ and $R^{1b}$ are, independently, optionally substituted methyl. Alternatively, $R^{1a}$ and $R^{1b}$ are, independently, ($C_1$-$C_6$)alkyl optionally substituted with up to four groups independently selected from fluorine, cyano, oxo, $R^4$, $R^4O$—, $(R^4)2N$—, $R^4O_2O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—. Alternatively, $R^{1a}$ and $R^{1b}$ are, independently, a methyl or ethyl group. the groups represented by $R^{1a}$ and $R^{1b}$ being, independently, optionally substituted with up to four groups independently selected from fluorine, cyano, oxo, $R^4$, $R^4O$—, $(R^4)2N$—, $R^4O_2O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—. Alternatively, $R^{1a}$ and $R^{1b}$ are, independently, methyl optionally substituted with up to four groups independently selected from fluorine, cyano, oxo, $R^4$, $R^4O$—, $(R^4)2N$—, $R^4O_2O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—. Alternatively, $R^{1a}$ is methyl and $R^{1b}$ is ethyl. Alternatively, $R^{1a}$ and $R^{1b}$ are ethyl. Alternatively, $R^{1a}$ and $R^{1b}$ taken together with the carbon to which they are attached form an optionally substituted ($C_3$-$C_6$)cycloalkyl ring. Alternatively, $R^{1a}$ and $R^{1b}$ taken together with the carbon to which they are attached form an optionally substituted cyclopropy or cyclobutyl group. Alternatively, $R^{1a}$ and $R^{1b}$ taken together with the carbon to which they are attached form an optionally substituted cyclopropyl group. Alternatively, $R^{1a}$ and $R^{1b}$ taken together with the carbon to which they are attached form an unsubstituted ($C_3$-$C_6$)cycloalkyl ring. Alternatively, $R^{1a}$ and $R^{1b}$ taken together with the carbon to which they are attached form an unsubstituted cyclopropy or cyclobutyl group. Alternatively, $R^{1a}$ and $R^{1b}$ taken together with the carbon to which they are attached form an unsubstituted cyclopropyl group.

Alternatively, $R^{1a}$ and $R^{1b}$ taken together with the carbon to which they are attached form a ($C_3$-$C_6$)cycloalkyl ring optionally substituted with with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—. Alternatively, $R^{1a}$ and $R^{1b}$ taken together with the carbon to which they are attached form a cyclopropy or cyclobutyl group optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

Alternatively, $R^{1a}$ and $R^{1b}$ taken together with the carbon to which they are attached form a cyclopropyl group optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

$Cy^1$ is an optionally substituted aryl, heteroaryl, monocyclic cycloalkyl or monocyclic heterocyclyl group and $Cy^2$ is an optionally substituted aryl, heteroaryl, cycloalkyl or heterocyclyl group. Alternatively, $Cy^1$ is an optionally substituted aryl or heteroaryl group. Alternatively, $Cy^1$ is an optionally substituted aryl. Alternatively, $Cy^1$ is an optionally substituted aryl or heteroaryl group and $Cy^2$ is an optionally substituted aryl, heteroaryl, cycloalkyl or heterocyclyl group. Alternatively, $Cy^1$ is an optionally substituted aryl and $Cy^2$ is an optionally substituted aryl, heteroaryl, cycloalkyl or heterocyclyl group. Alternatively, $Cy^1$ is an optionally substituted aryl, heteroaryl, monocyclic cycloalkyl or monocyclic heterocyclyl group and $Cy^2$ is an optionally substituted aryl or heteroaryl group. Alternatively, $Cy^1$ is an optionally substituted aryl or heteroaryl group and $Cy^2$ is an optionally substituted aryl or heteroaryl group. Alternatively, $Cy^1$ is an optionally substituted aryl and $Cy^2$ is an optionally substituted aryl or heteroaryl group. Alternatively, $Cy^1$ is an optionally substituted aryl and $Cy^2$ is an optionally substituted aryl. Alternatively, $Cy^1$ is an optionally substituted aryl, heteroaryl, monocyclic cycloalkyl or monocyclic heterocyclyl group and $Cy^2$ is H. Alternatively, $Cy^1$ is an optionally substituted aryl or heteroaryl group and $Cy^2$ is H. Alternatively, $Cy^1$ is an optionally substituted aryl and $Cy^2$ is H. $Cy^1$ is an optionally substituted phenyl and $Cy^2$ is an optionally substituted aryl, heteroaryl, cycloalkyl or heterocyclyl group. Alternatively, $Cy^1$ is an optionally substituted phenyl and $Cy^2$ is an optionally substituted aryl or heteroaryl group. Alternatively, $Cy^1$ is an optionally substituted phenyl and $Cy^2$ is an optionally substituted aryl. Alternatively, $Cy^1$ is an optionally substituted phenyl and $Cy^2$ is an optionally substituted aryl. Alternatively, $Cy^1$ is an optionally substituted cyclohexyl, phenyl, pyridyl, pyrimidinyl, thiazolyl, triazolyl or benzothiazolyl group and $Cy^2$ is an optionally substituted aryl, heteroaryl, cycloalkyl or heterocyclyl group. Alternatively, $Cy^1$ is an optionally substituted cyclohexyl, phenyl, pyridyl, pyrimidinyl, thiazolyl, triazolyl or benzothiazolyl group and $Cy^2$ is an optionally substituted aryl or heteroaryl group. Alternatively, $Cy^1$ is an optionally substituted cyclohexyl, phenyl, pyridyl, pyrimidinyl, thiazolyl, triazolyl or benzothiazolyl group and $Cy^2$ is an optionally substituted aryl. Alternatively, $Cy^1$ is an optionally substituted cyclohexyl, phenyl, pyridyl, pyrimidinyl, thiazolyl, triazolyl or benzothiazolyl group and $Cy^2$ is an optionally substituted aryl. Alternatively, $Cy^1$ is an optionally substituted aryl and $Cy^2$ is an optionally substituted phenyl or oxodihydropyridyl group. Alternatively, $Cy^1$ is an optionally substituted cyclohexyl, phenyl, pyridyl, pyrimidinyl, thiazolyl, triazolyl or benzothiazolyl group and $Cy^2$ is an optionally substituted phenyl or oxodihydropyridyl group. Alternatively, $Cy^1$ is an optionally substituted cyclohexyl, phenyl, pyridyl, pyrimidinyl, thiazolyl, triazolyl or benzothiazolyl group and $Cy^2$ is an optionally substituted oxodihydropyridyl group. Alternatively, $Cy^1$ is an optionally substituted phenyl and $Cy^2$ is an optionally substituted phenyl or oxodihydropyridyl group. Alternatively, $Cy^1$ is an optionally substituted phenyl and $Cy^2$ is an optionally substituted oxodihydropyridyl group. Alternatively, $Cy^1$ is an optionally substituted phenyl and $Cy^2$ is an optionally substituted phenyl group. Alternatively, $Cy^1$ is an optionally substituted cyclohexyl, phenyl, pyridyl, pyrimidinyl, thiazolyl, triazolyl or benzothiazolyl group, $Cy^2$ is an optionally substituted phenyl or oxodihydropyridyl group, the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylamino-sulfonyl, pyrrolidine-1-sulfonyl, methylsulfonylaminomethyl, tetrazolyl, trifluoromethyl, acetyl, 2-hydroxyethyl, 1-aminoethyl, deuteromethyl, t-butyl, difluoromethyl, 2-fluoroethyl, 2,2,2-trifluoroethyl, 2-hydroxy-2-propyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, or methylthio.

Alternatively, $Cy^1$ is an optionally substituted phenyl or triazolyl group, $Cy^2$ is an optionally substituted phenyl or oxodihydropyridyl group, and the groups represented by $Cy^1$ and $Cy^2$ are each, independently, optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

Definitions

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

"Alkynyl" is an alkyl group in which at least one carbon-carbon bond has been replaced with a triple bond.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, Spiro [4.4]nonane, adamantyl and the like.

The term "aryl" means an carbocyclic aromatic radical with six to fourteen carbon atoms. Examples include phenyl, a naphthyl, indanyl or a tetrahydronaphthalene. A substituted aryl group has 1-4 substituents. Unless otherwise indicated, exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido. The term "aryl" may be used interchangeably with the terms "aryl ring" "carbocyclic aromatic ring", "aryl group" and "carbocyclic aromatic group".

The term "heteroaryl" means a 5- and 12-membered heteroaromatic radical containing 0-4 heteroatoms selected from N, O, and S. A heteroaryl can be moncyclic or bicyclic, for example, fused to an aryl, moncyclic heteroaryl, heterocyclyl or cycloalkyl group. Examples include 2- or 3-thienyl, 2- or 3-furanyl, 2- or 3- pyrrolyl, 2-,3-, or 4-pyridyl, 2-pyrazinyl, 2-, 4-, or 5-pyrimidinyl, 3- or 4-pyridazinyl, 1 H-indol-6-yl, 1 H-indol-5-yl, 1 H-benzimidazol-6-yl, 1 H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A substitutetd heteroaryl has from 1-4 substituents. Unless otherwise indicated, exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide. The term "heteroaryl", "heteroaromatic", "heteroaryl ring", "heteroaryl group", "heteroaromatic ring", and "heteroaromatic group" are used interchangeably.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2, 2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1 H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1, 6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A substituted heterocyclyl has 1-4 substituents. Unless otherwise indicated, exemplary substituents include alkyl, haloalkyl, halogen and oxo.

The term "spirocycloalkyl" means a cycloalkyl group which shares one ring carbon with another alkyl or cycloalkyl group.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "compound" also includes labeling at one or more positions with deuterium. "Labeled with deuterium at a position" means that the amount deuterium at the position is greater than the amount that is present at natural abundance. In certain instances, the deuterium at each position in a "compound" is at natural abundance.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers, i.e., stereochemically pure. "Stereochemical purity" is the weight of the stereoisomer divided by the combined weight of all of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer divided by the combined weight of the enantiomer and the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
| --- | --- |
| A % | Area percentage |
| Boc | tert-butoxy carbonyl or t-butoxy carbonyl |
| $(Boc)_2O$ | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| dr | diastereomer ratio |
| EDC.HCl, EDCl | 1-[3-(dimethylamino)propyl]-3-ethylcarbodiimide hydrochloride |
| Equiv | equivalents |
| EtOAc | ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or $LiAlH_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| MTBE | methyl t-butyl ether |
| NaH | sodium hydride |
| $NaHCO_3$ | sodium bicarbonate |
| $NaN_3$ | sodium azide |
| NaOH | sodium hydroxide |
| $Na_2SO_4$ | sodium sulfate |
| NMM | N-methylmorpholine |
| NMP | N-methylpyrrolidinone |
| $Pd_2(dba)_3$ | tris(dibenzylideneacetone)dipalladium(0) |
| PE | petroleum ether |
| Quant | quantitative yield |
| rt | room temperature |
| Satd | saturated |
| $SOCl_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |

-continued

| Abbreviation | Meaning |
|---|---|
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilypethoxycarbonyloxy]- |
| Teoc-OSu | 1-[2-(trimethylsilypethoxycarbonyloxy]pyrrolidin-2,5-dione |
| $T_{ext}$ | External temperature |
| $T_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthetic Methods

Compounds of Formula I can be prepared by several processes. In the discussion below, $A^1$, $A^2$, $Cy^1$, $Cy^2$, Q, $R^{1a}$, $R^{1b}$, $R^2$, $R^3$, E, Q and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I, wherein Q=O or NR$^5$, can be prepared by reaction of an aminoalcohol (Q=O) or diamine (Q=NR$^5$) intermediate of Formula 2 with a reagent of Formula 3, wherein $Z^1$ and $Z^2$ are leaving groups such as chloride, 1-imidazolyl or aryloxide in an inert solvent such as THF, CH$_2$Cl$_2$, toluene or MeCN, usually in the presence of an organic or inorganic base such as triethylamine or NaHCO$_3$ respectively, at −10° C. to 120° C.:

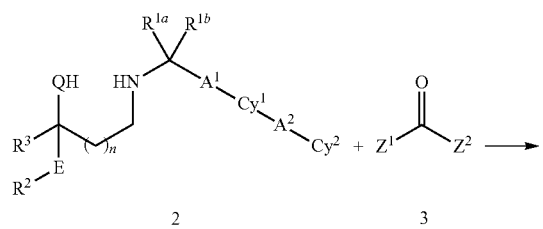

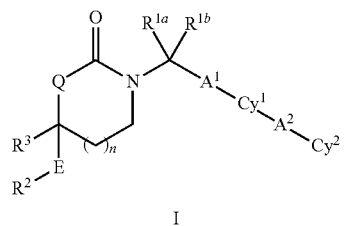

I

Certain instances of reagent 3 are especially convenient because they are commercially available. For example when $Z^1$ and $Z^2$ are both chloride, 3 is phosgene. When $Z^1$ and $Z^2$ are both 1-imidazolyl, 3 is carbonyl diimidazole. When $Z^1$ is chloride and $Z^2$ is p-nitrophenoxide, 3 is p-nitrophenyl chloroformate. When $Z^1$ and $Z^2$ are both OCCl$_3$, 3 is triphosgene and as little as one third of molar equivalent can be used.

Intermediates of Formula 2 can be prepared by reduction of amides of Formula 4 using a hydride reagent such as BH$_3$.THF solution, BH$_3$.Me$_2$S or LiAlH$_4$ in an inert solvent ethereal such as THF or DME at 20° C. to 100° C. for between 1 h and 48 h:

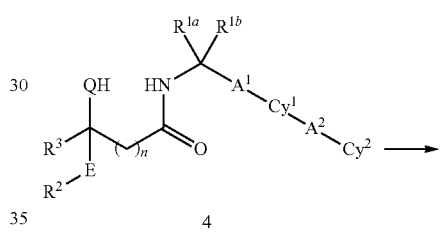

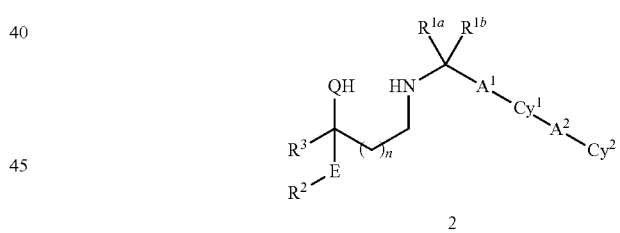

Intermediates of Formula 4, can be prepared by coupling of an α-, β- or γ-hydroxyacid of Formula 5 (Q=O) or a protected α-, β- or γ-aminoacid of Formula 5 (Q=NR$^5$) with an amine of Formula 6 using standard peptide coupling reagents such as EDC in the presence of HOBt and N,N-diisopropylethylamine in an inert solvent such as CH$_2$Cl$_2$ at 0-30° C. for between 1 h and 24 h:

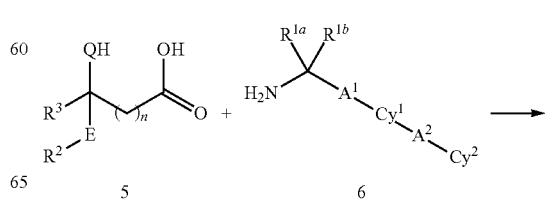

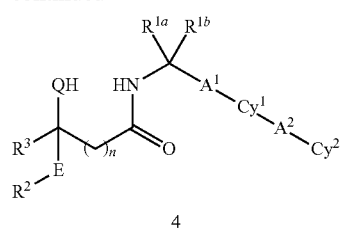

4

Amines of Formula 6 can be prepared by Ritter reaction of alcohols of Formula 7 with HCN:

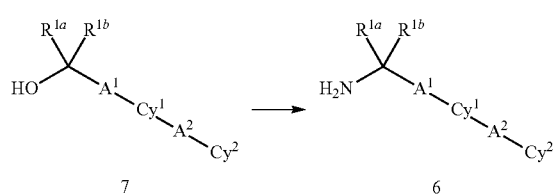

Amines of Formula 6, wherein $R^{1a}$=$R^{1b}$, can be prepared by double addition of organometallic reagents of Formula 8, wherein M is preferably Li, to nitriles of Formula 9:

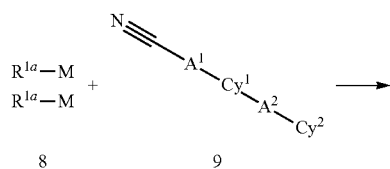

Amines of Formula 6 can also be prepared by Hoffman or Curtius rearrangement of carboxylic acids of Formula 10, using for example diphenylphosphoryl azide:

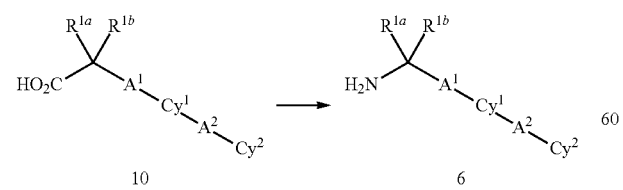

Intermediates of Formula 2, wherein Q=O and n=0 or 1, can be prepared by reaction of epoxides (n=0) or oxetanes (n=1) of Formula 11 with amines of Formula 6:

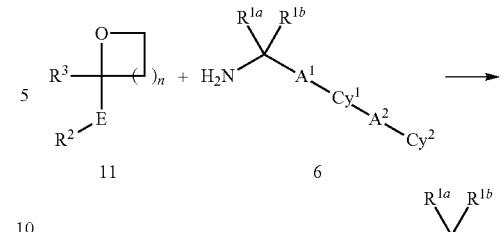

Intermediates of Formula 2, wherein Q=O or protected $NR^5$, can also be prepared by reductive amination of aldehydes of Formula 12 with amines of Formula 6. Methods for the reductive amination of aldehydes are described in Baxter, E. W. and Reitz, A. B. "Organic Reactions" Volume 59, Ed. Overman, L. E., Wiley Interscience, 2002.

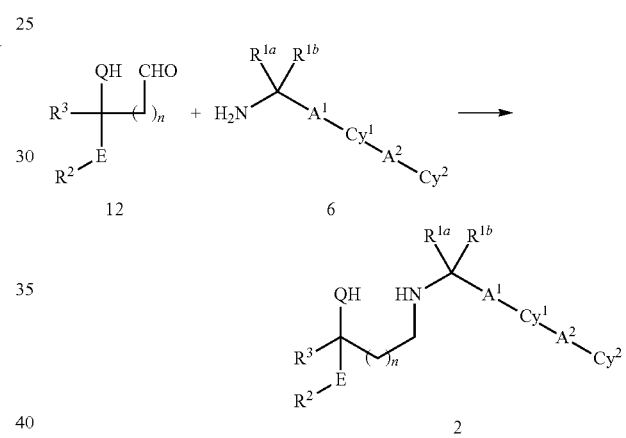

Amine intermediates of Formula 2, wherein Q=O or protected $NR^5$, can be prepared by reaction of halides or sulfonates of Formula 13, wherein $R^E$ is halide or $OSO_2R^A$ ($R^A$=alkyl, haloalkyl or arylalkyl), with amines of Formula 6:

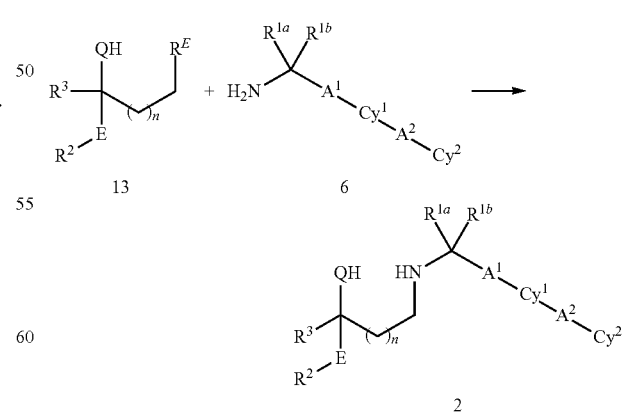

Sulfonate intermediates of Formula 13, wherein Q=O and $R^E$=$OSO_2R^A$, can be prepared from diol intermediates of Formula 14 with a sulfonyl chloride $R^ASO_2Cl$:

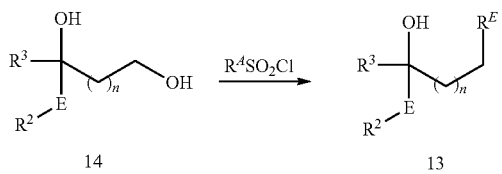

Diol intermediates of Formula 14, wherein n=1, can be prepared by hydroboration of allyl alcohols of Formula 15:

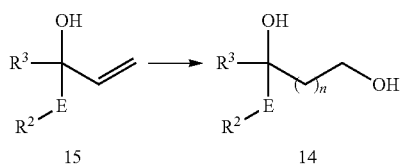

(n = 1)

Diol intermediates of Formula 14, wherein n=0, can be prepared by ozonolysis and reduction of allyl alcohols of Formula 15:

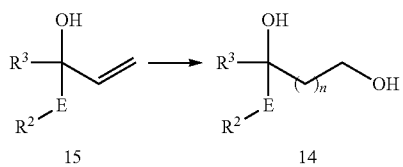

(n = 0)

Halide intermediates of Formula 13, wherein n=1 and $R^E$ is chloride can be prepared by addition of an organometallic reagent Formula 16, wherein M is Li, MgCl, MgBr, MgI, ZnI optionally in the presence of $CeCl_3$, with a ketone intermediate of Formula 17:

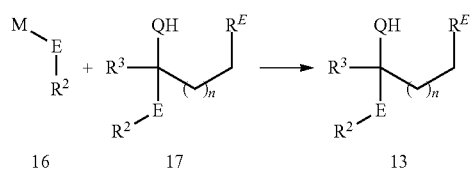

In a second process a compound of Formula I, wherein Q=O and n=0 or 1, can be prepared by reaction of a hydroxycarbamate of Formula 18, wherein $R^B$ is alkyl or arylalkyl group such as methyl, t-butyl or benzyl, with a strong base such as NaH:

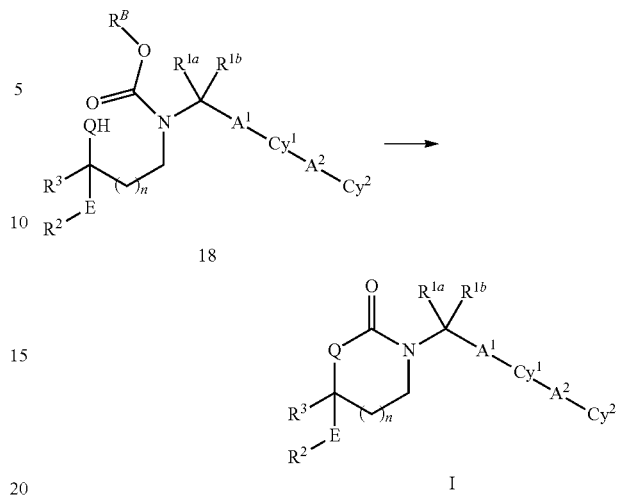

A hydroxycarbamate of Formula 18 can be prepared by reaction of an amine of Formula 2, wherein Q=O, with a chloroformate of Formula $R^B OCOCl$ or when $R^B$=t-Bu with $Boc_2O$.

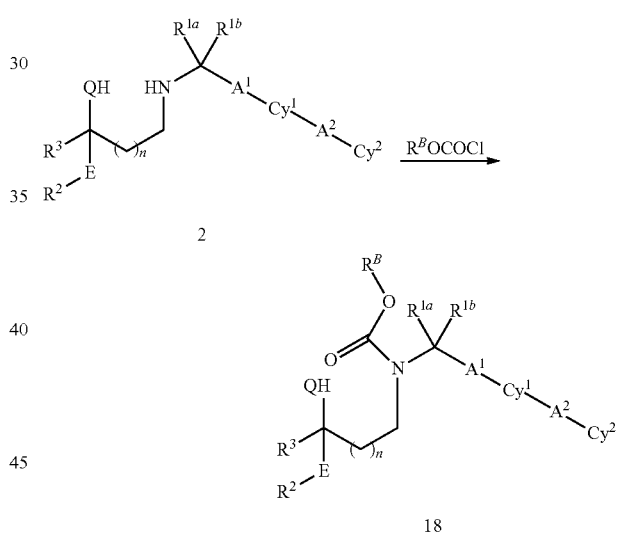

In a third process a compound of Formula I can be prepared by reaction of a ketocarbamate of Formula 19, wherein $R^B$ is alkyl or arylalkyl group such as methyl, t-butyl or benzyl, with an organometallic reagent of Formula 20 wherein M includes, but is not limited to, MgCl, MgBr, MgI or Li:

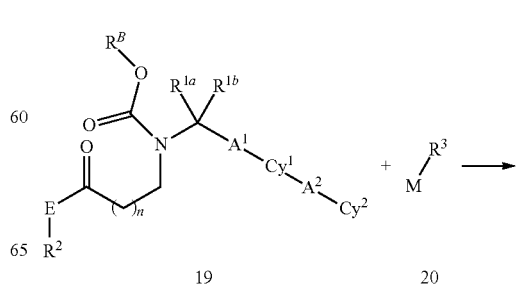

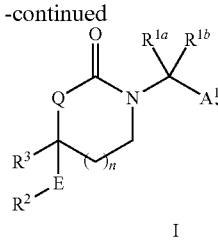

I

In specific examples, organometallic reagent 20 is allylmagnesium bromide, allylzinc(II) bromide, (2-methylallyl)magnesium chloride or (2-methoxy-2-oxoethyl)zinc(II) bromide. In certain cases when M is MgCl, MgBr or MgI, it is advantageous to add CeCl₃ to the reaction mixture.

Ketocarbamates of Formula 19 can be prepared by reaction of aminoketones of Formula 21 with intermediates of Formula 22 wherein $R^C$ is a leaving group such as chloride, succinyloxy, imidazolyl or t-butoxycarboxycarbonyl:

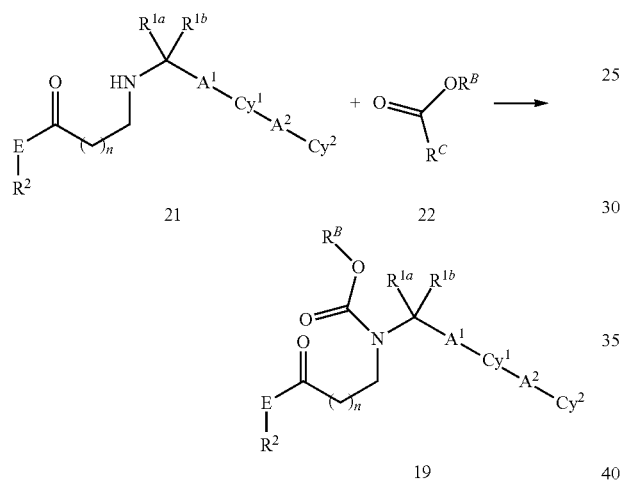

Aminoketones of Formula 21, wherein n=1, can be prepared by reaction of α,β-unsaturated ketones of Formula 23 with amines of Formula 6:

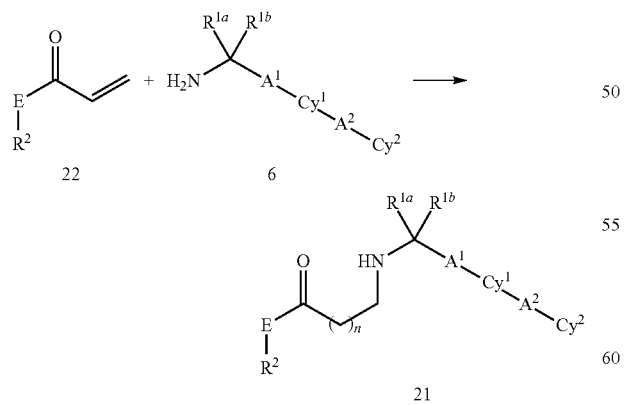

Aminoketones of Formula 21, wherein n=1, can be prepared by reaction of β-dialkylaminoketones of Formula 23, wherein $R^E$ is lower alkyl especially methyl, with amines of Formula 6:

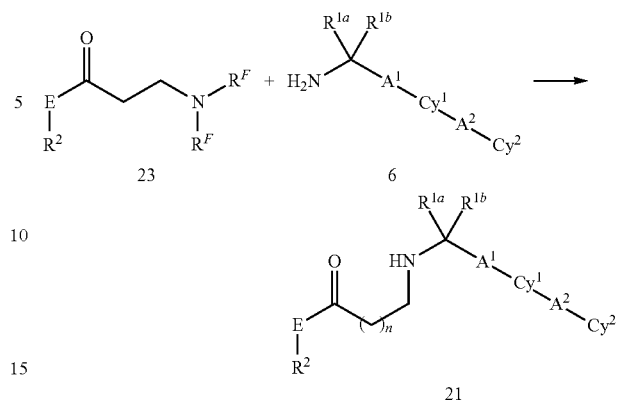

β-Dialkylaminoketones of Formula 23 are in turn derived from α,β-unsaturated ketones of Formula 22 with dialkylamines of Formula $R^F NHR^F$.

Aminoketones of Formula 21, wherein n=0, can be prepared from α-haloketones of Formula 24 and amines of Formula 6:

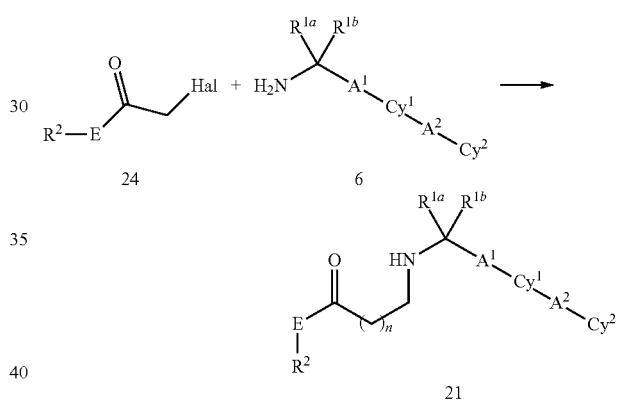

Diamine intermediates of Formula 2, wherein Q=NH, can be prepared by addition of organometallic reagents of Formula 20 to t-butylsulfinylimines of Formula 25:

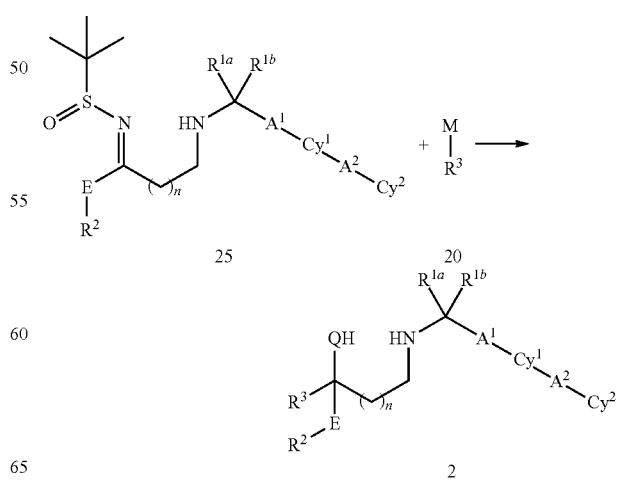

t-Butylsulfinylimines of Formula 25 can be prepared from aminoketones of Formula 21 by reaction with t-butylsulfinamide:

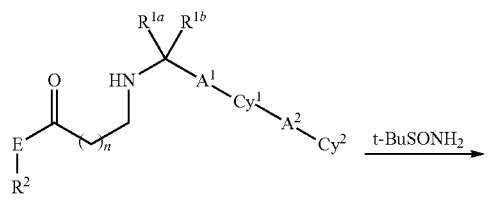

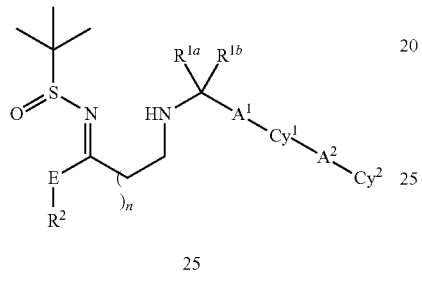

In a fourth process a compound of Formula I, wherein Q=O, can be prepared by reaction of a compound of Formula 23 with an isocyanate of Formula 26 in the presence of a base:

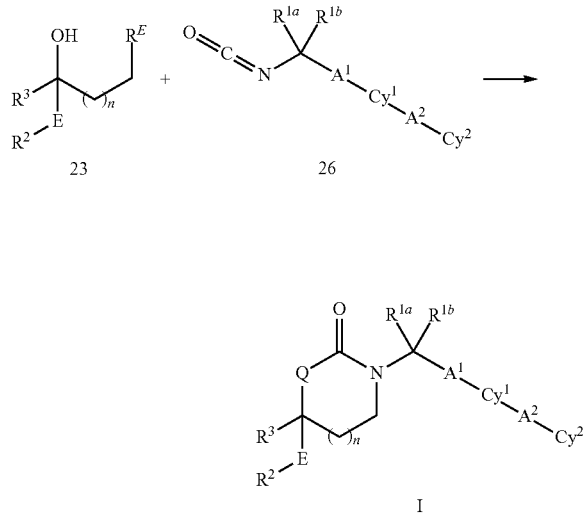

Isocyanates of Formula 26 can be prepared from amines of Formula 6 by treatment with phosgene, diphosgene or triphosgene.

In a fifth process a compound of Formula I, wherein Q=CH$_2$, can be prepared from a compound of Formula 27, wherein R$^B$ is a alkyl or arylalkyl group, especially methyl or ethyl, and R$^E$ is a leaving group such as halide or OSO$_2$R$^A$ (R$^A$=alkyl, haloalkyl or arylalkyl), and an amine of Formula 6:

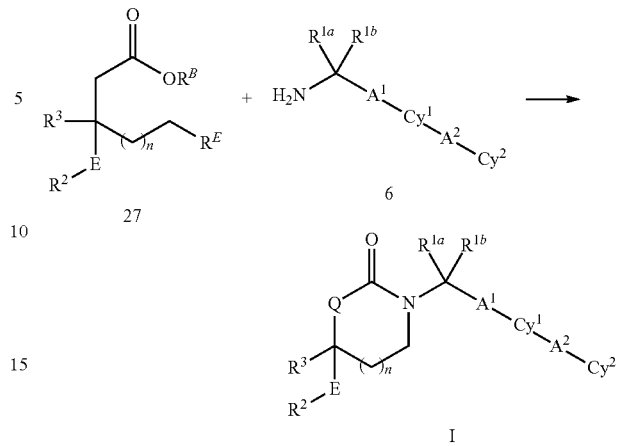

Intermediates of Formula 27, wherein E is a bond, R$^2$ is an aryl or heteroaryl group, R$^E$ is chloro and R$^3$ is allyl, can be prepared from alcohols of Formula 28 by treatment with allyltrimethylsilane in the presence of TiCl$_4$.

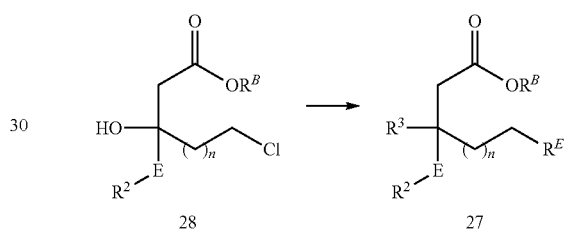

Alcohols of Formula 28 can be prepared by Reformatsky reaction of alkyl bromoacetates of Formula 29 with β-chloroketones of Formula 30.

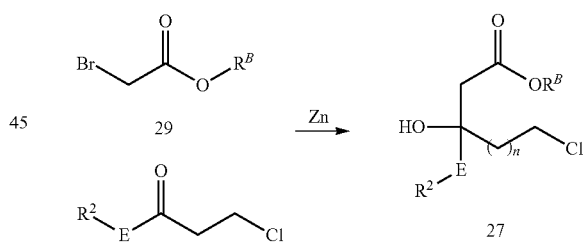

In a sixth process a compound of Formula I, wherein Q=CH$_2$ and R$^3$ is CH$_2$CH$_2$OH, can be prepared from an aminolactone of Formula 32 by heating,

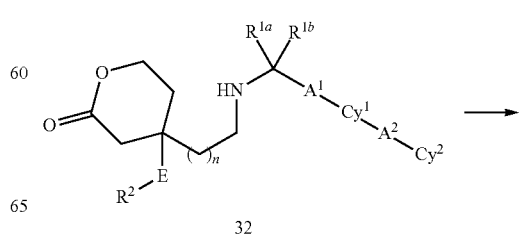

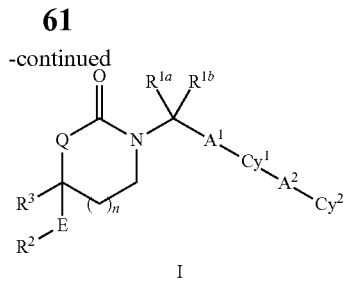

An aminolactone of Formula 32 can be prepared by reductive amination of an aldehyde of Formula 33 with an amine of Formula 6 using, for example, hydride reducing agents such as $NaCNBH_3$ or $NaB(OAc)_3H$.

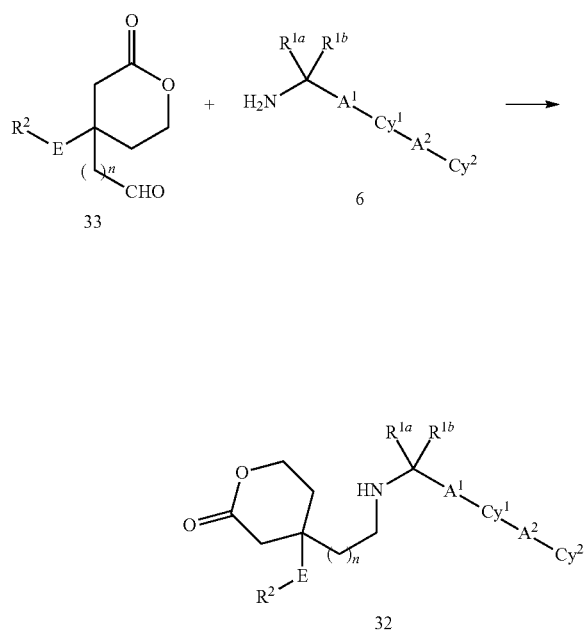

An aldehyde of Formula 33, wherein n=1, can be prepared by ozonolysis followed by mild oxidation of an allyl compound of Formula 34. An aldehyde of Formula 33, wherein n=2, can be prepared by hydroboration followed by mild oxidation of an allyl lactone of Formula 34.

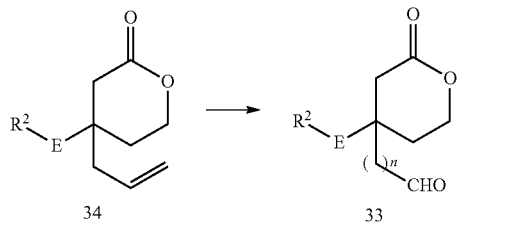

Allyl lactones of Formula 34 can be prepared by heating chloroesters of Formula 35. Chloroesters of Formula 35 can in turn be prepared from hydroxyesters of Formula 36 by treatment with allylsilane in the presence of $TiCl_4$. Hydroxyesters of Formula 36 are available by Reformatsky reaction of α-bromoacetates of Formula 37 and β-chloroketones of Formula 38.

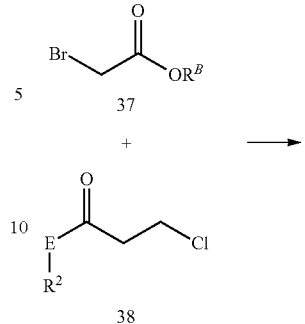

In a seventh process, a compound of Formula I, wherein $A^2$ is a bond and $Cy^1$ and $Cy^2$ are both independently selected to be aryl or heteroaryl can be prepared by Suzuki coupling of 39, wherein $R^J$=trifluoromethanesulfonyloxy, chloro, bromo or iodo and 40, wherein $R^K$ is H or alkyl or $B(OR^K)_2$=4,4,5,5-tetramethyl-1,3,2-dioxaborolan-2-yl in the presence of a palladium catalyst.

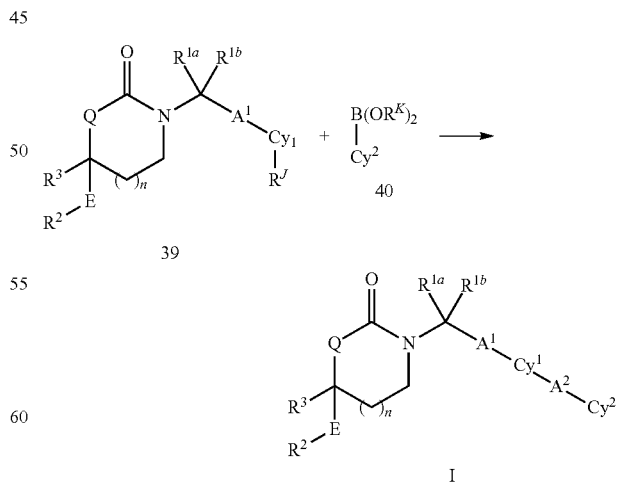

Alternatively a boron compound of Formula 41 may be reacted with compound of Formula 42, wherein $R^J$ and $R^K$ are as defined immediately above.

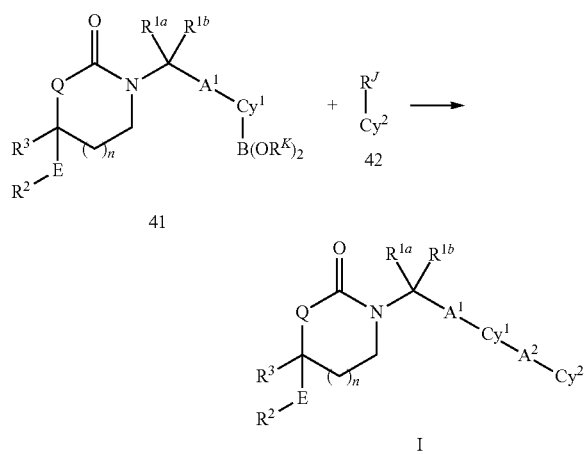

Boron compounds of Formula 41 can be prepared from compounds of Formula 39, wherein $R^J$ is bromine or iodine.

In an eighth process, a compound of Formula I, wherein $A^1$ is ethynyl, can be prepared by Sonogashira coupling of a compound of Formula 43 with a compound of Formula 44, wherein $R^J$ is as defined above:

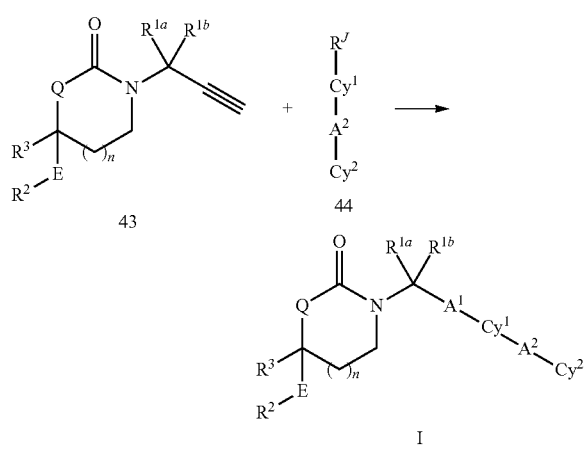

In a ninth process a compound of Formula I can be prepared from another compound of Formula I. For example:

(1) a compound of Formula I wherein $R^{1a}$, $R^{1b}$ or $R^3$ is $\omega$-hydroxy($C_2$-$C_6$)alkyl can be oxidized to a compound of Formula I wherein $R^{1a}$, $R^{1b}$ or $R^3$ is $\omega$-carboxy($C_1$-$C_6$)alkyl using Jones reagent.

(2) a compound of Formula I wherein $R^{1a}$, $R^{1b}$ or $R^3$ is $\omega$-carboxy($C_1$-$C_6$)alkyl can be coupled with ammonia or a ($C_1$-$C_6$)alkylamine using a standard peptide coupling reagent such as EDC to afford a compound of Formula I wherein $R^{1a}$, $R^{1b}$, or $R^3$ is $\omega$-$H_2NC(=O)(C_1$-$C_6)$alkyl or $\omega$-{($C_1$-$C_6$)alkylNHC(=O)}($C_1$-$C_6$)alkyl.

(3) a compound of Formula I wherein $R^{1a}$, $R^{1b}$ or $R^3$ is $\omega$-hydroxy($C_1$-$C_6$)alkyl can be converted to its methanesulfonate or trifluoromethanesulfonate, treated with sodium azide and reduced to give a compound of Formula I, wherein $R^{1a}$, $R^{1b}$ or $R^3$ is $\omega$-amino($C_1$-$C_6$)alkyl.

(4) a compound of Formula I wherein $R^{1a}$, $R^{1b}$ or $R^3$ is amino($C_1$-$C_6$)alkyl can be reacted with acetic anhydride or acetyl chloride to give a compound of Formula I wherein $R^{1a}$, $R^{1b}$ or $R^3$ is {acetylamino}($C_1$-$C_6$)alkyl.

(5) a compound of Formula I wherein $R^{1a}$, $R^{1b}$ or $R^3$ is amino($C_1$-$C_6$)alkyl can be reacted with methanesulfonyl chloride to give a compound of Formula I wherein $R^{1a}$, $R^{1b}$ or $R^3$ is {methanesulfonylamino}($C_1$-$C_6$)alkyl.

(6) a compound of Formula I, wherein $R^{1a}$ or $R^{1b}$ is ($C_2$-$C_6$)alkenyl is hydroborated to afford a compound of Formula I wherein $R^{1a}$ or $R^{1b}$ is hydroxy($C_2$-$C_6$)alkyl.

(7) a compound of Formula I, wherein $R^3$ is ($C_2$-$C_6$)alkenyl, is hydroborated to afford a compound of Formula I wherein $R^3$ is hydroxy($C_2$-$C_6$)alkyl.

(8) a compound of Formula I, wherein $R^{1a}$ or $R^{1b}$ is ($C_2$-$C_6$)alkenyl, can be reacted with osmium tetroxide and N-methylmorpholine-N-oxide to afford a compound of Formula I wherein $R^i$ is vicinal dihydroxy($C_2$-$C_6$)alkyl.

(9) a compound of Formula I, wherein $R^3$ is ($C_2$-$C_6$)alkenyl, can be reacted with osmium tetroxide and N-methylmorpholine-N-oxide to afford a vicinal diol compound of Formula I wherein $R^3$ is vicinal dihydroxy($C_2$-$C_6$)alkyl.

(10) a compound of Formula I, wherein $R^{1a}$ or $R^{1b}$ is ($C_2$-$C_6$)alkenyl, can be reacted with ozone followed by $NaBH_4$ to give a compound of Formula I wherein $R^{1a}$ or $R^{1b}$ is $\omega$-hydroxy($C_1$-$C_5$)alkyl.

(11) a compound of Formula I, wherein $R^3$ is ($C_2$-$C_6$) alkenyl, can be reacted with ozone followed by $NaBH_4$ to give a compound of Formula I wherein $R^3$ is $\omega$-hydroxy($C_1$-$C_5$) alkyl.

(12) a compound of Formula I wherein $R^{1a}$, $R^{1b}$ or $R^3$ is amino($C_1$-$C_6$)alkyl can be reacted with an ($C_1$-$C_6$)alkyl isocyanate to give a compound of Formula I wherein $R^{1a}$, $R^{1b}$ or $R^3$ is ($C_1$-$C_6$)alkylaminocarbonylamino($C_1$-$C_6$)alkyl.

(13) a compound of Formula I wherein $R^{1a}$, $R^{1b}$ or $R^3$ is amino($C_1$-$C_6$)alkyl can be reacted with an ($C_1$-$C_6$)alkyl chloroformate to give a compound of Formula I wherein $R^{1a}$, $R^{1b}$ or $R^3$ is ($C_1$-$C_6$)alkoxycarbonylamino($C_1$-$C_6$)alkyl.

(14) a compound of Formula I wherein $R^{1a}$, $R^{1b}$ or $R^3$ is amino($C_1$-$C_6$)alkyl can be reacted with chlorosulfonyl isocyanate or sulfamide to give a compound of Formula I wherein $R^{1a}$, $R^{1b}$ or $R^3$ is aminosulfonylamino($C_1$-$C_6$)alkyl.

(15) a compound of Formula I wherein $R^{1a}$, $R^{1b}$ or $R^3$ is amino($C_1$-$C_6$)alkyl can be reacted with a ($C_1$-$C_6$)alkylsulfamoyl chloride to give a compound of Formula I wherein $R^{1a}$, $R^{1b}$ or $R^3$ is ($C_1$-$C_6$)alkylaminosulfonylamino($C_1$-$C_6$)alkyl.

(16) a compound of Formula I wherein $R^{1a}$, $R^{1b}$ or $R^3$ is hydroxy($C_1$-$C_6$)alkyl can be reacted with chlorosulfonyl isocyanate to give a compound of Formula I wherein $R^{1a}$, $R^{1b}$ or $R^3$ is aminosulfonyloxy($C_1$-$C_6$)alkyl.

(17) a compound of Formula I wherein $R^{1a}$, $R^{1b}$ or $R^3$ is hydroxy($C_1$-$C_6$)alkyl can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I wherein $R^{1a}$, $R^{1b}$ or $R^3$ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy($C_1$-$C_6$)alkyl.

(18) a compound of Formula I wherein $R^{1a}$, $R^{1b}$ or $R^3$ is hydroxy($C_1$-$C_6$)alkyl can be reacted with $POCl_3$ to give a compound of Formula I wherein $R^{1a}$, $R^{1b}$ or $R^3$ is $(HO)_2P(=O)O(C_1$-$C_6)$alkyl.

(19) a compound of Formula I, wherein $R^3$ is allyl or homoallyl can be reacted with oxygen in the presence of $PdCl_2$ and CuCl to afford a compound of Formula I, wherein $R^3$ is 2-oxopropyl or 3-oxobutyl respectively.

(20) a compound of Formula I wherein $R^3$ is 2-oxopropyl or 3-oxobutyl can be reacted with MeMgX, wherein X is Cl, Br or I, to give a compound of Formula I, wherein $R^3$ is 2-hydroxy-2-methylpropyl or 3-hydroxy-3-methylpropyl respectively.

(21) a compound of Formula I, wherein $R^3$ is —$CH_2CO_2Me$ can be treated with MeMgX, wherein X is Cl, Br or I, to give a compound of Formula I, wherein $R^3$ is 2-hydroxy-2-methylpropyl.

(22) a compound of Formula I, wherein $R^3$ is allyl or —$CH_2C(Me)$=$CH_2$ can be hydrocyanated with TsCN in the presence of triphenylsilane and various cobalt catalysts to afford compounds of Formula I, wherein $R^3$ is —$CH_2CH(CN)Me$ or —$CH_2CMe_2CN$ respectively.

(23) a compound of Formula I, wherein $R^3$ is $CH_2C(Me)_2CN$, can be treated with acetamide in the presence of $PdCl_2$ to give a compound of Formula I, wherein $R^3$ is $CH_2CMe_2CONH_2$.

(24) a compound of Formula I, wherein $R^3$ is —$CH_2C(Me)$=$CH_2$ can be treated with m-CPBA followed by lithium triethylborohydride to afford a compound of Formula I, wherein $R^3$ is 2-hydroxy-2-methylpropyl.

Purification Methods

Compounds of the invention can be purified by high pressure liquid chromatography (prep HPLC). Unless otherwise specified, prep HPLC refers to preparative reverse phase HPLC on a C-18 column eluted with a water/acetonitrile gradient containing 0.01% TFA run on a Gilson 215 system.

LC-MS Methods

Method 1 [LC-MS (3 min)]
Column: Chromolith SpeedRod, RP-18e, 50×4.6 mm; Mobil phase: A: 0.01%TFA/water, B: 0.01%TFA/$CH_3CN$; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

Method 2 (10-80)

| Column | YMC-PACK ODS-AQ, 50 × 2.0 mm 5 μm | |
|---|---|---|
| Mobile Phase | A: water (4 L) + TFA (1.5 mL)) B: acetonitrile (4 L) + TFA (0.75 mL)) | |
| | TIME(min) | A % | B % |
| | 0 | 90 | 10 |
| | 2.2 | 20 | 80 |
| | 2.5 | 20 | 80 |
| Flow Rate | 1 mL/min | |
| Wavelength | UV 220 nm | |
| Oven Temp | 50° C. | |
| MS ionization | ESI | |

Preparation 1

1-chloro-5-methyl-3-phenylhex-5-en-3-ol

Method 1

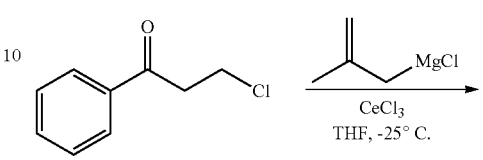

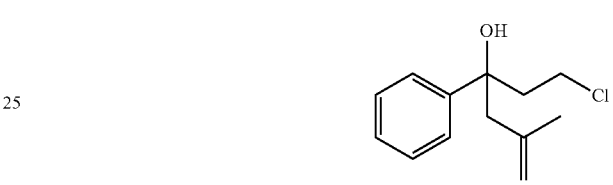

To a stirred suspension of magnesium turnings (46.7 g, 1.94 mol) in 1500 mL of THF ($H_2O$<100 ppm based on Karl Fischer titration) was charged 53.0 mL of 1 M DIBAL-H in hexane under nitrogen at rt. Then 3-chloro-2-methylprop-1-ene (160 g, 1.77 mol) was introduced while maintaining the internal temperature below 30° C. The resulting solution was agitated for 2 h at rt. The solution was titrated in the presence of 1.1'-bipyridine to indicate 0.8 M of the corresponding Grignard reagent. To a dry flask containing 307.0 g of anhydrous $CeCl_3$ (1.25 mol) at rt under nitrogen was added 1556.8 mL of the Grignard reagent (0.8 M, 1.25 mol). The resulting slurry was cooled to −10° C. and agitated for 0.5 h. To the slurry was added 200 g of 3-chloro-1-phenylpropan-1-one (1.19 mol) in 200 mL of THF while maintaining the internal temperature below 0° C. After the mixture was stirred for 0.5 h, 1200 mL of 1 M aq HCl was added to obtain a clear solution while maintaining the internal temperature below 30° C. After the phase cut, the aqueous layer was extracted with EtOAc (500 mL). The combined organic layers were washed with brine and dried over sodium sulfate. Removal of the solvent under vacuum produced crude 1-chloro-5-methyl-3-phenyl-hex-5-en-3-ol, which was chased with THF to achieve $H_2O$<500 ppm based on Karl Fischer titration. The crude product (306 g, 83wt %, 95% yield) was used directly in Step 3. $^1$H-NMR spectroscopy (500 MHz, $CDCl_3$) δ 7.38-7.37 (d. J=7.8 Hz, 2H), 7.33 (t, J=7.9 Hz, 2H), 7.24 (t, J=7.4 Hz, 1 H), 4.91 (s, 1H), 4.76 (s, 1H), 3.57 (ddd, J=5.6, 10.7, and 10.7, 1H), 3.13 (ddd, J=4.7, 10.7 and 10.7 Hz, 1H), 2.66 (d, J=13.3 Hz, 1H), 2.54 (d, J=11.3 Hz, 1H), 2.53 (s, 1H), 2.36 (ddd, J=5.4, 10.6 and 13.9 Hz. 1H), 2.29 (ddd, J=5.6, 11.3 and 13.3 Hz, 1H), 1.29 (s, 3H). $^{13}$C-NMR spectroscopy (125 MHz, $CDCl_3$) δ 144.3, 141.4, 128.0, 126.6, 124.8, 116.1, 74.2, 51.2, 46.0, 39.9, 23.9.

Method 2

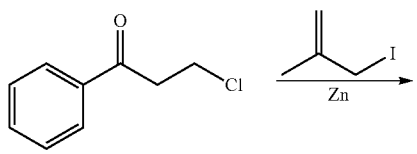

A solution of 3-chloro-1-phenylpropan-1-one (16.8 g, 0.1 mol) in THF (50 mL) was added to a well-stirred suspension of zinc powder (13 g, 0.2 mol) in a mixture of satd aq NH₄Cl solution (260 mL) and THF (65 mL). A solution of 3-iodo-2-methylprop-1-ene (36.4 g, 0.2 mol) in THF (50 mL) was added dropwise. The reaction was mildly exothermic, and the mixture began to reflux spontaneously. After refluxing had ceased, the mixture was stirred for 1 h. TLC showed the 3-chloro-1-phenylpropan-1-one had not reacted completely. A solution of 3-iodo-2-methylprop-1-ene (18.2 g, 0.1 mol) in THF (30 mL) was added, and the mixture was stirred at rt overnight. The mixture was extracted with EtOAc (2×500 mL). The combined organic layer was dried and concentrated. The residue was purified by column chromatography on silica gel eluted with petroleum ether/EtOAc 50:1→30:1→5:1, to give 1-chloro-5-methyl-3-phenylhex-5-en-3-ol (17 g, yield 76%) as an oil.

Preparation 2

Cobalt Catalyst A

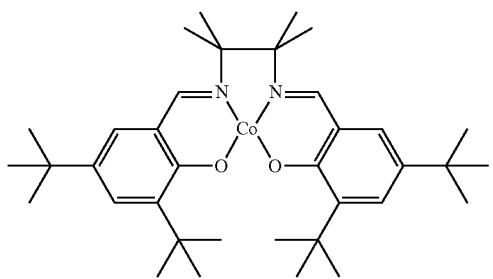

A 50 mL flask was charged with N,N'-bis(3,5-di-tert-butylsalicylidene)-1,1,2,2-tetramethylethenediamine (0.4302 g, 0.78 mmol, 1.0 equiv), EtOH (17 mL), and Co(OAc)₂ (0.1385 g, 0.78 mmol, 1.0 equiv). The mixture was degassed and then heated to reflux under nitrogen for 3 h, cooled to room temperature. The precipitate was filtered and the purple solid was washed with EtOH (10 mL) and dried under high vacuum to give 0.3533 g (75%) of the cobalt(II) complex.

EXAMPLE 1

3-(4-(4-fluorophenyl)-2-methylbut-3-yn-2-yl)-6-(2-methylallyl)-6-phenyl-1,3-oxazinan-2-o

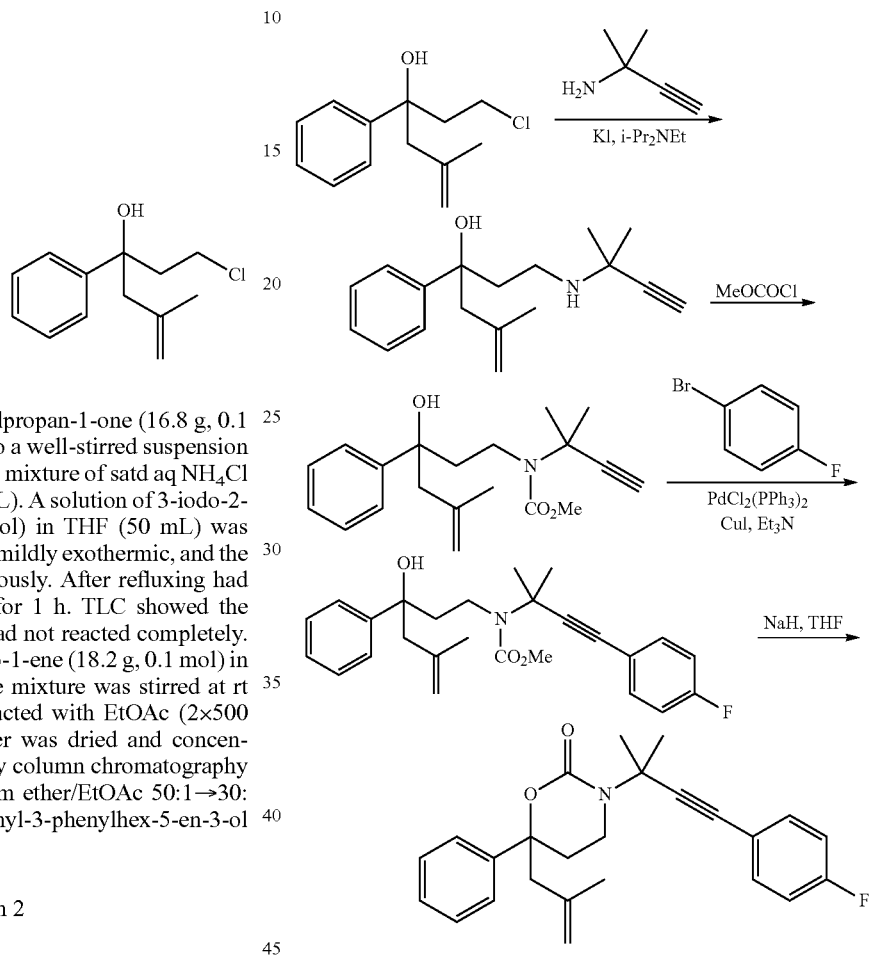

Step 1

A stirred mixture of 1-chloro-5-methyl-3-phenylhex-5-en-3-ol (550 mg, 2.45 mmol), 1,1-dimethylpropargylamine (204 mg, 2.45 mmol), KI (447 mg, 2.7 mmol), i-Pr₂NEt (05 mL, 2.7 mmol) and dry DMF (3 mL) was heated at 80° C. in an oil bath for 24 h. The mixture was concentrated to leave a brown oil which was purified by chromatography on a 12-g silica cartridge eluted with a 0-10% MeOH in CH₂Cl₂ gradient to afford 5-methyl-1-(2-methylbut-3-yn-2-ylamino)-3-phenyl-hex-5-en-3-ol (283 mg, 42%) as a brown solid which was used in the next step without further purification. LC-MS Method 1 $t_R$=1.08 min, m/z=272.

Step 2

A stirred solution of 5-methyl-1-(2-methylbut-3-yn-2-ylamino)-3-phenylhex-5-en-3-ol (283 mg, 1.04 mmol) in CH₂Cl₂ (10 mL) was cooled in an ice bath and i-Pr₂NEt (0.2 mL, 1.1 mmol) was added followed by methyl chloroformate (0.08 mL, 1.05 mmol). The mixture was stirred for 1 h and additional MeOCOCl (0.08 mL, 1.05 mmol) was added. The mixture was allowed to warm to rt and MeOCOCl (0.25 mL, 3.2 mmol) was added followed by DMAP (1 crystal). The mixture was stirred overnight at rt, diluted with EtOAc (90 mL), washed with 5% aq HCl (15 mL), satd aq NaHCO₃ (15 mL) and brine (15 mL), and dried over Na₂SO₄. Removal of the solvent left methyl 3-hydroxy-5-methyl-3-phenylhex-5-enyl(2-methylbut-3-yn-2-yl)carbamate (96 mg, 28%) as a brown oil. LC-MS $t_R$=1.96 min, m/z=352 (M+23), 312 (M−18).

Step 3

A microwave vial equipped with a flea stir bar was charged with 3-hydroxy-5-methyl-3-phenylhex-5-enyl(2-methylbut-3-yn-2-yl)carbamate (37 mg, 0.11 mmol), 1-bromo-4-fluorobenzene (39 mg, 0.22 mmol), CuI (2 mg, 0.011 mmol), Pd(PPh₃)₂Cl₂ (4.7 mg, 0.007 mmol) and Et₃N (1.5 mL). The mixture was sparged with N2 for 5 min and heated at 100 C for 2 h in the microwave. The mixture was concentrated and the residue was redissolved in EtOAc (90 mL), washed with 5% aq HCl (15 mL), satd aq NaHCO₃ (15 mL) and brine (15 mL), and dried over Na₂SO₄. Removal of the solvent left an orange oil (46 mg) which was applied to a 2-g silica SPE cartridge and eluted sequentially with 0, 10, 25, 50 and 100% EtOAc in hexanes (15 mL of each) to give five fractions. Fractions 2 and 3 were pooled and concentrated to afford methyl 4-(4-fluorophenyl)-2-methylbut-3-yn-2-yl(3-hydroxy-5-methyl-3-phenylhex-5-enyl)carbamate (35 mg, 73%) as an oil. LC-MS Method 1 $t_R$=2.33 min, 406 (M−18).

Step 4

To a stirred solution of methyl 4-(4-fluorophenyl)-2-methylbut-3-yn-2-yl(3-hydroxy-5-methyl-3-phenylhex-5-enyl)carbamate (35 mg, 0.03 mmol) in dry THF (2 mL) was added 60% NaH in oil (5 mg, 0.12 mmol). The mixture was heated at 60 C for 3 h, cooled, diluted with EtOAc (90 mL), washed with water (10 mL) and brine (10 mL), and dried over Na₂SO₄. Removal of the solvent left an oil (18 mg) which was purified by prep HPLC to afford 3-(4-(4-fluorophenyl)-2-methylbut-3-yn-2-yl)-6-(2-methylallyl)-6-phenyl-1,3-oxazinan-2-one (17.7 mg, 55%) as an oil. LC-MS Method 1 $t_R$=2.22 min, m/z=392; ¹H NMR (CDCl₃) δ 1.63 (s, 3H), 1.66 (s, 3H), 1.81 (s, 3H), 2.24 (m, 1H), 2.37 (m, 1H), 2.58 (m, 2H), 3.06 (m, 1H), 3.64 (m, 1H), 4.64 (s, 1H), 4.83 (s, 1H), 6.98 (m, 2H), 7.25-7.40 (7H).

EXAMPLE 2

3-(4-(4-fluorophenyl)-2-methylbut-3-yn-2-yl)-6-(2-hydroxy-2-methylpropyl)-6-phenyl-1,3-oxazinan-2-one

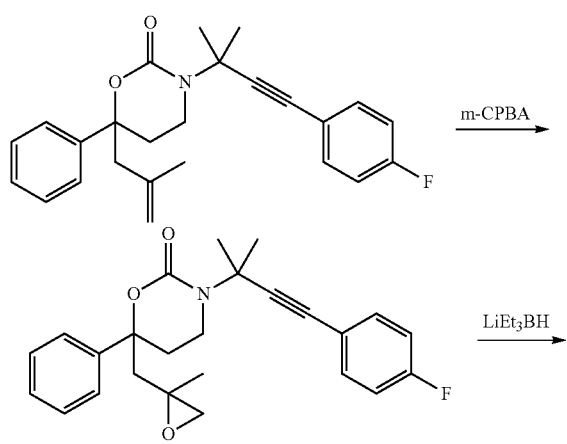

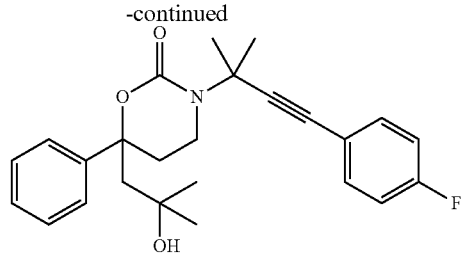

Step 1

To a stirred solution of 3-(4-(4-fluorophenyl)-2-methylbut-3-yn-2-yl)-6-(2-methylallyl)-6-phenyl-1,3-oxazinan-2-one (15 mg, 0.038 mmol) in CH₂Cl₂ at rt was added solid m-CPBA (70%, 13 mg, 50.05 mmol). The mixture was stirred overnight at rt, diluted with EtOAc (100 mL), washed with satd aq NaHCO₃ (10 mL) and brine (10 mL), and dried over Na₂SO₄. Removal of the solvent left 3-(4-(4-fluorophenyl)-2-methylbut-3-yn-2-yl)-6-((2-methyloxiran-2-yl)methyl)-6-phenyl-1,3-oxazinan-2-one (18 mg, quant) as an oil. LC-MS Method 1 $t_R$=1.98 min, m/z=408.

Step 2

A stirred solution of crude 3-(4-(4-fluorophenyl)-2-methylbut-3-yn-2-yl)-6-((2-methyloxiran-2-yl)methyl)-6-phenyl-1,3-oxazinan-2-one (18 mg, ≤0.038 mmol) in dry THF (2 mL) was cooled in an ice bath and 1 M LiEt₃BH in THF (0.2 mL, 0.2 mmol) was added. The mixture was stirred in the ice bath for 3 h and 30% H₂O (1 mL) and water (5 mL) were added. The mixture was diluted with EtOAc (90 mL), washed with brine (10 mL), 30% aq Na₂S₂O₃ (10 mL) and brine (10 mL), and dried over Na₂SO₄. Removal of the solvent left an oil (17 mg) which was purified by prep HPLC to afford 3-(4-(4-fluorophenyl)-2-methylbut-3-yn-2-yl)-6-(2-hydroxy-2-methylpropyl)-6-phenyl-1,3-oxazinan-2-one (6.9 mg) as an oil. LC-MS Method 1 $t_R$=1.90 min, m/z=; ¹H NMR (CDCl₃) δ 1.06 (s, 3H), 1.19 (s, 3H), 1.74 (s, 3H), 1.80 (s, 3H), 2.23 (s, 2H), 2.32 (m, 2H), 2.65 (br s, 1H), 2.91 (m, 1H), 3.62 (m, 1H), 6.97 (m, 2H), 7.25-7.45 (7H).

EXAMPLE 3

3-(2-methyl-4-(1-methyl-2-oxo-1,2-dihydroquinolin-6-yl)but-3-yn-2-yl)-6-(2-methylallyl)-6-phenyl-1,3-oxazinan-2-one The title compound was prepared from methyl 3-hydroxy-5-methyl-3-phenylhex-5-enyl(2-methylbut-3-yn-2-yl)carbamate and 6-bromo-1-methylquinolin-2(1H)-one following procedures analogous to those described in Example 1 Steps 3 and 4. LC-MS Method 1 $t_R$=1.92 min, m/z=455; ¹H NMR (CDCl₃) 1.64 (s, 3H), 1.69 (s, 3H), 1.82 (s, 6H), 2.26 (m, 1H), 2.40 (m, 1H), 2.61 (AB quartet, 2H), 3.08 (m, 1H), 3.64 (m, 1H), 3.71 (s, 3H), 4.64 (s, 1H), 4.83 (s, 1H), 6.77 (d, 1H), 7.25-7.65 (9H).

EXAMPLE 4

6-(2-methylallyl)-6-phenyl-3-(2-(1-phenyl-1H-1,2,3-triazol-4-yl)propan-2-yl)-1,3-oxazinan-2-one

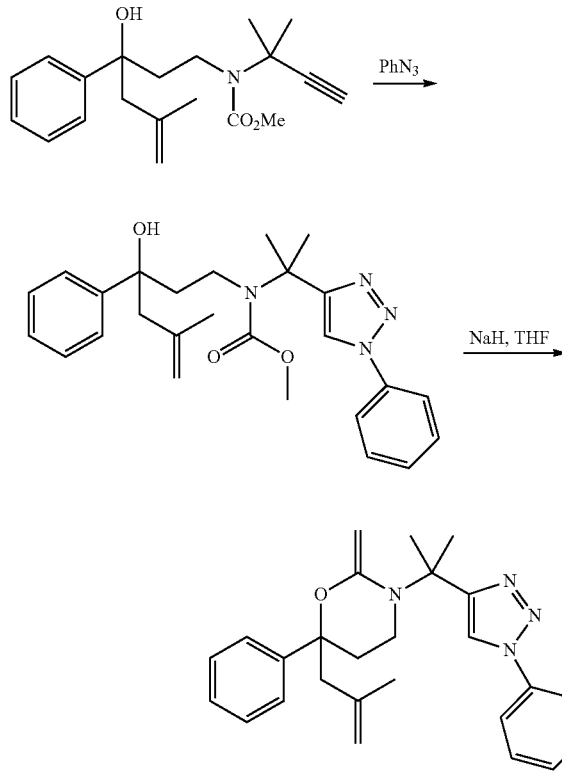

Step 1

To a stirred solution of methyl 3-hydroxy-5-methyl-3-phenylhex-5-enyl(2-methylbut-3-yn-2-yl)carbamate (26 mg, 0.081 mmol) and azidobenzene (29 mg, 0.24 mmol) in $H_2O$ (1 mL) and t-BuOH (1 mL) was added ascorbic acid (3.2 mg, 0.016 mmol) followed by $CuSO_4 \cdot H_2O$ (0.5 mg, 0.002 mmol). The mixture was stirred at rt for 2 d. Additional azidobenzene (29 mg, 0.24 mmol), ascorbic acid (3.2 mg, 0.016 mmol) and $CuSO_4 \cdot 5H_2O$ (0.5 mg, 0.002 mmol) were added. The mixture was stirred for 4 h at rt and purified by prep HPLC to afford methyl 3-hydroxy-5-methyl-3-phenylhex-5-enyl(2-(1-phenyl-1H-1,2,3-triazol-4-yl)propan-2-yl)carbamate (16 mg, 44%) as an oil. LC-MS Method 1 $t_R$=2.00 min, m/z=449.

Step 2

To a stirred solution of methyl 3-hydroxy-5-methyl-3-phenylhex-5-enyl(2-(1-phenyl-1H-1,2,3-triazol-4-yl)propan-2-yl)carbamate (14 mg, 0.031 mmol) in dry THF (1 mL) was added 60% NaH in oil (10 mg, 0.25 mmol). The mixture was heated at 50 C in an oil bath for 1.5 h, cooled, diluted with 5% aq HCl (0.5 mL) and MeOH (0.5 mL) and purified by prep HPLC to afford the title compound (8.7 mg, 67%) as an oil. LC-MS Method 1 $t_R$=1.90 min, m/z=417; $^1$H NMR (CDCl₃) 1.58 (s, 3H), 1.76 (s, 6H), 2.25 (m, 1H), 2.36 (m, 1H), 2.56 (dd, 2H), 3.03 (m, 1H), 3.52 (m, 1H), 4.58 (s, 1H), 4.81 (s, 1H), 7.25-7.80 (11H).

EXAMPLE 5

6-(2-hydroxy-2-methylpropyl)-6-phenyl-3-(2-(1-phenyl-1H-1,2,3-triazol-4-yl)propan-2-yl)-1,3-oxazinan-2-one

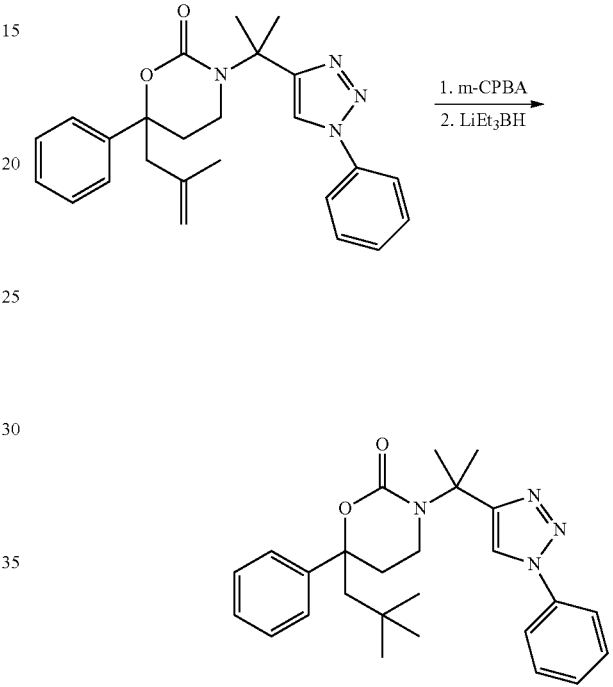

Step 1

To a stirred solution of 6-(2-methylallyl)-6-phenyl-3-(2-(1-phenyl-1H-1,2,3-triazol-4-yl)propan-2-yl)-1,3-oxazinan-2-one (6 mg, 0.014 mmol) in $CH_2Cl_2$ (2 mL) was added solid m-CPBA (10 mg, ≤70%, ≤0.043 mmol). The mixture was stirred overnight at rt, diluted with EtOAc (80 mL), washed with 30% aq $Na_2S_2O_3$ (10 mL), satd aq $NaHCO_3$ (10 mL), 30% aq $Na_2S_2O_3$ (10 mL), satd aq $NaHCO_3$ (10 mL) and brine (10 mL), and dried over $Na_2SO_4$. Removal of the solvent left crude 6-((2-methyloxiran-2-yl)methyl)-6-phenyl-3-(2-(1-phenyl-1H-1,2,3-triazol-4-yl)propan-2-yl)-1,3-oxazinan-2-one (8.4 mg). LC-MS Method 1 $t_R$=1.65 min, m/z=433.

Step 2

A stirred solution of crude 6-((2-methyloxiran-2-yl)methyl)-6-phenyl-3-(2-(1-phenyl-1H-1,2,3-triazol-4-yl)propan-2-yl)-1,3-oxazinan-2-one (8.4 mg, 0.018 mmol) in dry THF (1 mL) was cooled in an ice bath and 1 M LiEt3BH in THF (0.1 mL, 0.1 mmol) was added. The mixture was stirred for 45 min in the ice bath. Water (1 mL) and 30% H2O2 (0.2 mL) were added. The mixture was stirred for 0.5 h and solid Na2S2O3 (~200 mg) was added. The mixture was stirred for 0.5 h and applied to a 10-mL ChemElut cartridge. The cartridge was eluted with EtOAc (50 mL) and the eluate was concentrated to leave a residue which was purified by prep HPLC to afford the title compound (2.5 mg, 42% over 2 steps). LC-MS Method 1 $t_R$=1.57 min, m/z=435.

EXAMPLE 6

3-(1-(4-(1-methyl-2-oxo-1,2-dihydropyridin-4-yl)phenyl)cyclopropyl)-6-(2-methylallyl)-6-phenyl-1,3-oxazinan-2-one

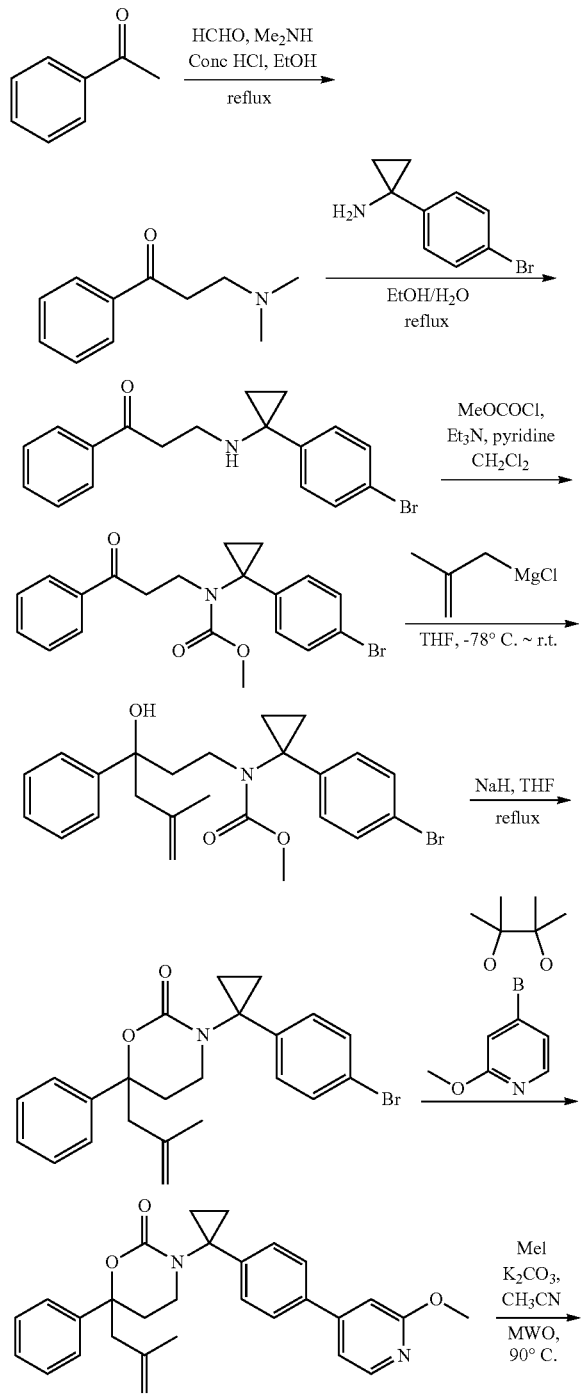

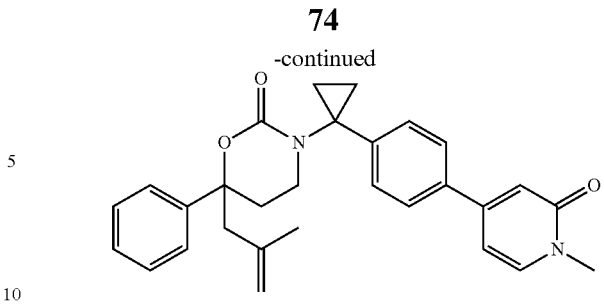

Step 1

The solution of acetophenone (30 g, 0.25 mol) and Me$_2$NH.HCl (0.28 mol) in EtOH (400 mL) was heated at 70° C. overnight. The resulting mixture was concentrated and the residue was washed with EtOAc to give 3-(dimethylamino)-1-phenylpropan-1-one (17.7 g, 40%). $^1$H NMR (400 MHz, CDCl$_3$): δ=2.36 (m, 6H), 2.74 (m, 2H), 3.14 (m, 2H), 7.43 (m, 2H), 7.52 (m, 1H), 7.94 (m, 2H).

Step 2

1-(4-Bromophenyl)cyclopropanamine (150 mg, 0.708 mmol) and 3-(dimethylamino)-1-phenylpropan-1-one (188 mg, 1.5 equiv) were mixed with 1:1 ethanol/water (16 mL) and heated at reflux overnight. After concentration, the residue was extracted with EtOAc (3×7 mL). The combined organic layers were washed with brine (10 mL) and dried over Na$_2$SO$_4$. After filtration and concentration, the residue was purified by chromatography on a 12-g silica gel column, eluted with a 0~10% MeOH in CH$_2$Cl$_2$ gradient to afford crude product (163 mg) which was used in the next step.

Step 3

The crude product from Step 2 (163 mg) was dissolved in CH$_2$Cl$_2$ (10 mL) and cooled to 0° C. Triethylamine (99 μL, 1.5 equiv), pyridine (38 μL, 1 equiv), and methyl chloroformate (300 μL, 8 equiv) were added to the mixture. The ice bath was allowed to melt and the mixture was stirred overnight at rt. The mixture was diluted with ether (50 mL), washed with 5% aq HCl (2×8 mL), satd aq NaHCO$_3$ (7 mL) and brine (5 mL), and dried over Na$_2$SO$_4$. After filtration and concentration, the residue was purified by chromatography on a 12-g silica gel column, eluted with a 5-30% EtOAc in hexanes gradient to afford methyl 1-(4-bromophenyl)cyclopropyl(3-oxo-3-phenylpropyl)carbamate (127.3 mg, 45% yield for 2 steps) as a clear oil.

Step 4

A solution of methyl 1-(4-bromophenyl)cyclopropyl(3-oxo-3-phenylpropyl)carbamate (127 mg, 0.316 mmol) in dry THF (10 mL) was cooled to −78° C. A solution of 0.5M 2-methylallylmagnesium chloride in THF (1.9 mL, 3 equiv) was added. After 10min, the reaction mixture was warmed to rt slowly and stirred for 1 h. LC-MS found the reaction was complete. The mixture was quenched with satd aq NH$_4$Cl (3 mL), diluted with ether (40 mL), washed with 1% aq HCl (8 mL), satd aq NaHCO$_3$ (7 mL), and brine (5 mL), and dried over Na$_2$SO$_4$. After filtration and concentration, the residue was purified by chromatography on a 12-g silica gel column, eluted with a 0~30% EtOAc in hexanes gradient, to afford methyl 1-(4-bromophenyl)cyclopropyl(3-hydroxy-5-methyl-3-phenylhex-5-enyl)carbamate (58.8 mg, 41%).

Step 5

To a solution of methyl 1-(4-bromophenyl)cyclopropyl(3-hydroxy-5-methyl-3-phenylhex-5-enyl)carbamate (58.8 mg, 0.129 mmol) in dry THF (10 mL) was added NaH (60% in mineral oil, 10 mg, 2 equiv). The mixture was heated to reflux for 2 h. LC-MS found the reaction was complete. The mixture was cooled to rt, quenched with satd aq NH$_4$Cl (3 mL), diluted with EtOAc (30 mL), washed with 1% aq HCl (5 mL), satd aq NaHCO₃ solution (5 mL) and brine (4 mL), and dried over Na₂SO₄. After filtration and concentration, the residue was purified by chromatography on a 12-g silica gel column, eluted with a 0~20% EtOAc in hexanes gradient, to afford 3-(1-(4-bromophenyl)cyclopropyl)-6-(2-methylallyl)-6-phenyl-1,3-oxazinan-2-one (33.4 mg, 61%).

Step 6

3-(1-(4-bromophenyl)cyclopropyl)-6-(2-methylallyl)-6-phenyl-1,3-oxazinan-2-one (33 mg, 0.078 mmol), 2-methoxypyridine-4-boronic acid pinacol ester (27 mg, 1.5 equiv), Pd(dppf)Cl₂ (6 mg, 10% mol), 2M aq Na₂CO₃ (1 mL), 1,4-dioxane (2.5 mL) were mixed in a tube for microwave oven. The tube was evacuated and refilled with nitrogen gas (3×) and heated in the microwave oven for 120 min at 130° C. LC-MS found the reaction was complete. The mixture was diluted with EtOAc (10 mL), washed with water (4 mL) and brine (3 mL), and dried over Na₂SO₄. After filtration and concentration, the residue was purified by chromatography on a 4-g silica gel column, eluted with a 10~50% EtOAc in hexanes gradient, to afford 3-(1-(4-(2-methoxypyridin-4-yl)phenyl)cyclopropyl)-6-(2-methylallyl)-6-phenyl-1,3-oxazinan-2-one (26.5 mg, 75%) as a clear oil.

Step 7

A mixture of 3-(1-(4-(2-methoxypyridin-4-yl)phenyl)cyclopropyl)-6-(2-methylallyl)-6-phenyl-1,3-oxazinan-2-one (26.5 mg, 0.058 mmol), K₂CO₃ (16 mg, 2 equiv), iodomethane (250 μL, excess) and acetonitrile (3 mL) was heated at 90° C. for 1.5 h in the microwave oven. LC-MS found the reaction was complete. The mixture was filtered, concentrated, acidified with 5% aq HCl and purified by prep HPLC to afford the title compound (22 mg, 83%). LC-MS Method 1 $t_R$=1.68 min, m/z=455.

EXAMPLE 7

6-(2-hydroxy-2-methylpropyl)-3-(1-(4-(1-methyl-2-oxo-1,2-dihydropyridin-4-yl)phenyl)cyclopropyl)-6-phenyl-1,3-oxazinan-2-one To a solution of 3-(1-(4-(1-methyl-2-oxo-1,2-dihydropyridin-4-yl)phenyl)cyclopropyl)-6-(2-methylallyl)-6-phenyl-1,3-oxazinan-2-one (22 mg, 0.048 mmol) in 2:1 2-Propanol/CH₂Cl₂ (1.5 mL) was added cobalt catalyst A (catalytic amount, c.a. 1 mg), followed by addition of phenylsilane (100 μL, excess). The mixture was stirred vigorously in open air for 1 h. LC-MS found the reaction was complete. The mixture was quenched with 3% aq HCl, filtered, and purified by prep HPLC to afford the title compound (6.8 mg, 30%). LC-MS Method 1 $t_R$=1.37 min., m/z 473 (M+1); ¹H NMR (CD₃OD) δ 7.69(d, 1H), 7.54(d, 2H), 7.42-7.39(m, 5H), 7.13(d, 2H), 6.74(s, 1H), 6.69(d, 1H), 3.59(s, 3H), 3.25(m, 1H), 2.89(m, 1H), 2.67-2.50(m, 2H), 2.19(s, 2H), 1.36-1.20(m, 3H), 1.25 (s, 3H), 1.09(m, 1H), 0.95(s, 3H).

EXAMPLE 8

3-(2-(4-bromophenyl)propan-2-yl)-6-(2-hydroxy-2-methylpropyl)-6-phenyl-1,3-oxazinan-2-one

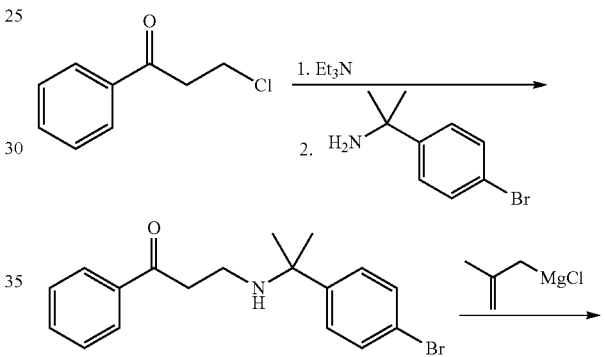

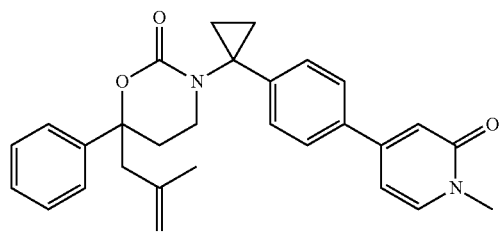 [SMILES: C=C(C)CC1(c2ccccc2)CCN(C2(c3ccc(-c4ccn(C)c(=O)c4)cc3)CC2)C(=O)O1]

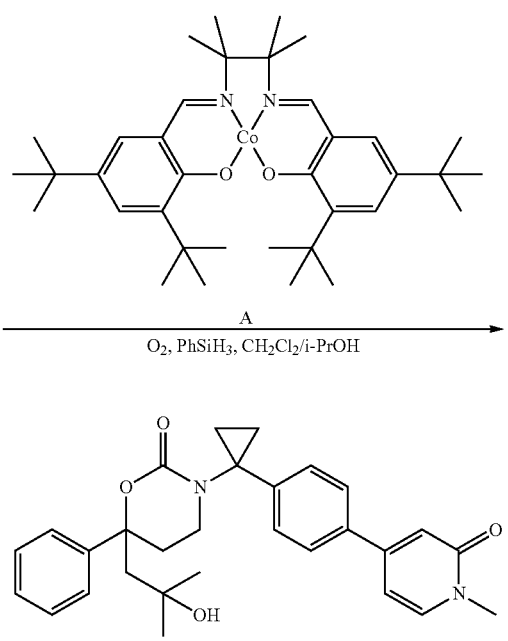

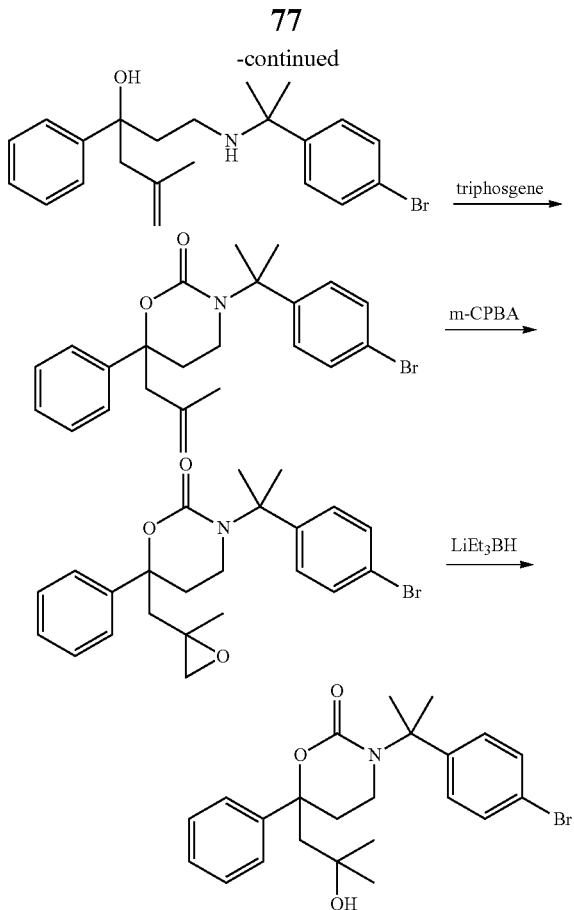

Step 1

To a solution of 3-chloro-1-phenylpropan-1-one (212 mg, 1.26 mmol) in $CH_2Cl_2$ (10 mL) was added $Et_3N$ (381.7 mg, 3.77 mmol) at rt. After addition, the reaction mixture was stirred at rt overnight. The reaction solution was used for the next step directly.

Step 2

To a solution of 2-(4-bromophenyl)propan-2-amine hydrochloride (261 mg, 1.04 mmol) in $CH_2Cl_2$ (5 mL) were added $K_2CO_3$ (290 mg, 2.10 mol) and the solution obtained in Step 1. The mixture was stirred at rt for 4 h. The resulting suspension was filtered, and the filtrate was concentrated under vacuum to give 1-phenyl-3-(2-phenylpropan-2-ylamino)propan-1-one (300 mg, 83%).

Step 3

To a solution of 1-phenyl-3-(2-phenylpropan-2-ylamino) propan-1-one (300 mg, 867 µmol) in THF (5 mL) was added dropwise a solution of (2-methylallyl)magnesium chloride (1 mL, 8 mmol) in THF at −78° C. under nitrogen. After addition, the reaction mixture was stirred at −78° C. for 1 h. The reaction was quenched with satd aq $NH_4Cl$ and extracted with $CH_2Cl_2$ (10 mL×3). The combined organic layers were washed with brine, dried over anhydrous $Na_2SO_4$, filtered and concentrated in vacuo to afford the crude product, which was purified by preparative TLC (petroleum ether: EtOAc=5:1) to afford 1-(2-(4-bromophenyl)propan-2-ylamino)-5-methyl-3-phenylhex-5-en-3-ol (273 mg, 78%).

Step 4

To a solution of 1-(2-(4-bromophenyl)propan-2-ylamino)-5-methyl-3-phenylhex-5-en-3-ol (60 mg, 149.3 µmol) in $CH_2Cl_2$ (15 mL) was added $Et_3N$ (75.5 mg, 746.3 µmol). The mixture was cooled to 0° C. and triphosgene (44.3 mg, 149.3 µmol) was added under nitrogen. The solution was stirred at 0° C. for 1 h. The reaction was quenched with water (15 mL) and extracted with $CH_2Cl_2$ (15 mL×3). The combined organic layers were washed with brine, dried over anhydrous $Na_2SO_4$, and concentrate under vacuum. The residue was purified by preparative TLC (petroleum ether: EtOAc =3:1) followed by preparative HPLC to afford 3-(2-(4-bromophenyl)propan-2-yl)-6-(2-methylallyl)-6-phenyl-1,3-oxazinan-2-one. $^1$H NMR δ 7.45-7.26 (m, 7H), 6.78-6.73 (d, 2H), 4.81 (s, 1H), 4.59 (s, 1H), 3.33-3.27 (m, 1H), 3.05-2.95 (m, 1H), 2.60-2.44 (m, 3H), 2.28-2.18 (m, 1H), 1.65 (s, 3H), 1.59 (s, 3H), 1.41 (s, 3H).

Step 5

To a solution of m-CPBA (49.2 mg, 285 µmol) in $CH_2Cl_2$ (10 mL) was added 3-(2-(4-bromophenyl)propan-2-yl)-6-(2-methylallyl)-6-phenyl-1,3-oxazinan-2-one (61 mg, 142.5 µmol). The reaction mixture was stirred at rt for 1 h. The solution was washed with 30 wt % aqueous sodium thiosulfate (50 mL×3), saturated aqueous sodium bicarbonate and brine successively. The combined organic layers were dried over anhydrous $Na_2SO_4$, filtered and concentrated in vacuo to afford 3-(2-(4-bromophenyl)propan-2-yl)-6-((2-methyloxiran-2-yl)methyl)-6-phenyl-1,3-oxazinan-2-one (57 mg, 90%).

Step 6

To a solution of 3-(2-(4-bromophenyl)propan-2-yl)-6-((2-methyloxiran-2-yl)methyl)-6-phenyl-1,3-oxazinan-2-one (57 mg, 128.4 µmol) in THF (10 mL) was added dropwise $LiBEt_3H$ (642 mL, 642 µmol) at 0° C. under nitrogen. The resulting mixture was stirred at 10° C. for 2 h. The reaction solution was cooled to 0° C. Hydrogen peroxide (10 mL) was added dropwise while maintain the temperature below 25° C. The resulting mixture was diluted with MTBE (50 mL), washed with water (50 mL) and 30 wt % aqueous sodium thiosulfate (50 mL×3). The organic layer was dried over $Na_2SO_4$, filtered and concentrated under vacuum. The residue was purified by preparative HPLC to afford 3-(2-(4-bromophenyl) propan-2-yl)-6-(2-hyroxy-2-ethylpropyl)-6-phenyl-1,3-oxazinan-2-one. $^1$H NMR: ($CDCl_3$) δ 7.45-7.26 (m, 7H), 6.94-6.92 (d, 2H), 3.27-3.24 (m, 1H), 2.85-2.78 (m, 1H), 2.41-2.30 (m, 2H), 2.22 (m, 3H), 1.65 (s, 3H), 1.47 (s, 3H), 1.15 (s, 3H), 1.03 (s, 3H); LC-MS Method 2 $t_R$=1.35 min, m/z=448, 446.

EXAMPLE 9

6-(2-hydroxy-2-methylpropyl)-3-(2-(4-(1-methyl-2-oxo-1,2-dihydropyridin-4-yl)phenyl)propan-2-yl)-6-phenyl-1,3-oxazinan-2-one

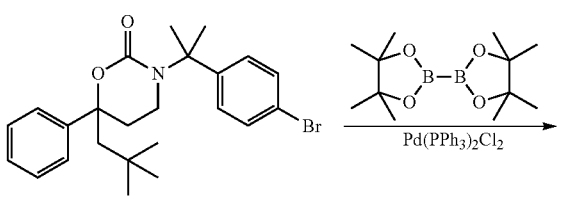

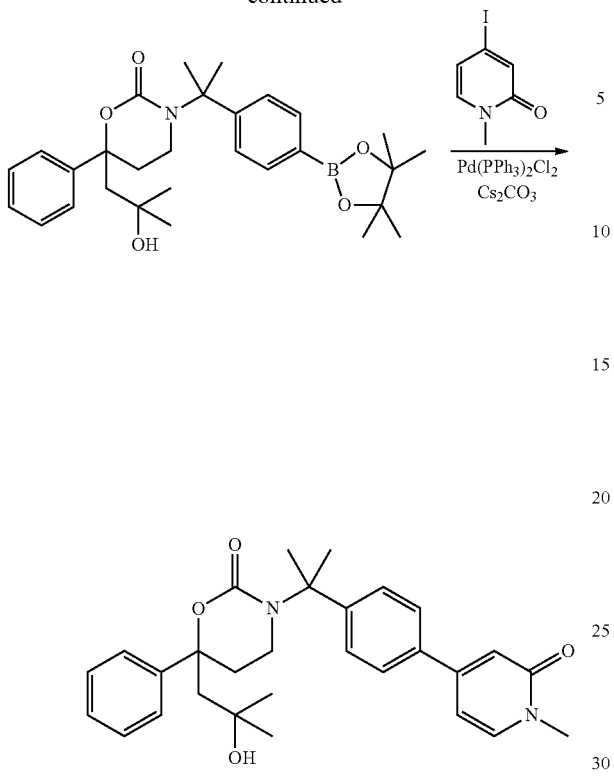

EXAMPLE 10

3-(2-(4-(1-cyclopropyl-2-oxo-1,2-dihydropyridin-4-yl)phenyl)propan-2-yl)-6-(2-hydroxy-2-methylpropyl)-6-phenyl-1,3-oxazinan-2-one

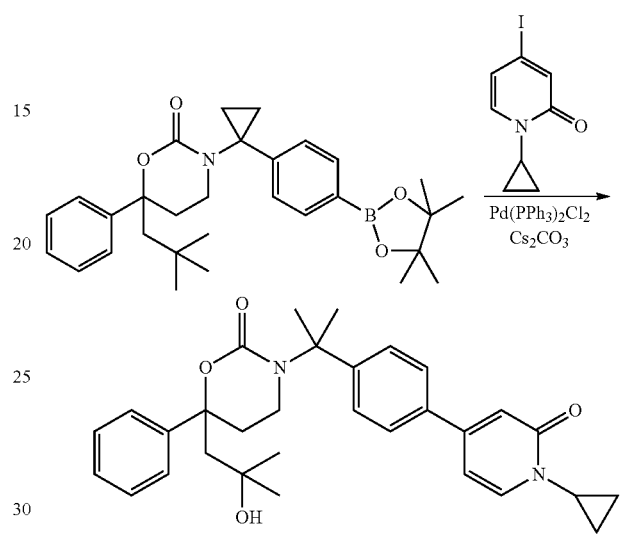

Step 1

To a solution of 33-(2-(4-bromophenyl)propan-2-yl)-6-(2-hyroxy-2-ethylpropyl)-6-phenyl-1,3-oxazinan-2-one (154 mg, 346 μmol) in DMSO (10 mL) were added bis(pinacolato) diboron (439 mg, 1.73 mmol), KOAc (340 mg, 3.5 mmol) and Pd(dppf)Cl$_2$ (5 mg, 7 μmol) under nitrogen. The mixture was stirred at 100° C. for 3 h. The reaction was quenched with water (20 mL) and extracted with EtOAc (10 mL×3). The combined organic layer was washed with water (10 mL'3 3) and brine, dried over Na$_2$SO$_4$, filtered and concentrated under vacuum. The residue was purified by preparative TLC (1:2 petroleum ether/EtOAc) to afford 6-(2-hydroxy-2-methyl-propyl)-6-phenyl-3-(2-(4-(4,4,5,5-tetramethyl-1,3,2-dioxaborolan-2-yl)phenyl)propan-2-yl)-1,3-oxazinan-2-one (128 mg, 75%).

Step 2

To a solution of 6-(2-hydroxy-2-methylpropyl)-6-phenyl-3-(2-(4-(4,4,5,5-tetramethyl-1,3,2-dioxaborolan-2-yl)phenyl)propan-2-yl)-1,3-oxazinan-2-one (30 mg, 60.9 μmol) in toluene (3 mL) was added a solution of sodium carbonate (64.5 mg, 609 μmol) in EtOH (2 mL)/water (1 mL), 4-iodo-1-methylpyridin-2(1H)-one (14.5 mg, 609 μmol) and Pd(PPh$_3$)$_4$ (7.5 mg, 6 μmol) successively under nitrogen. The mixture was stirred at 100° C. for 2.5 h. The reaction mixture was concentrated under vacuum. The residue was dissolved in water, extracted with EtOAc (5 mL×3). The combined organic layers were dried over Na$_2$SO$_4$, filtered and concentrated under vacuum. The crude product was purified by HPLC to afford 6-(2_hydroxy-2-methylpropyl)-3-(2-(4-(1-methyl-2-oxo-dihydropyridin-4-yl)-6-phenyl-1,3-oxazinan-2-one (10.6 mg, 37%). $^1$H NMR (CDCl$_3$) δ 7.40-7.19 (m, 8H), 7.09-7.06 (m, 2H), 6.73 (s, 1H), 6.38-6.36 (d, 1H), 3.51 (s, 3H), 3.27-3.24 (m, 1H), 2.85-2.76 (m, 1H), 2.34-2.21 (m, 2H), 2.16 (s, 2H), 1.65-1.53 (d, 3H), 1.45 (s, 3H), 1.08 (s, 3H), 0.96 (s, 3H); LC-MS Method 2 t$_R$=1.05 min, m/z=475.

To a solution of 6-(2-Hydroxy-2-methyl-propyl)-3-{1-methyl-1-[4-(4,4,5,5-tetramethyl-[1,3,2]dioxaborolan-2-yl)-phenyl]-ethyl}-6-phenyl-[1,3]oxazinan-2-one (50 mg, 151.5 μmol) in DME (10 mL) were added a solution of sodium carbonate (64.5 mg, 609 μmol) in EtOH (2 mL) and water (1 mL), 1-cyclopropyl-4-iodo-1H-pyridin-2-one (19 mg, 73 μmol) and Pd(PPh$_3$)$_4$(7.5 mg, 6 μmol) successively under nitrogen. The reaction mixture was stirred at 100° C. for 2.5 h and then concentrated under vacuum. The residue was dissolved in water, extracted with EtOAc (5 mL×3). The combined organic layers were dried over Na$_2$SO$_4$, filtered and concentrated under vacuum. The crude product was purified by preparative prep HPLC to afford 3-{1-[4-(1-Cyclopropyl-2-oxo-1,2-dihydro-pyridin-4-yl)-phenyl]-1-methyl-ethyl}-6-(2-hydroxy-2-methyl-propyl)-6-phenyl-[1,3]oxazinan-2-one (41 mg, 71%). $^1$H NMR (CDCl$_3$) δ 7.45-7.25 (m, 8H), 7.12-7.10 (d, 2H), 6.75 (s, 1H), 6.40 (d, 1H), 3.39-3.29 (m, 2H), 2.90-2.83 (m, 1H), 2.39-2.21 (m, 4H), 1.67 (d, 3H), 1.50 (s, 3H), 1.16-1.12 (m, 5H), 1.02 (s, 3H), 0.92-0.87 (m, 2H); LC-MS Method 2 t$_R$=1.10 min, m/z=501.

Biological Test Example 1

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 µL of enzyme solution containing microsomes isolated from CHO cells overexpressing human 11β-HSD1 (10-20 µg/ml of total protein) was added, and the plates were incubated for 90 minutes at rt. The reaction was stopped by adding 50 µl of the SPA beads suspension containing 10 µM 18β-glycyrrhetinic acid, 5 mg/ml protein A coated YSi SPA beads (GE Healthcare) and 3.3 µg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

Biological Test Example 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% $CO_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 µL. The cells were pre-incubated with serum-free, phenol-red-free medium containing 0.1% (v/v) of DMSO and various concentrations of the test compounds at least 1 h before [$^3$H] cortisone in ethanol (50Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 µL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE OF BIOLOGICAL ASSAY RESULTS

Biological Test Example 1

| Compound | $IC_{50}$ Range[a] | Average % inhibition at 100 nM | $IC_{50}$ (nM) |
|---|---|---|---|
| Example 1 | ++ | 93.3 | 3.7 |
| Example 2 | ++ | 93.3 | 5.6 |
| Example 3 | ++ | 89.2 | 4.9 |
| Example 4 | ++ | 75.7 | 23 |
| Example 5 | ++ | 70.0 | 39 |
| Example 6 | ++ | 54.5 | 74 |
| Example 7 | # | 15.7 | >100 |
| Example 8 | ++ | 89.6 | 5.3 |
| Example 9 | ++ | 66.9 | 37 |
| Example 10 | ++ | 72.9 | 38 |

[a] ++ means $IC_{50}$ = <100 nM, + means $IC_{50}$ = 100-1000 nM, # means $IC_{50}$ > 100 nM, − means $IC_{50}$ > 1000 nM.

The compounds of the invention are useful for ameliorating or treating disorders or diseases in which decreasing the level of cortisol is effective in treating a disease state. Thus, the compounds of the invention can be used in the treatment or prevention of diabetes mellitus (e.g., type II diabetes), obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypertriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to an 11β-HSD1 inhibitor of the invention, comprise a pharmaceutically acceptable salt of a an 11β-HSD1 inhibitor of the invention and one or more pharmaceutically acceptable carriers therefore. Alternatively, a pharmaceutical composition of the invention may comprise a compound of an 11β-HSD1 inhibitor of the invention or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of an 11β-HSD1 inhibitor of the invention, or an enantiomer, diastereomer, or pharmaceutically acceptable salt thereof or composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of the invention or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1 B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of the invention or composition thereof in a combination therapy with one or more other 11β-HSD1 inhibitors, or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

While this invention has been particularly shown and described with references to example embodiments thereof, it will be understood by those skilled in the art that various changes in form and details may be made therein without departing from the scope of the invention encompassed by the appended claims.

What is claimed is:

1. A compound of Formula (I)

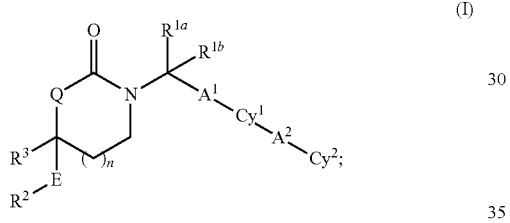

wherein:

$R^{1a}$ and $R^{1b}$ are independently hydrogen, $(C_1-C_6)$alkyl, $(C_2-C_6)$alkenyl, $(C_2-C_6)$alkynyl or $(C_1-C_3)$alkoxy$(C_1-C_3)$alkyl, or $R^{1a}$ and $R^{1b}$ taken together with the carbon to which they are attached form a $(C_3-C_6)$cycloalkyl ring; provided that both $R^{1a}$ and $R^{1b}$ are not hydrogen and if $R^{1a}$ or $R^{1b}$ is hydrogen then $A^1$ is ethynyl; wherein the $(C_1-C_6)$alkyl, $(C_2-C_6)$alkenyl, $(C_2-C_6)$alkynyl, $(C_1-C_3)$alkoxy$(C_1-C_3)$alkyl, or the cycloalkyl ring formed from $R^{1a}$ and $R^{1b}$ and the carbon to which $R^{1a}$ and $R^{1b}$ are attached are, independently, optionally substituted with up to four groups independently selected from fluorine, cyano, oxo, H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)NR^4$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2NR^4$—, $R^4OC(=O)NHS(=O)_2$—, $R^4OC(=O)NHS(=O)_2NR^4$—, $(R^4)_2NC(=O)NHS(=O)_2$—, $(R^4)_2NC(=O)NHS$ $(=O)_2$—, $(R^4)_2NC(=O)NHS(=O)_2NR^4$—, heterocyclyl, heteroaryl, arylamino and heteroarylamino;

$A^1$ is (a) a bond, (b) $(C_1-C_2)$alkylene, $CH_2O$ with the oxygen being attached to $Cy^1$ or $C(=O)$, or (c) ethynyl;

$Cy^1$ is aryl, heteroaryl, monocyclic cycloalkyl or monocyclic heterocyclyl and is optionally substituted with 1 to 4 groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)_2NH_2$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$(=O)S_2N(R^7)_2$, cyano$(C_1-C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=)NR^6R^7$ and —$V^1$—$C(=O)N(R^7)_2$;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl and oxo;

$Cy^2$ is hydrogen, aryl, heteroaryl, cycloalkyl or heterocyclyl and is optionally substituted with 1 to 4 groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, $S(=O)_2R^7$, —$S(=O)_2R^9$, —$NHR^6$, —$N(R^6)$, —$C(=O)R^6$, $C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH_2$, —$V^1$-$NHR^6$, -$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1-C_6)$alkyl, -$V^1$-$C(=O)

$NH_2$, $-V^1-C(=O)NHR^6$, $-V^1-C(=O)N(R^6)_2$, $-V^1-C(=)NHR^7$, $-V^1-C(=O)NR^6R^7$ and $-V^1-C(=O)N(R^7)_2$;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl and oxo;

$R^2$ is $(C_1-C_6)$alkyl, aryl, heteroaryl, cycloalkyl or heterocyclyl and is optionally substituted with up to 4 groups independently selected from halogen, $-CN$, $-NO_2$, $-NH_2$, $-OH$, $-COOH$, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo $(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkythio, $-SR^9$, $-S(=O)R^6$, $-S(=O)R^7$, $-S(=O)R^9$, $-S(=O)_2R^6$, $-S(=O)_2R^7$, $-S(=O)_2R^9$, $-NHR^6$, $-N(R^6)$, $-C(=O)R^6$, $-C(=O)NH_2$, $-S(=O)_2NH_2$, $-C(=O)NHR^6$, $-C(=O)NR^6R^6$, $-C(=O)R^8$, $-S(=O)_2NHR^6$, $-S(=O)_2N(R^6)_2$, $-S(=O)_2R^8$, $-NHC(=O)R^6$, $-V^1-NHC(=O)R^6$, $-NHS(=O)_2R^6$, $-V^1-NHS(=O)_2R^6$, $-V^1-C(=O)R^6$, heteroaryl, aryl, heterocyclyl, oxo, $-V^1-NH2$, $-V^1-NHR^6$, $-V^1-N(R^6)_2$, $-C(=O)R^7$, $-C(=O)NHR^7$, $-C(=O)NR^6R^7$, $-C(=O)N(R^7)_2$, $-S(=O)_2NHR^7$, $-S(=O)_2NR^6R^7$, $-S(=O)_2N(R^7)_2$, cyano$(C_1-C_6)$alkyl, $-V^1-C(=O)NH_2$, $-V^1-C(=O)NHR^6$, $-V^1-C(=O)N(R^6)_2$, $-V^1-C(=O)NHR^7$, $-V^1-C(=O)NR^6R^7$ and $-V^1-C(=O)N(R^7)_2$;

$R^3$ is selected from $(C_1-C_6)$alkyl, $(C_2-C_6)$alkenyl, $(C_2-C_6)$alkynyl, $(C_3-O_5)$cycloalkyl$(C_1-C_4)$alkyl, $(C_1-C_3)$alkoxy$(C_1-C_3)$alkoxy, and $(C_1-C_3)$alkoxy$(C_1-C_3)$alkyl and is optionally substituted with up to four groups independently selected from H, $-F$, $-CN$, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O-$, $(R^4)_2N-$, $R^4O_2C-$, $R^4C(=O)O-$, $R^4S$, $R^4S(=O)-$, $R^4S(=O)_2-$, $R^4C(=O)NR^4-$, $(R^4)_2NC(=O)-$, $(R^4)_2NC(=O)-(R^4)_2NC(=O)NR^4$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4S(=O)_2NHC(=O)O-$, $R^4S(=O)_2NHC(=O)NR^4O$, $(R^4)_2NS(=O)_2NHC(=O)O$, $(R^4)_2NS(=O)_2NHC(=O)O-$, $(R^4)_2NS(=O)_2NHC(=O)$ $NR^4-$, $R^4C(=O)NHS(=O)_2-$, $R^4C(=O)NHS(=O)_2O-$, $R^4C(=O)NHS(=O)_2NR^4-$, $R^4C(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, spirocycloalkyl; heterocyclyl (which in turn is optionally substituted with alkyl, haloalkyl, halogen or oxo), heteroaryl (which in turn is optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn is optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn is optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

n is 0, 1 or 2;

Q is O;

each $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

each $R^6$ is independently $(C_1-C_6)$alkyl, $(C_2-C_6)$alkenyl, $(C_2-C_6)$alkynyl or $(C_1-C_6)$alkoxy;

$V^1$ is $(C_1-C_6)$alkylene, $(C_1-C_6)$alkenylene, $(C_1-C_6)$alkynylene or $(C_1-C_6)$alkyleneoxy;

each $R^7$ is independently $(C_3-C_6)$cycloalkyl or $(C_3-C_6)$cycloalkoxy;

$R^8$ is heterocyclyl; and $R^9$ is $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl or halo$(C_1-C_6)$alkoxy$(C_1-C_6)$alkyl;

or a pharmaceutically acceptable salt, enantiomer or diastereomer thereof.

2. The compound of claim 1 represented by the structural formula (II), (IV), or (VI):

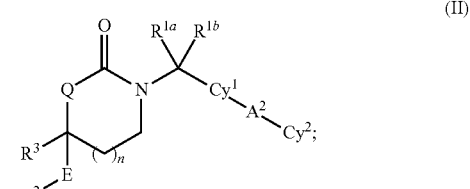

(II)

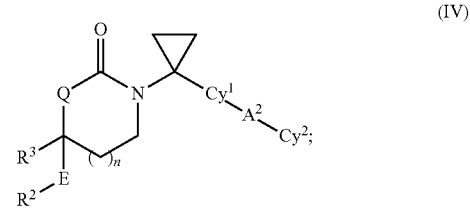

(IV)

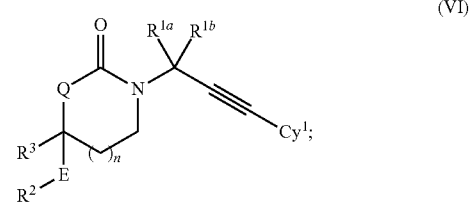

(VI)

or a pharmaceutically acceptable salt, enantiomer or diastereomer thereof, wherein:

R¹ᵃ and R¹ᵇ, in compounds represented by the formula (II) are, independently, optionally substituted (C₁-C₆)alkyl;

R¹ᵃ and R¹ᵇ, in compounds represented by the formula (VI) are, independently, hydrogen, optionally substituted methyl or optionally substituted ethyl, or R¹ᵃ and R¹ᵇ taken together with the carbon to which they are attached form an optionally substituted cyclopropyl group;

Cy¹, in compounds represented by the formulae (II) and (IV), is an optionally substituted cyclohexyl, phenyl, pyridyl, pyrimidinyl, thiazolyl, triazolyl or benzothiazolyl group; and Cy¹, in compounds represented by the formula (VI), is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group.

3. The compound of claim 2, represented by the structural formula (II-A), (III-A), (IV-A), (V), (VI-A), or (VII):

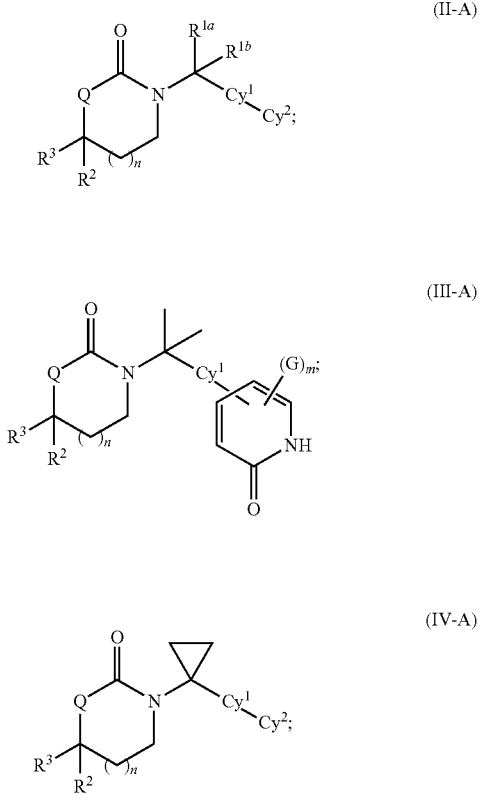

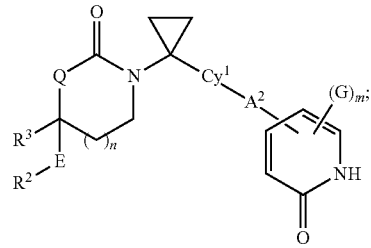

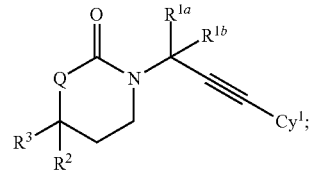

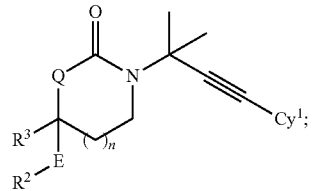

or a pharmaceutically acceptable salt, enantiomer or diastereomer thereof, wherein:

Q is O;

m is 0, 1, 2, 3 or 4;

R¹ᵃ and R¹ᵇ, in compounds of the formula (II-A) are, independently, an optionally substituted methyl or ethyl group;

R¹ᵃ and R¹ᵇ, in compounds of the formula (VI-A) are, independently, hydrogen or methyl, or R¹ᵃ and R¹ᵇ taken together with the carbon to which they are attached form cyclopropyl;

each G, in compounds of the formula (III-A), independently is halogen, —CN, —NO₂, —NH₂, —OH, —COOH, (C₁-C₆)alkyl, (C₂-C₆)alkenyl, (C₂-C₆)alkynyl, (C₁-C₆)alkoxy, (C₃-C₆)cycloalkyl, (C₃-C₆)cycloalkoxy, hydroxy(C₁-C₆)alkyl, hydroxy(C₃-C₆)cycloalkyl, hydroxy(C₂-C₆)alkenyl, hydroxy(C₁-C₆)alkoxy, (C₄-C₇)cycloalkylalkyl, (C₄-C₇)cycloalkylalkoxy, (C₃-C₆)cycloalkyl(C₂-C₄)alkynyl, halo(C₁-C₆)alkyl, halo(C₂-C₆)alkenyl, halo(C₃-C₆)cycloalkyl, halo(C₄-C₇)cycloalkylalkyl, halo(C₁-C₆)alkoxy, halo(C₃-C₆)cycloalkoxy, halo(C₄-C₇)cycloalkylalkoxy, (C₁-C₆)alkoxy(C₁-C₆)alkoxy, halo(C₁-C₆)alkoxy(C₁-C₆)alkoxy, (C₁-C₆)alkoxy(C₁-C₆)alkyl, halo(C₁-C₆)alkoxy(C₁-C₆)alkyl, (C₁-C₆)alkylthio, (C₃-C₆)cycloalkythio, —SR⁹, —S(=O)R⁶, —S(=O)R⁷, —S(=O)R⁹, —S(=O)₂R⁶, —S(=O)₂R⁷, —S(=O)₂R⁹, —NHR⁶, —N(R⁶), —C(=O)⁶, —C(=O)NH₂, —S(=O)₂NH₂, —C(=O)NHR⁶, —C(=O)NR⁶R⁶, —C(=O)R⁸, —S(=O)₂NHR⁶, —S(=O)₂N(R⁶)₂, —S(=O)₂R⁸, —NHC(=O)R⁶, —V¹—NHC(=O)R⁶, —NHS(=O)₂R⁶, —V¹—NHS(=O)₂R⁶, —V¹—C(=O)R⁶, heteroaryl, aryl, heterocyclyl, oxo, —V¹—NH2, —V¹—NHR⁶, —V¹—N(R⁶)₂, —C(=O)R⁷, —C(=O)NHR⁷, —C(=O)NR⁶R⁷, —C(=O)N(R⁷)₂, —S(=O)₂NHR⁷, —S(=O)₂NR⁶R⁷, —S(=O)₂N(R⁷)₂, cyano(C₁-C₆)alkyl, —V¹—C(=O)NH₂, —V¹—C(=O)NHR⁶, —V¹—C(=O)N(R⁶)₂, —V¹—C(=O)NHR⁷, —V¹—C(=O)NR⁶R⁷ or —V¹—C(=O)N(R⁷)₂;

each G, in compounds of the formula (V), independently is halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl, hydroxy(C$_1$-C$_6$)alkoxy, —R$^9$, (C$_1$-C$_6$)alkylthio, (C$_3$-C$_6$)cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ or —V$^1$—C(=O)N(R$^7$)$_2$ Cy$^1$, in compounds of the formulae (III-A) and (V), is an optionally substituted cyclohexyl, phenyl, pyridyl, pyrimidinyl, thiazolyl, triazolyl or benzothiazolyl group; and Cy$^1$, in compounds of the formula (VII), is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, cyclohexyl or cyclopropyl group.

4. The compound of claim 3, represented by structural formula (II-B), (III-B), (IV-B), (V-A), (VI-B), or (VII-A):

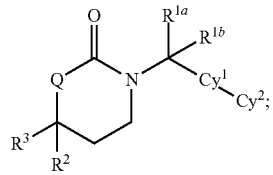

(II-B)

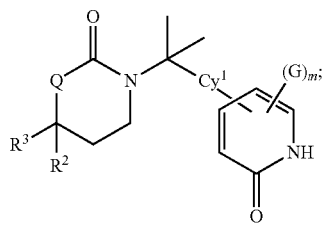

(III-B)

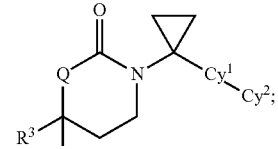

(IV-B)

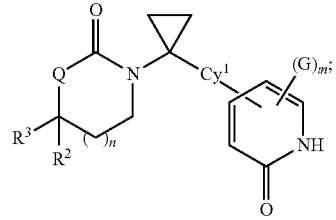

(V-A)

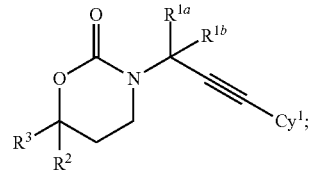

(VI-B)

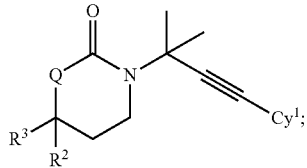

(VII-A)

or a pharmaceutically acceptable salt, enantiomer or diastereomer thereof, wherein:

in compounds of the formula (II-B):
Cy$^2$, is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group; and R$^{1a}$ and R$^{1b}$ are, independently, optionally substituted methyl;

in compounds of the formula (III-B):
Cy$^1$ is an optionally substituted phenyl or triazolyl group;

in compounds of the formula (IV-B):
Cy$^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group; and in compounds of the formula (VI-B):

$Cy^1$ is an optionally substituted phenyl or oxodihydroquinolinyl group.

5. The compound of claim 4, represented by structural formula (II-C), (IV-C), (V-B), or (VII-B):

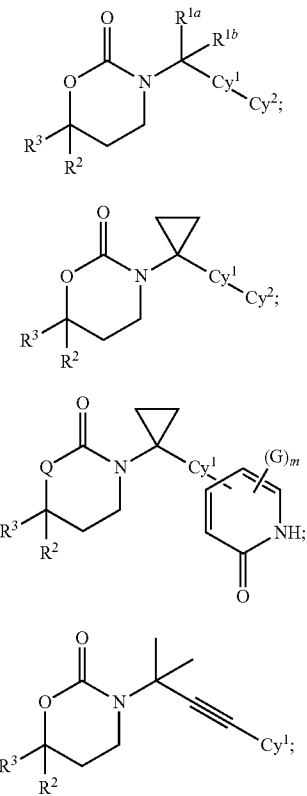

(II-C)

(IV-C)

(V-B)

(VII-B)

or a pharmaceutically acceptable salt, enantiomer or diastereomer thereof, wherein:

$Cy^1$, in compounds of the formulae (II-C), (IV-C), and (V-B), is an optionally substituted phenyl or triazolyl group;

$Cy^1$, in compounds of the formula (VII-B), is optionally substituted phenyl; and $Cy^2$, in compounds of the formulae (II-C) and (IV-C), is a phenyl or oxodihydropyridyl group, each of which is optionally substituted with one to four groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl and hydroxy(C$_1$-C$_6$)alkoxy.

6. The compound of claim 5, represented by the structural formula (II-E) or (IV-D):

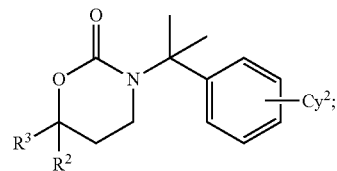

(II-E)

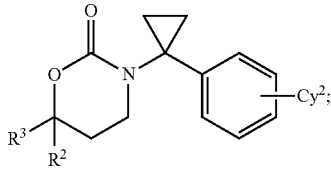

(IV-D)

or a pharmaceutically acceptable salt, enantiomer or diastereomer thereof, wherein:

$Cy^2$ is optionally substituted with one to four groups independently selected from (C$_1$-C$_6$)alkyl and (C$_3$-C$_6$)cycloalkyl.

7. The compound of claim 6, wherein $R^3$ is (C$_3$-C$_6$)alkenyl, hydroxy(C$_2$-C$_5$)alkyl, cyano(C$_2$-C$_5$)alkyl, dihydroxy(C$_3$-C$_5$) alkyl, ω-H$_2$NCO(C$_1$-C$_5$)alkyl, (C$_1$-C$_2$)alkoxy(C$_1$-C$_4$)alkyl, H$_2$NSO$_2$O(C$_2$-C$_5$)alkyl, H$_2$NSO$_2$NH(C$_2$-C$_5$)alkyl, oxo(C$_2$-C$_5$)alkyl, MeC(=O)NH(C$_2$-C$_5$)alkyl, MeSO$_2$NH(C$_2$-C$_5$) alkyl, or MeSO$_2$NH(C$_2$-C$_5$)alkyl.

8. The compound of claim 6, wherein $R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O) NH—, H$_2$NCH$_2$C(=O)NH—, EtNHC(=O)NH, MeOC(=O)NH—, MeNHC(=NC≡N)NH—, MeS—, MeSO$_2$-MeSO$_2$N(Me)—, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH-, Me$_2$N—and MeCONMe.

9. The compound of claim 6, wherein $R^2$ is an optionally substituted (C$_1$-C$_6$)alkyl, aryl, heteroaryl or cycloalkyl group, E is a bond or CH$_2$ and $R^3$ is methyl, ethyl, propyl, butyl, vinyl, allyl or ethoxyethyl, each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC≡N)NH—, MeS—, MeS$_2$- MeSO$_2$N(Me)—, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N—and MeCONMe.

10. The compound of claim 9, wherein
$R^2$ is phenyl, fluorophenyl, isopropyl, cyclopropyl, t-butyl or trifluoroethyl, or E-R$^2$ is cyclopropylmethyl, and the group represented by $R^2$ or E-R$^2$ is optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen, cyano and nitro; and $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, HO$_2$C—, (HO)$_2$P(=O)O—, $H_2$NS(=O)$_2$—, $H_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, $H_2$NCH$_2$C(=O)NH—, EtNHC(=O)NH, MeOC(=O)NH—, MeNHC(=NC≡N)NH—, MeS—, MeSO$_2$-MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2$NCONH—, $H_2$NCO$_2$—, HOCH$_2$CH$_2$O—, MeNH—, Me$_2$N—and MeCONMe.

11. The compound of claim 9, wherein $R^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen, cyano and nitro;

$R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, HO$_2$C—, (HO)$_2$P(=O)O—, $H_2$NS(=O)$_2$O—, $H_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, $H_2$NCH$_2$C(=)NH—, EtNHC(=O)NH, MeOC(=O)NH—, MeNHC(=NC≡N)NH—, MeS—, MeSO$_2$—MeSO$_2$N(Me)—, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2$NCONH—, $H_2$NCO$_2$—, HOCH$_2$CH$_2$O—, MeNH—, Me$_2$N—and MeCONMe;

the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl; and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethyl-amino-sulfonyl, pyrrolidine-1-sulfonyl, methylsulfonylaminomethyl, tetrazolyl, trifluoromethyl, acetyl, 2-hydroxyethyl, 1-aminoethyl, deuteromethyl, t-butyl, difluoromethyl, 2-fluoroethyl, 2,2,2-trifluoroethyl, 2-hydroxy-2-propyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, and methylthio.

12. The compound of claim 9, wherein
$R^2$ is phenyl optionally substituted with one to three groups independently selected from $(C_1-C_4)$alkyl, $(C_1-C_4)$alkoxy, $(C_1-C_4)$halo alkyl, $(C_1-C_4)$haloalkoxy, halogen, cyano and nitro;

$R^3$ is 2-methylallyl, MeSO$_2$NHCH$_2$CH$_2$CH$_2$, $H_2$NC(=O)CH$_2$CH$_2$, $H_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl;

the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl; and the group represented by $Cy^2$ is optionally substituted 1 to 4 groups independently selected from methyl, ethyl, propyl, cyclopropyl, halo, hydroxy, methoxy, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethyl-amino-sulfonyl, pyrrolidine-1-sulfonyl, methylsulfonylaminomethyl, tetrazolyl, trifluoromethyl, acetyl, 2-hydroxyethyl and 1-aminoethyl, deuteromethyl, t-butyl, difluoromethyl, 2-fluoroethyl, 2,2,2-trifluoroethyl, 2-hydroxy-2-propyl, 2-hydroxy-2-methylpropyl, 2-methoxy-2-methylpropyl, 3-methoxy-2-methylpropyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, cyano, cyclopropylmethyl, methylsulfinyl, and methylthio.

13. The compound of claim 9, wherein
$R^2$ is phenyl or fluorophenyl;
$R^3$ is 2-methylallyl, 2-hydroxy-2-methylpropyl or 2-cyano-2-methylpropyl; and
the groups represented by $Cy^1$ and $Cy^2$ are each, independently, optionally substituted with fluoro, chloro, cyano, CONH$_2$, CONHMe, CONMe$_2$, CONHc-Pr, methyl, ethyl, cyclopropyl, difluoromethyl, CF$_3$ or oxo.

14. A method of treating a subject with a disease or disorder selected from diabetes mellitus, obesity, prothrombotic state, proinflammatory state, metabolic syndrome, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, Alzheimer's disease, depression, anxiety, dementia, cognitive decline, polycystic ovarian syndrome, hypergonadism, tuberculosis, leprosy, psoriasis, to promote wound healing, hypertriglyceridemia, hypercholesterolemia, low HDL levels, high LDL levels, vascular restenosis, pancreatitis, abdominal obesity, coronary heart disease, peripheral vascular disease, hyperinsulinemia, viral diseases, and Syndrome X; comprising the step of administering to the subject an effective amount of the compound of claim 1.

15. A pharmaceutical composition comprising: i) a pharmaceutically acceptable carrier or diluent; and ii) the compound of claim 1; or a pharmaceutically acceptable salt, enantiomer or diastereomer thereof.

* * * * *